(12) United States Patent
Hébert et al.

(10) Patent No.: US 11,259,738 B2
(45) Date of Patent: Mar. 1, 2022

(54) USE OF ELECTRORETINOGRAPHY (ERG) FOR THE ASSESSMENT OF PSYCHIATRIC DISORDERS

(71) Applicant: Université Laval, Quebec (CA)

(72) Inventors: Marc Hébert, Quebec (CA); Michel Maziade, Quebec (CA); Chantal Mérette, Quebec (CA)

(73) Assignee: Université Laval, Québec (CA)

( * ) Notice: Subject to any disclaimer, the term of this patent is extended or adjusted under 35 U.S.C. 154(b) by 278 days.

(21) Appl. No.: 16/685,960

(22) Filed: Nov. 15, 2019

(65) Prior Publication Data

US 2020/0085338 A1 Mar. 19, 2020

Related U.S. Application Data

(63) Continuation of application No. 14/774,802, filed as application No. PCT/CA2014/050233 on Mar. 13, 2014, now abandoned.

(Continued)

(51) Int. Cl.
*A61B 5/0496* (2006.01)
*A61B 5/16* (2006.01)
(Continued)

(52) U.S. Cl.
CPC ............ *A61B 5/398* (2021.01); *A61B 3/10* (2013.01); *A61B 5/163* (2017.08); *A61B 5/165* (2013.01);
(Continued)

(58) Field of Classification Search
CPC ......... A61B 5/165; A61B 5/168; A61B 5/163; A61B 5/055; A61B 5/377; A61B 5/389; A61B 5/4088; A61B 2576/026; A61B 5/167; A61B 5/375; A61B 5/378; A61B 5/38; A61B 5/381; A61B 5/4011; A61B 5/4017; A61B 5/4064; A61B 5/6814; A61B 5/7267; A61B 6/501; A61B 3/113; A61B 5/16; A61B 5/162; A61B 5/291; A61B 5/4094; A61B 5/4848; A61B 2503/40;
(Continued)

(56) References Cited

U.S. PATENT DOCUMENTS 7,338,455 B2 3/2008 White et al.
7,670,764 B2 3/2010 Oh et al.
(Continued)

FOREIGN PATENT DOCUMENTS

RU 2141245 C1 11/1999
WO WO-2007/061469 A1 5/2007
(Continued)

OTHER PUBLICATIONS

Balogh et al., Retinal dysfunctions in schizophrenia, Progress in Neuro-Psychopharmacology & Biological Psychiatry 32 (2008) 297-300 .

(Continued)

*Primary Examiner* — Sean P Dougherty
*Assistant Examiner* — Benjamin S Melhus
(74) *Attorney, Agent, or Firm* — Marshall, Gerstein & Borun LLP

(57) ABSTRACT

Methods for the diagnosis, prognosis, patient stratification and prediction of pharmacological response in patients afflicted by psychiatric disorders based on electroretinography (ERG) parameters are described.

20 Claims, 17 Drawing Sheets

Related U.S. Application Data

(60) Provisional application No. 61/781,520, filed on Mar. 14, 2013.

(51) Int. Cl.

| | |
|---|---|
| *A61B 5/00* | (2006.01) |
| *G16H 50/20* | (2018.01) |
| *A61B 3/10* | (2006.01) |
| *A61B 5/398* | (2021.01) |

(52) U.S. Cl.
CPC ............ *A61B 5/167* (2013.01); *A61B 5/4088* (2013.01); *A61B 5/4848* (2013.01); *A61B 5/72* (2013.01); *A61B 5/7246* (2013.01); *A61B 5/7275* (2013.01); *G16H 50/20* (2018.01)

(58) Field of Classification Search
CPC ....... A61B 3/032; A61B 5/0035; A61B 5/296; A61B 5/316; A61B 5/318; A61B 5/4076; A61B 5/4082; A61B 5/6803; A61B 5/7203; A61B 5/7264; A61B 5/7275; A61B 5/7285; A61B 5/7425; A61B 5/743; A61B 6/037; A61B 6/4417; A61B 6/5247; A61B 6/541; A61B 8/0808; A61B 8/543; G06F 3/013
See application file for complete search history.

(56) References Cited

U.S. PATENT DOCUMENTS

| | | | |
|---|---|---|---|
| 7,959,578 | B2 | 6/2011 | Lonky |
| 2009/0257023 | A1 | 10/2009 | Greenlee et al. |
| 2011/0245169 | A1 | 10/2011 | Brines et al. |
| 2011/0245734 | A1 | 10/2011 | Wagner et al. |
| 2011/0275927 | A1 | 11/2011 | Wagner et al. |
| 2012/0053242 | A1 | 3/2012 | Cela Lopez |
| 2012/0059060 | A1 | 3/2012 | Blanda et al. |
| 2012/0093772 | A1 | 4/2012 | Horsager et al. |
| 2012/0142589 | A1 | 6/2012 | Brines et al. |
| 2015/0105689 | A1 | 4/2015 | Miller |

FOREIGN PATENT DOCUMENTS

| | | |
|---|---|---|
| WO | WO-2011/119869 A1 | 9/2011 |
| WO | WO-2011/133890 A1 | 10/2011 |
| WO | WO-2012/021773 A1 | 2/2012 |
| WO | WO-2012/051599 A2 | 4/2012 |
| WO | WO-2012/116334 A2 | 8/2012 |

OTHER PUBLICATIONS

Barraco et al., A comparison among different techniques for human ERG signals processing and classification Physica Medica 2013.

Barraco et al., An approach based on wavelet analysis for feature extraction in the a-wave of the 3lectroretinogramComput Met Prog Biomed Elsevier Health, 2011.

Bubl et al., Seeing Gray When Feeling Blue? Depression Can Be Measured in the Eye of the Diseased Biol Psychiatry, 2010.

Bubl et al., Effect of antidepressive therapy on retinal, This British Journal of Psychiatry 2012 contrast processing in lepressive disorder.

Castrogiovanni et al., Electroretinogram B-wave amplitude in panic disorder 2001, Abstract.

Electroretinograms, Gregor Beltitio; free online editions of InTech Books and Journals can be found at www.intechopen.com.

European Patent Application No. 19166255, European Search Report, dated Jun. 28, 2019.

Fam et al., Visual contrast sensitivity in major depressive disorder, Journal of psychosomatic Research 2013.

Fornaro et al., Electroretinographic assessment in major depressed patients receiving duloxetine: Might differences between responders and non-responders indicate a differential biological background? J Affect Disord 2011.

Forte et al., Wavelet analysis reveals dynamics of rat oscillatory potentials, J Neurosci Met 2008.

Fountoulakis et al., Is there a dysfunction on the visual system of depressed patients?, Annals Gen Psyc, Mar. 2005.

Gagne et al., Atypical pattern of rod electroretinogram modulation by recent light history: A possible biomarker of seasonal affective disorder, 2011.

Gschwandtner et al. "EEG: a helpful tool in the prediction of psychosis", Eur. Arch. Psychiatry Clin. Neurosci., vol. 259, pp. 257-262, Apr. 11, 2009 (Apr. 11, 2009).

Hebert et al. Retinal Response to Light in Young Nonaffected Offspring at High Genetic Risk of Neuropsychiatric Brain Disorders, Research Report, Biol Psychiatry 2010.

Hebert et al., Electroretinography in patients with winter seasonal affective disorder, Psychiatry Research 127, 2004.

Holopigian et al., The effects of dopamine blockade on the human flash electroretinogram, Documenta Dphthalmologica 86: 1-10, 1994.

Jahshan wt al., Nonconscious and conscious color priming in schizophrenia Journal of Psychiatric Research 2012.

Lam et al., Electroretinography in Seasonal Affective Disorder, Psychiatry Res 1992.

Lavoie et al. "The electroretinogram as a biomarker of central dopamine and serotonin: potential relevance to psychiatric disorders", Biol. Psychiatry, vol. 75, No. 6, pp. 479-486, Jan. 7, 2013 (Jan. 7, 2013).

Lavoie et al., Abstract Electroretinogram Anomalies in Psychiatric Disorders: The Possible Implication of GSK3, May 10, 2012.

Lavoie et al., Evidence of a biological effect of light therapy on the retina of patients with seasonal affective disorder.

Llewellyn, If waking and dreaming consciousness became de-differentiated, would schizophrenia result?, Consciousness and Cognition Elsevier Inc. 2011.

Martin-Facklam et al., Several Prescription Patterns of Antipsychotic Drugs Influence 3ognitive Functions in Japanese Chronic Schizophrenia Patients, Abstracts of the 3rd Biennial Schizophrenia International Research Conference / Schizophrenia Research 136, Supplement 1 (2012) S1-S375.

Maziade, 2005.

Miller, Functional neuro-ophthalmology, Handbook of Clinical Neurology, vol. 102.

Realmuto et al., Electroretinograms (ERGs) in Four Autistic Probands and Six First-Degree Relatives, Canadian vol. of Psychiatry 1989.

Schechter Electroniretinographic Assessment in Schizophrenia, ElecClinNeuroSuppl., 1987.

Seggie, ClinInvestMed, 1990.

Tzelepi; The push-pull action of dopamine on spatial tuning of the monkey retina: the effects of dopaminergic leficiency and selective D1 and D2 receptor ligands on the pattern electroretinogram, Vision Research 38 (1998) 1479-1487.

Warner et al., Retinal Function as a Marker for Cell Membrane Omega-3 Fatty Acid Depletion in Schizophrenia: A Pilot Study, Biol Psychiatry 1999;45:1138-1142.

Wendy W. Harrison, Marcus A. Bearse, Jason S. Ng, Nicholas P. Jewell, Shirin Barez, Dennis Burger, Marilyn E. Schneck, Anthony J. Adams; Multifocal Electroretinograms Predict Onset of Diabetic Retinopathy in Adult Patients with Diabetes. Invest. Ophthalmol. Vis. Sci. 2011 ;52(2):772-777. doi: 10.1167/iovs.10-5931.

Yeap et al., Visual sensory processing deficits in Schizophrenia and their relationship to disease state Eur Arch Psychiatry Clin Neurosci (2008) 258:305-3162008.

Fournier et al., Prediction of response to medication and cognitive therapy in the treatment of moderate to severe depression, J. Consult. Clin. Psychol., 77(4):775-87 (Aug. 2009).

European Patent Application No. 20180150.3, European Search Report, dated Feb. 9, 2021.

USE OF ELECTRORETINOGRAPHY (ERG) FOR THE ASSESSMENT OF PSYCHIATRIC DISORDERS

CROSS REFERENCE TO RELATED APPLICATIONS

The present application is a continuation of U.S. patent application Ser. No. 14/774,802, which is the U.S. national phase of International Patent Application No. PCT/CA2014/050233, filed on Mar. 13, 2014, which claims priority benefit under 35 U.S.C. § 119 of U.S. Provisional Application Ser. No. 61/781,520, filed on Mar. 14, 2013, which is incorporated herein by reference in its entirety.

TECHNICAL FIELD

The present invention generally relates to mental disorders, such as psychiatric disorders, and more particularly to the use of biomarkers for the screening, prognosis (predisposition or susceptibility), diagnosis, differential diagnosis, monitoring and/or stratification of patients afflicted by such disorders, as well as the use of different biomarkers for the prediction of pharmacological response and pharmacodynamics in patients afflicted by such disorders.

BACKGROUND ART

Psychiatric disorders are characterized by alterations in thinking, mood or behaviour—or some combination thereof—associated with significant distress and impaired functioning.

Schizophrenia (SZ) and related disorders such as brief psychotic disorder, delusional disorder, schizoaffective disorder, and schizophreniform disorder, are characterized by psychotic symptoms. Psychotic symptoms include delusions, hallucinations, disorganized thinking and speech, and bizarre and inappropriate behavior. Schizophrenia is characterized by psychosis (loss of contact with reality), hallucinations (false perceptions), delusions (false beliefs), disorganized speech and behavior, flattened affect (restricted range of emotions), cognitive deficits (impaired reasoning and problem solving), and occupational and social dysfunction. Diagnosis is typically based on the patient's self-reported experiences and observed behavior.

Bipolar disorders (BP) are characterized by episodes of mania and depression, which may alternate, although many patients have a predominance of one or the other.

Major depressive disorder (MDD) (also known as recurrent depressive disorder, clinical depression, or major depression) is a mental disorder characterized by episodes of all-encompassing low mood accompanied by low self-esteem and loss of interest or pleasure in normally enjoyable activities.

There is no reliable diagnostic test for psychiatric disorders. The diagnosis of psychiatric disorders typically requires evaluation by a trained mental-health professional and usually an interview, administration of a variety of personality tests (and in some cases, neuropsychological tests), and gathering of background (including medical) information about the individual (e.g., patient's self-reported experiences, behavior reported by relatives or friends). Etiological heterogeneity within the Diagnostic and Statistical Manual of Mental Disorders (DSM) categories (meaning that within a particular DSM category, there are different subgroups of patients whose disease is underlain by different neurobiological pathologies) diminishes the power of pharmacological/clinical trials and neurobiological studies of major psychiatric disorders. No valid and replicable biomarkers of this heterogeneity have been identified. There is also an increasing awareness that the widely used DSM diagnoses have porous boundaries, meaning that some neurobiological etiological processes are common to several of these diagnoses. Obstacles to rapid progress are threefold: 1. Direct access to central nervous system in humans to investigate neurotransmitter system interplays; 2. Physiological endophenotypes that may help to stratify patients and to understand psychiatric disease processes and treatment response and 3. Longitudinal access to already available intelligent multiphenotype biobank.

There is thus a need for the development of novel methods and biomarkers that may help to screen, confirm diagnosis, stratify, select treatment or predict outcome of patients afflicted by psychiatric disorders.

The present description refers to a number of documents, the content of which is herein incorporated by reference in their entirety.

SUMMARY OF THE INVENTION

In an aspect, the present invention provides a method of identifying a model, based on one or more markers/measures of retinal function, for example one or more ERG parameters, that permits to discriminate between a first group of subjects and a second group of subjects that differ by at least one characteristics, wherein said first group and/or second group of subjects suffer from a psychiatric disorder or a has a predisposition thereto, said method comprising (a) measuring a plurality of markers/measures of retinal function, for example a plurality of ERG parameters, in said subjects; (b) performing a logistic regression analysis using the plurality of markers/measures of retinal function (for example ERG parameters) measured to identify a model that permits to discriminate between a first group and a second group of subjects. In another aspect, the present invention provides a method of identifying a model, based on one or more markers/measures of retinal function, for example one or more ERG parameters, that permits to discriminate between a first group of subjects and a second group of subjects that differ by at least one characteristics, wherein said first group and/or second group of subjects suffer from a psychiatric disorder or a has a predisposition thereto, said method comprising performing a logistic regression analysis using a plurality of markers/measures of retinal function (for example ERG parameters) from said subjects to identify a model that permits to discriminate between a first group and a second group of subjects.

In an embodiment, the logistic regression analysis is multiple stepwise logistic regression analysis. In a further embodiment, the logistic regression analysis includes age, gender, or both age and gender as covariate(s), in yet a further embodiment both age and gender are included as covariate in said analysis.

In an embodiment, the plurality of ERG parameters comprises at least two of the following parameters: the cone a-Wave amplitude (phAamp), the cone a-Wave implicit time (phAlat), the cone b-Wave amplitude (phBamp), the cone b-Wave implicit time (phBlat), the rod a-Wave amplitude (scAamp), the rod a-Wave implicit time (scAlat), rod b-Wave amplitude (scBamp), the rod b-Wave implicit time (scBlat), the Log K and the Vmax. In a further embodiment, the plurality of ERG parameters comprises at least four of the following parameters: the cone a-Wave amplitude (phAamp), the cone a-Wave implicit time (phAlat), the cone b-Wave amplitude (phBamp), the cone b-Wave implicit time (phBlat), the rod a-Wave amplitude (scAamp), the rod a-Wave implicit time (scAlat), rod b-Wave amplitude (scBamp) and the rod b-Wave implicit time (scBlat), the Log K and the Vmax. In an embodiment, the plurality of ERG parameters comprises all the following parameters: the cone a-Wave amplitude (phAamp), the cone a-Wave implicit time (phAlat), the cone b-Wave amplitude (phBamp), the cone b-Wave implicit time (phBlat), the rod a-Wave amplitude (scAamp), the rod a-Wave implicit time (scAlat), rod b-Wave amplitude (scBamp) and the rod b-Wave implicit time (scBlat).

In an embodiment, the at least one characteristics comprises the type of psychiatric disorder or predisposition thereto, and wherein the first group of subjects suffer from a first psychiatric disorder or has a predisposition thereto and said second group of subjects suffer from a second psychiatric disorder or has a predisposition thereto. In an embodiment, the first psychiatric disorder is schizophrenia (SZ). In another embodiment, the second psychiatric disorder is bipolar disorder (BP) or major depressive disorder (MDD). In another embodiment, the first psychiatric disorder is BP and the second psychiatric disorder is MDD.

In another embodiment, the at least one characteristics comprises the presence or absence of the psychiatric disorder or predisposition thereto, and wherein said first group of subjects suffer from a psychiatric disorder or has a predisposition thereto and said second group of subjects do not suffer from a psychiatric disorder or do not have a predisposition thereto. In an embodiment, the first group of subjects suffer from SZ or have a predisposition thereto. In another embodiment, the first group of subjects suffer from BP or have a predisposition thereto. In another embodiment, the first group of subjects suffer from MDD or have a predisposition thereto. In an embodiment, the at least one characteristics comprises the response to a psychotropic medication, and wherein said at least one characteristics comprises the response to a psychotropic medication, and wherein said first group of subjects are good responders to a psychotropic medication and said second group of subjects are poor responders to said psychotropic medication. In a further embodiment, the psychotropic medication is an antipsychotic medication or a mood stabilizer medication. In a further embodiment, the psychotropic medication comprises quetiapine. In another embodiment, the psychotropic medication comprises aripiprazole. In another embodiment, the psychotropic medication comprises olanzapine. In another embodiment, the psychotropic medication comprises lithium. In another embodiment, the psychotropic medication comprises clozapine.

In an embodiment, the above-mentioned method further comprises determining the accuracy, sensitivity and/or specificity of the model. In an embodiment, the accuracy, sensitivity and/or specificity of the model is determined by calculating the Area Under the Receiver Operating Curve (AU-ROC).

In another aspect, the present invention provides a method of determining the likelihood that a test subject belongs to a first group of subjects or a second group of subjects that differ by at least one characteristics, said method comprising (a) measuring at least one markers/measures of retinal function, for example ERG parameters, in said test subject; (b) analysing the at least one markers/measures of retinal function, for example ERG parameters, measured using the model identified according to the method defined above to determine the likelihood that the test subject belongs to the first group or second group of subjects. In another aspect, the present invention provides a method of determining the likelihood that a test subject belongs to a first group of subjects or a second group of subjects that differ by at least one characteristics, said method comprising analysing at least one markers/measures of retinal function, for example ERG parameters, from the test subject using the model identified according to the method defined above to determine the likelihood that the test subject belongs to the first group or second group of subjects.

In another aspect, the present invention provides a method for determining whether a subject suffers from schizophrenia (SZ) or has a predisposition thereto, said method comprising (a) measuring one or more markers/measures of retinal function, for example ERG parameters, in the subject, in an embodiment one or more of the following ERG parameters: the cone a-Wave amplitude (phAamp), the cone a-Wave implicit time (phAlat), the cone b-Wave amplitude (phBamp), the cone b-Wave implicit time (phBlat), the rod a-Wave amplitude (scAamp), the rod a-Wave implicit time (scAlat), rod b-Wave amplitude (scBamp) and the rod b-Wave implicit time (scBlat), in the subject; (b) calculating an SZ probability score by adjusting the value of one or more of the ERG parameters by one or more transformation analyses; and (c) determining whether the subject suffers from schizophrenia (SZ) or has a predisposition thereto based on the SZ probability score. In another aspect, the present invention provides a method for determining whether a subject suffers from SZ or has a predisposition thereto, said method comprising (a) calculating an SZ probability score by adjusting the value of one or more markers/measures of retinal function, for example ERG parameters, from the subject by one or more transformation analyses; and (b) determining whether the subject suffers from SZ or has a predisposition thereto based on the SZ probability score In an embodiment, the method does not comprise or excludes using to solely the cone a-Wave amplitude to calculate the SZ probability score. In another embodiment, the method does not comprise or excludes using to solely the rod b-Wave amplitude to calculate the SZ probability score. In another embodiment, the method does not comprise or excludes using to solely the cone a-Wave amplitude and the rod b-Wave amplitude to calculate the SZ probability score. In another embodiment, at least two ERG parameters are used to calculate the SZ probability score. In another embodiment, at least 3 ERG parameters are used to calculate the SZ probability score.

In another aspect, the present invention provides a method for determining whether a subject suffers from a bipolar disorder (BP) or has a predisposition thereto, said method comprising (a) measuring one or more markers/measures of retinal function, for example ERG parameters in the subject, in an embodiment one or more of the following ERG parameters: the cone a-Wave amplitude, the cone a-Wave implicit time, the cone b-Wave amplitude, the cone b-Wave implicit time, the rod a-Wave amplitude, the rod a-Wave implicit time, rod b-Wave amplitude and the rod b-Wave implicit time, in the subject; (b) calculating a BP probability score by adjusting the value of one or more of the markers/measures of retinal function, for example ERG parameters, by one or more transformation analyses; and (c) determining whether the subject suffers from bipolar disorder (BP) or has a predisposition thereto based on the BP probability score. In another aspect, the present invention provides a method for determining whether a subject suffers from a bipolar disorder (BP) or has a predisposition thereto, said method comprising (a) calculating a BP probability score by adjusting the value of one or more markers/measures of retinal function, for example ERG parameters, from the subject by one or more transformation analyses; and (b) determining whether the subject suffers from bipolar disorder (BP) or has a predisposition thereto based on the BP probability score. In an embodiment, the method does not comprise or excludes using to solely the rod b-Wave amplitude to calculate the BP probability score. In another embodiment, at least two ERG parameters are used to calculate the BP probability score.

In another aspect, the present invention provides a method for predicting if a subject suffering from a psychiatric disorder or having a predisposition thereto is likely to respond to a psychotropic medication, the method comprising: (a) measuring one or more markers/measures of retinal function, for example ERG parameters, in the subject, in an embodiment one or more of the following ERG parameters: the cone a-Wave amplitude, the cone a-Wave implicit time, the cone b-Wave amplitude, the cone b-Wave implicit time, the rod a-Wave amplitude, the rod a-Wave implicit time, the rod b-Wave amplitude and the rod b-Wave implicit time, in the subject; (b) calculating a psychotropic medication response probability score by adjusting the value of one or more of the markers/measures of retinal function, for example ERG parameters, by one or more transformation analyses; and (c) determining whether the subject is likely to respond to the psychotropic medication based on the psychotropic medication response probability score. In another aspect, the present invention provides a method for predicting if a subject suffering from a psychiatric disorder or having a predisposition thereto is likely to respond to a psychotropic medication, the method comprising: (a) calculating a psychotropic medication response probability score by adjusting the value of one or more markers/measures of retinal function, for example ERG parameters, from the subject by one or more transformation analyses; and (b) determining whether the subject is likely to respond to the psychotropic medication based on the psychotropic medication response probability score. In an embodiment, the method does not comprise or excludes using to solely the cone a-Wave amplitude to calculate the psychotropic medication response probability score. In another embodiment, at least two ERG parameters are used to calculate the psychotropic medication response probability score.

In another aspect, the present invention provides a method for identifying one or more markers/measures of retinal function, for example ERG parameters, useful for discriminating between subjects suffering from a psychiatric disorder having a likelihood to respond to a psychotropic medication of more than 50%, and subjects suffering from a psychiatric disorder having a likelihood to respond to a psychotropic medication of less than 50%, said method comprising: administering said psychotropic drug to a group of subjects; determining whether the subjects have responded to the psychotropic drug; measuring one or more markers/measures of retinal function, for example ERG parameters, in the subjects; and identifying the one or more markers/measures of retinal function, for example ERG parameters, that permit to discriminate between the subjects who responded to the psychotropic drug and the subjects who did not respond to the psychotropic drug. In another aspect, the present invention provides a method for identifying one or more markers/measures of retinal function, for example ERG parameters useful for discriminating between subjects suffering from a psychiatric disorder having a likelihood to respond to a psychotropic medication of more than 50%, and subjects suffering from a psychiatric disorder having a likelihood to respond to a psychotropic medication of less than 50%, said method comprising: determining whether the subjects have responded to a psychotropic medication; and identifying one or more markers/measures of retinal function, for example ERG parameters, that permit to discriminate between the subjects who responded to the psychotropic medication and the subjects who responded poorly to the psychotropic medication.

In another aspect, the present invention provides a method for determining whether a subject (i) suffers from SZ or has a predisposition thereto or (ii) suffers from BP or has a predisposition thereto, said method comprising: (a) measuring one or more markers/measures of retinal function, for example ERG parameters, in the subject, in an embodiment one or more of the following ERG parameters: the cone a-Wave amplitude, the cone a-Wave implicit time, the cone b-Wave amplitude, the cone b-Wave implicit time, the rod a-Wave amplitude, the rod a-Wave implicit time, rod b-Wave amplitude and the rod b-Wave implicit time, in the subject; (b) calculating an SZ or BP probability score by adjusting the value of one or more of the markers/measures of retinal function, for example ERG parameters, by one or more transformation analyses; and (c) determining whether the subject suffers from SZ or BP or has a predisposition thereto based on the SZ or BP probability score. In another aspect, the present invention provides a method for determining whether a subject (i) suffers from SZ or has a predisposition thereto or (ii) suffers from BP or has a predisposition thereto, said method comprising (a) calculating an SZ or BP probability score by adjusting the value of one or more markers/measures of retinal function, for example ERG parameters, from the subjects by one or more transformation analyses; and (b) determining whether the subject suffers from SZ or BP or has a predisposition thereto based on the SZ or BP probability score In an embodiment, the method does not comprise or excludes using to solely the cone a-Wave amplitude to calculate the SZ or BP probability score. In another embodiment, at least two ERG parameters are used to calculate the SZ or BP probability score.

In another aspect, the present invention provides a method for determining whether an asymptomatic young subject is at risk of suffering from a psychiatric disorder, said method comprising (a) measuring one or more markers/measures of retinal function, for example ERG parameters, in the subject, in an embodiment one or more of the following ERG parameters: the cone a-Wave amplitude, the cone a-Wave implicit time, the cone b-Wave amplitude, the cone b-Wave implicit time, the rod a-Wave amplitude, the rod a-Wave implicit time, the rod b-Wave amplitude and the rod b-Wave implicit time, in the subject; (b) calculating a psychiatric disorder risk probability score by adjusting the value of one or more of the markers/measures of retinal function, for example ERG parameters, by one or more transformation analyses; and (c) determining whether the asymptomatic young subject is at risk of suffering from a psychiatric disorder based on said psychiatric disorder risk probability score. In another aspect, the present invention provides a method for determining whether an asymptomatic young subject is at risk of suffering from a psychiatric disorder, said method comprising (a) calculating a psychiatric disorder risk probability score by adjusting the value of one or more markers/measures of retinal function, for example ERG parameters, from the subject by one or more transformation analyses; and (b) determining whether the asymptomatic young subject is at risk of suffering from a psychiatric disorder based on said psychiatric disorder risk probability score. In an embodiment, the method does not comprise or excludes using to solely the rod b-Wave amplitude to calculate the psychiatric disorder risk probability score. In an embodiment, at least two ERG parameters are used to calculate the psychiatric disorder risk probability score.

In another aspect, the present invention provides a method for determining whether a subject suffers from major depression (MDD) or has a predisposition thereto, said method comprising (a) measuring one or more markers/measures of retinal function, for example ERG parameters, in the subject, in an embodiment one or more of the following ERG parameters: the cone a-Wave amplitude, the cone a-Wave implicit time, the cone b-Wave amplitude, the cone b-Wave implicit time, the rod a-Wave amplitude, the rod a-Wave implicit time, the rod b-Wave amplitude and the rod b-Wave implicit time, in the subject; (b) calculating an MDD probability score by adjusting the value of one or more of the markers/measures of retinal function, for example ERG parameters, by one or more transformation analyses; and (c) determining whether the subject suffers from MDD or has a predisposition thereto based on said MDD probability score. In another aspect, the present invention provides a method for determining whether a subject suffers from major depression (MDD) or has a predisposition thereto, said method comprising (a) calculating an MDD probability score by adjusting the value of one or more markers/measures of retinal function, for example ERG parameters, by one or more transformation analyses; and (b) determining whether the subject suffers from MDD or has a predisposition thereto based on said MDD probability score. In an embodiment, the method does not comprise or excludes using to solely the rod b-Wave amplitude to calculate the MDD probability score. In an embodiment, at least two ERG parameters are used to calculate the MDD probability score.

In another aspect, the present invention provides a method for identifying one or more markers/measures of retinal function, for example ERG parameters, useful for discriminating between subjects suffering from MDD or predisposed thereto, and non-MDD subjects, said method comprising: selecting a group of subjects suffering from MDD; selecting a group of non-MDD subjects; and identifying the one or more markers/measures of retinal function, for example ERG parameters, that permit to discriminate between the subjects suffering from MDD and the non-MDD subjects.

In another aspect, the present invention provides a method for determining whether a subject suffers from or is predisposed to suffering from schizophrenia (SZ) or major depression (MDD), said method comprising (a) measuring one or more markers/measures of retinal function, for example ERG parameters, in the subject, in an embodiment one or more of the following ERG parameters: the cone a-Wave amplitude, the cone a-Wave implicit time, the cone b-Wave amplitude, the cone b-Wave implicit time, the rod a-Wave amplitude, the rod a-Wave implicit time, the rod b-Wave amplitude and the rod b-Wave implicit time, in the subject; (b) calculating an SZ or MDD probability score by adjusting the value of one or more of the markers/measures of retinal function, for example ERG parameters, by one or more transformation analyses; and (c) determining whether the subject suffers from SZ or MDD or has a predisposition thereto based on said SZ or MDD probability score. In another aspect, the present invention provides a method for determining whether a subject suffers from or is predisposed to suffering from schizophrenia (SZ) or major depression (MDD), said method comprising (a) calculating an SZ or MDD probability score by adjusting the value of one or more markers/measures of retinal function, for example ERG parameters, by one or more transformation analyses; and (b) determining whether the subject suffers from SZ or MDD or has a predisposition thereto based on said SZ or MDD probability score. In an embodiment, at least two ERG parameters are used to calculate the SZ or MDD probability score.

In another aspect, the present invention provides a method for identifying one or more markers/measures of retinal function, for example ERG parameters, useful for the differential diagnosis of SZ and MDD or of a predisposition thereto, said method comprising: selecting a group of subjects suffering from SZ; selecting a group of subjects suffering from MDD; measuring one or more markers/measures of retinal function, for example ERG parameters, in the subjects; and identifying the one or more markers/measures of retinal function, for example ERG parameters, that permit to discriminate between the subjects suffering from SZ and those suffering from MDD. In another aspect, the present invention provides a method for identifying one or more markers/measures of retinal function, for example ERG parameters, useful for the differential diagnosis of SZ and MDD or of a predisposition thereto, said method comprising: selecting a group of subjects suffering from SZ; selecting a group of subjects suffering from MDD; and identifying the one or more markers/measures of retinal function, for example ERG parameters, that permit to discriminate between the subjects suffering from SZ and those suffering from MDD.

In another aspect, the present invention provides a method for determining whether a subject suffers from or is predisposed to suffering from bipolar disorder (BP) or major depression (MDD), said method comprising (a) measuring one or more markers/measures of retinal function, for example ERG parameters, in the subject, in an embodiment one or more of the following ERG parameters: the cone a-Wave amplitude, the cone a-Wave implicit time, the cone b-Wave amplitude, the cone b-Wave implicit time, the rod a-Wave amplitude, the rod a-Wave implicit time, the rod b-Wave amplitude and the rod b-Wave implicit time, in the subject; (b) calculating a BP or MDD probability score by adjusting the value of one or more of the markers/measures of retinal function, for example ERG parameters, by one or more transformation analyses; and (c) determining whether the subject suffers from BP or MDD or has a predisposition thereto based on said BP or MDD probability score. In another aspect, the present invention provides a method for determining whether a subject suffers from or is predisposed to suffering from bipolar disorder (BP) or major depression (MDD), said method comprising (a) calculating a BP or MDD probability score by adjusting the value of one or more markers/measures of retinal function, for example ERG parameters, by one or more transformation analyses; and (b) determining whether the subject suffers from BP or MDD or has a predisposition thereto based on said BP or MDD probability score. In an embodiment, at least two ERG parameters are used to calculate the BP or MDD probability score.

In another aspect, the present invention provides a method for identifying one or more ERG parameters useful for the differential diagnosis of BP and MDD or of a predisposition thereto, said method comprising: selecting a group of subjects suffering from BP; selecting a group of subjects suffering from MDD; measuring one or more markers/measures of retinal function, for example ERG parameters, in the subjects; and identifying the one or more markers/measures of retinal function, for example ERG parameters, that permit to discriminate between the subjects suffering from BP and those suffering from MDD.

In another aspect, the present invention provides a method for stratification of a subject suffering from SZ, said method comprising measuring markers/measures of retinal function, for example the following ERG parameters (i) the cone b-wave implicit time, (ii) the rod a-wave implicit time, (iii) the rod b-wave amplitude, (iv) the cone a-wave amplitude, (v) the cone a-wave implicit time, and (vi) the rod b-wave implicit time, in said subject, wherein: (a) a rod a-wave implicit time, a cone a-wave implicit time and/or rod b-wave implicit time that is/are lower relative to the corresponding value(s) in a control subject defines a first group of stratification; (b) a rod b-wave implicit time that is higher relative to the corresponding value in a control subject defines a second group of stratification; (c) a cone b-wave implicit time that is higher and a rod b-wave implicit time that is similar relative to the corresponding values in a control subject defines a third group of stratification; (d) a cone b-wave implicit time that is substantially similar relative to the corresponding value in a control subject defines a fourth group of stratification. In another aspect, the present invention provides a method for stratification of a subject suffering from SZ, said method comprising analysing the values corresponding to (i) the cone b-wave implicit time, (ii) the rod a-wave implicit time, (iii) the rod b-wave amplitude, (iv) the cone a-wave amplitude, (v) the cone a-wave implicit time, and (vi) the rod b-wave implicit time, from said subject, wherein: (a) a rod a-wave implicit time, a cone a-wave implicit time and/or rod b-wave implicit time that is/are lower relative to the corresponding value(s) in a control subject defines a first group of stratification; (b) a rod b-wave implicit time that is higher relative to the corresponding value in a control subject defines a second group of stratification; (c) a cone b-wave implicit time that is higher and a rod b-wave implicit time that is similar relative to the corresponding values in a control subject defines a third group of stratification; (d) a cone b-wave implicit time that is substantially similar relative to the corresponding value in a control subject defines a fourth group of stratification.

In another aspect, the present invention provides a method for stratification of a subject suffering from BP, said method comprising measuring markers/measures of retinal function, for example the following ERG parameters: (i) the cone b-wave implicit time, (ii) the rod a-wave implicit time, (iii) the rod b-wave amplitude, (iv) the cone a-wave amplitude, (v) the cone a-wave implicit time, and (vi) the rod b-wave implicit time and/or (vii) the cone b-wave amplitude, in said subject, wherein: (a) a rod b-wave amplitude, a cone a-wave amplitude and/or a cone b-wave amplitude that is/are lower (e.g., less than about 0.5 SD or 1SD), and/or a rod a-wave implicit time that is higher (more than about 0.5, 1 or 1.5SD) relative to the corresponding value(s) in a control subject (not suffering from a major psychiatric disorder, e.g., BP) defines a first group of stratification; (b) a rod a-wave implicit time that is lower (e.g., less than about 0.5SD) relative to the corresponding value in a control subject defines a second group of stratification. In another aspect, the present invention provides a method for stratification of a subject suffering from BP, said method comprising analysing the values corresponding to (i) the cone b-wave implicit time, (ii) the rod a-wave implicit time, (iii) the rod b-wave amplitude, (iv) the cone a-wave amplitude, (v) the cone a-wave implicit time, and (vi) the rod b-wave implicit time and/or (vii) the cone b-wave amplitude, from said subject, wherein: (a) a rod b-wave amplitude, a cone a-wave amplitude and/or a cone b-wave amplitude that is/are lower (e.g., less than about 0.5 SD or 1SD), and/or a rod a-wave implicit time that is higher (more than about 0.5, 1 or 1.5SD) relative to the corresponding value(s) in a control subject (not suffering from a major psychiatric disorder, e.g., BP) defines a first group of stratification; (b) a rod a-wave implicit time that is lower (e.g., less than about 0.5SD) relative to the corresponding value in a control subject defines a second group of stratification.

In another aspect, the present invention provides a method of monitoring the response to a treatment in subject suffering from a major psychiatric disorder, said method comprising: (a) measuring one or more markers/measures of retinal function, for example ERG parameters, in the subject at a first, earlier time point and at a second, later time point, wherein said subject is treated between said first and second time points; (b) calculating major psychiatric disorder probability scores at said first and second time points by adjusting the value of one or more of the markers/measures of retinal function, for example ERG parameters, by one or more transformation analyses; (c) monitoring the response to the treatment in the subject based on the major psychiatric disorder probability scores at said first and second time points. In another aspect, the present invention provides a method of monitoring the response to a treatment in subject suffering from a major psychiatric disorder, said method comprising: (a) calculating major psychiatric disorder probability scores at a first, earlier time point and at a second, later time point by adjusting the value of one or more of the markers/measures of retinal function, for example ERG parameters, by one or more transformation analyses; (b) monitoring the response to the treatment in the subject based on the major psychiatric disorder probability scores at said first and second time points.

In another aspect, the present invention provides a method of monitoring the condition of a subject suffering from a major psychiatric disorder, said method comprising: (a) measuring one or more markers/measures of retinal function, for example ERG parameters, in the subject at a first, earlier time point and at a second, later time point; (b) calculating major psychiatric disorder probability scores at said first and second time points by adjusting the value of one or more of the markers/measures of retinal function, for example ERG parameters, by one or more transformation analyses; (c) monitoring the condition the subject based on the major psychiatric disorder probability scores at said first and second time points. In another aspect, the present invention provides a method of monitoring the condition of a subject suffering from a major psychiatric disorder, said method comprising: (a) calculating major psychiatric disorder probability scores at a first, earlier time point and at a second, later time point by adjusting the value of one or more of the markers/measures of retinal function, for example ERG parameters, by one or more transformation analyses; (b) monitoring the condition the subject based on the major psychiatric disorder probability scores at said first and second time points.

In another aspect, the present invention provides a program storage device readable by an electronic medium and tangibly storing instructions executable by the electronic medium to perform the one or more transformation analyses defined herein.

In another aspect, the present invention provides a computer program product comprising a computer useable medium that tangibly stores as computer readable code instructions to perform the one or more transformation analyses defined herein.

In another aspect, the present invention provides a system for performing the one or more transformation analyses defined herein, said system comprising: (a) a data acquisition module configured to produce a data set comprising one or more markers/measures of retinal function value(s), for example ERG parameter value(s); (b) a data processing module configured to process the data set by applying one or more transformation analyses to the data set to produce a statistically derived probability score; and (c) a display module configured to display the statistically derived probability score.

In an embodiment, the one or more transformation analyses comprise (i) adjusting the value of the one or more of the markers/measures of retinal function, for example ERG parameters, by appropriate weighting coefficients to produce a weighted score for each value (ERG value), and (ii) combining the weighted score for each value (ERG value) to generate the probability score.

In a further embodiment, the one or more transformation analyses comprise applying the value of the one or more of the markers/measures of retinal function, for example ERG parameters, to a pre-determined logistic regression model.

In a further embodiment, the logistic regression model was determined using markers/measures of retinal function values, for example ERG parameter values measured in a first population of subjects and a second population of subjects, wherein said first and second population of subjects differ by at least one characteristics.

In an embodiment, the logistic regression model includes age, gender, or both age and gender, as covariate(s), in a further embodiment it includes both age and gender as covariates.

Other objects, advantages and features of the present invention will become more apparent upon reading of the following non-restrictive description of specific embodiments thereof, given by way of example only with reference to the accompanying drawings.

DISCLOSURE OF INVENTION

Figure 1:
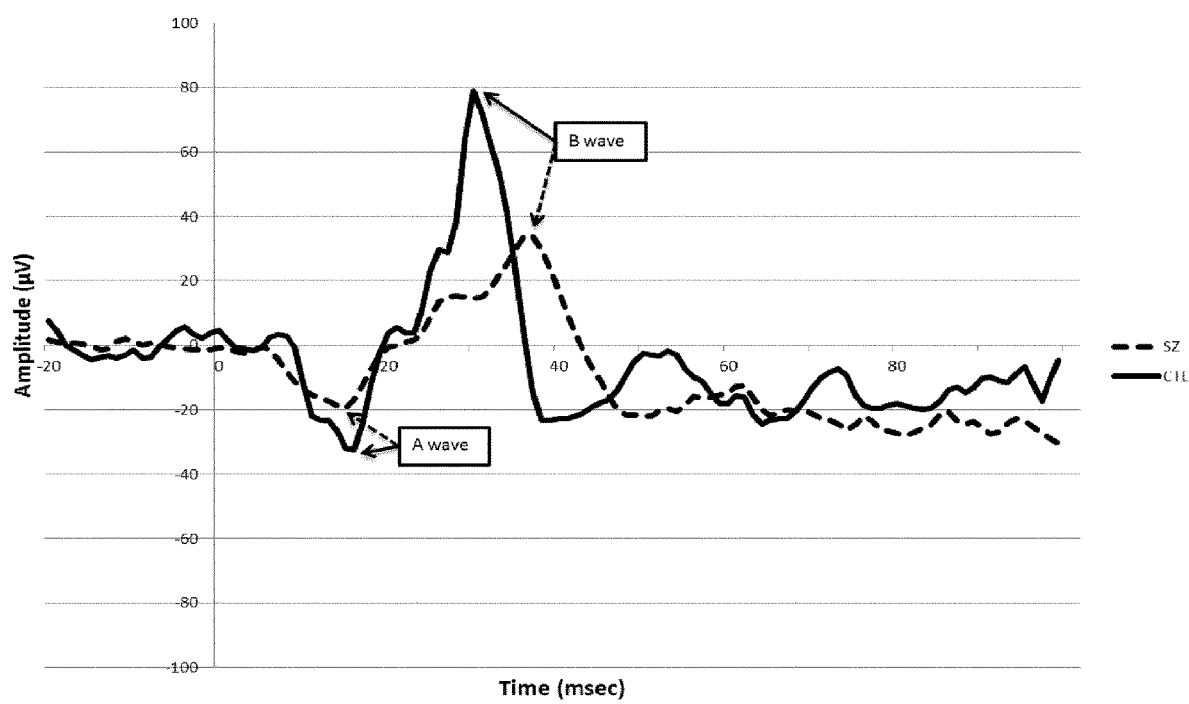
FIG. 1 shows the ERG response to a flash intensity that evokes a maximal response b-wave amplitude. The full line represents a typical response of a control participant (CTL), while the dotted line represents a typical response of a subject affected by schizophrenia (SZ).

In the studies described herein, the present inventors have shown that the assessment of markers/measures of the retinal function, and more particularly electroretinography (ERG) parameters, is useful for the screening, diagnosis, differential diagnosis, prognosis (predisposition or susceptibility), monitoring and/or stratification, prediction of pharmacological response and pharmacodynamics, in patients afflicted by psychiatric disorders, such as SZ, BP and MDD. More specifically, the present inventors have shown that performing one or more transformation analysis (statistical analysis such as logistic regression analysis) of ERG parameter value(s), it is possible to identify/determine specific ERG parameter signatures that are associated with, for example, different psychiatric disorders (and to a predisposition thereto), such as SZ, BP and MDD, with good or poor/intermediate response to medication (pharmacological response) of patients with psychiatric disorders, or with groups of patients (strata) with shared biological characteristics.

Definitions

As used herein, the term "diagnosis" as used herein encompasses identification, confirmation, and/or characterization of a disease (psychiatric disorder), or predisposition/susceptibility thereto. By "predisposition" or "susceptibility", it is meant that a subject does not currently present with the disorder, but is liable to be affected by the disorder in time. It refers to the likelihood to develop, or to suffer from, a disorder or disease. An individual with a predisposition or susceptibility to a disorder or disease is more likely to develop, or to suffer from, the disorder or disease than an individual without the predisposition or susceptibility to the disorder or disease, or is more likely to develop, or to suffer from, the disorder or disease than members of a relevant general population under a given set of environmental conditions (diet, physical activity regime, geographic location, etc.).

As used herein, the term "screening" refers to the detection of a particular mental disorder at an early stage or to identify a patient who are suspected of having a particular mental disorder but that are asymptomatic (no significant signs and symptoms) (e.g., patients with family history).

As used herein, the term "prognostic" refers to the determination of the degree of risk of a particular mental disorder occurrence or progression.

As used herein, the term "differential diagnosis" refers to the identification of a particular mental disorder or condition in cases where multiple alternatives are possible, and may be used to confirm a clinical diagnosis that a patient has a mental disease (i.e. during an active or a stabilized phase), or to distinguish between different types of mental diseases.

As used herein, the term "prediction" refers to the determination of whether a given patient is likely to respond to drug treatments (good responders and poor or non-responders), i.e. to identify the best treatment options.

As used herein, the term "pharmacodynamics" refers to the study of the biochemical and physiological effects of a drug on the body, i.e. to determine if a biological response has occurred in a patient after treatment with a particular drug treatment.

As used herein, the term "monitoring" refers to the assessment of the condition of a subject suffering from a major psychiatric disorder or short and long term response to a particular drug treatment.

As used herein, the term "stratification" refers to the identification of different groups of patients (strata) with shared biological characteristics based on their biomarkers (ERG parameters) in order to select the optimal management and to achieve the best possible outcome in term of risk assessment and prevention, achievement of the optimal medical intervention.

As used herein, the term "subject" means an individual. In an embodiment, the subject is a human. As used herein, a "subject" is the same as a "patient," and the terms can be used interchangeably. In an embodiment, the subject is suspected of suffering from, or of having a predisposition to, the psychiatric disorder.

As used herein, the term "psychiatric disorders" refers to mental disorder or illness that interferes with the way a person behaves, interacts with others, and functions in daily life, and includes any appropriate psychiatric disorder according to DSM-IV Diagnostic and Statistical Manual of Mental Disorders, 4th edition, American Psychiatric Assoc., Washington, D.C., 2000 or DSM-V Diagnostic and Statistical Manual of Mental Disorders, 5th edition, American Psychiatric Assoc., Washington, D.C., 2013, for example: mood disorders such as depression, major depressive disorder (MDD), seasonal affective disorder (SAD), treatment-resistant depression, mania, cyclothymic disorder and bipolar disorders (including bipolar disorder in manic, depressive and euthymic phases); anxiety disorders such as generalized anxiety disorder, obsessive-compulsive disorder (OCD), panic attacks and panic disorder, phobic disorders, stress disorders; dissociative disorders such as depersonalization disorder, dissociative amnesia, dissociative fugue, dissociative identity disorder; drug use and dependence; eating disorders such as anorexia nervosa, binge eating disorder and bulimia nervosa; personality disorders; sexuality and sexual disorders such as gender identity disorder and transsexualism and paraphilias; somatoform; factitious disorders such as body dysmorphic disorder, conversion disorder, hypochondriasis, Munchausen syndrome, pain disorder and somatization disorder; Asperger syndrome or suicidal behavior; psychotic disorders such as schizophrenia, delusional disorder, schizoeffective disorder and schizophreniform disorder.

The term "probability score" as used herein refers to a number for an individual subject that is determined using an algorithm for providing assessment of a specific outcome (e.g., clinical outcome), for example diagnosis of a psychiatric disease (e.g., SZ, BP, MDD), differential diagnosis (e.g., SZ vs. BP), prediction of a response to treatment, etc. In an embodiment, the probability score will be determined using logistical regression and will be a number between 0 and 1. Such an algorithm would have the following formula:

$$\text{probability score} = \text{Exp}(b_0 + b_a \cdot x_a + b_g \cdot x_g + b_1 \cdot x_1 + \ldots + b_n \cdot x_n) / [1 + \text{Exp}(b_0 + b_a \cdot x_a + b_g \cdot x_g + b_1 \cdot x_1 + \ldots + b_n \cdot x_n)],$$

wherein $b_0$ is an intercept value;
$b_a$ is the regression coefficient of the age covariate;
$x_a$ is the age value;
$b_g$ is the regression coefficient of the gender covariate;
$x_g$ is the gender value (taking 1 if the subject is a female and 0 if the subject is a male);
$b_1$ is the regression coefficient of the first marker (e.g, a first ERG parameter);
$x_1$ is the value measured for the first marker (e.g, the first ERG parameter);
$b_n$ is the regression coefficient of the $n^{th}$ marker (e.g, the $n^{th}$ ERG parameter); and
$x_n$ is the value measured for the $n^{th}$ marker (e.g, the $n^{th}$ ERG parameter).

Throughout the present specification, several algorithm formulas are provided. It will be understood that intercept value and the regression coefficients have been determined based on the specific group of subjects studied, and that these algorithm formulas and/or values may vary. Accordingly, in an embodiment, in the algorithm formulas described herein, the intercept value and the regression coefficients may vary for example within the ranges defined by the 95% confidence intervals (95% CI) set forth in the Tables below. In another embodiment, the values may vary by about 30% or less, 20% or less, in an embodiment by about 10% or 5% or less. Thus, it would be clearly understood by the skilled person that the present invention encompasses the use of any algorithm formulas or models identified according to the method described herein for the screening, diagnosis, differential diagnosis, prognosis (predisposition or susceptibility), monitoring and/or stratification, prediction of pharmacological response and pharmacodynamics, in patients afflicted by psychiatric disorders.

As used herein, the term "markers/measures of retinal function" includes any measurable/detectable parameters of the function of the retina, such as the electrical response, and includes markers/measured obtained by tests for evaluation of retinal function such as Amsler Grid test, Colour Vision Testing, Electroretinography (ERG), including multifocal ERG (mERG), full-field ERG (ffERG), pattern ERG (pERG), electrooculography (EOG). Accordingly, the present invention relates to the use of any marker/measure, or any combination of markers/measures, of the function of the retina, in the methods described herein. In an embodiment, the markers/measures of retinal function are ERG parameters.

Electroretinography (ERG) in the Assessment of Psychiatric Disorders

There is no reliable diagnostic test, and more particularly biological diagnostic test (based on biomarkers, for example), for psychiatric disorders. The present inventors have discovered that specific electroretinography (ERG) parameters (flash ERG parameters), when used alone or in combination, or when such parameters are processed using specific algorithms, can be used as biomarkers for the diagnosis, screening, prognosis (predisposition or susceptibility), differential diagnosis, monitoring and stratification of patients afflicted by such disorders, as well as for to the prediction of pharmacological response in patients afflicted by such disorders. The present invention may thus allow to confirm diagnosis and/or reducing misdiagnosis of psychiatric disorders or to select the most appropriate medical intervention for patient afflicted from psychiatric disorders, to screen patients or to predict their risk of suffering or developing the disorder or to stratify them.

Physiology of ERG

The neural part of the eye, namely the retina, is responsible for transforming light into chemical and electrical signals that will lead to nerve impulses sent, for the most part, to various visual centers of the brain to generate the sense of vision. In darkness, photoreceptors are depolarized and release Glutamate continuously. In response to light, retinal photoreceptors hyperpolarize, yielding to a decrease in Glutamate release. This decrease in Glutamate will in turn stimulate ON bipolar cells followed by ON ganglion cells. Ganglion cells generate action potentials (nerve impulses) that are sent through the optic nerve to the visual centers of the brain for the most part.

The ERG light-evoked potential recorded at the surface of the eyes allows the assessment of the photoreceptor and bipolar cells circuit only. The typical waveform is composed first of a small negative component known as the a-wave, followed by a larger positive component known as the b-wave. The a-wave amplitude is measured from baseline (pre-stimulus) to the trough of the response, whereas the b-wave is measured from the trough of the a-wave to the peak of the b-wave. Peak latencies (both a- and b-waves) are measured from flash onset. The negative a-wave is generated for the most part by the photoreceptors whereas the b-wave, is generated by the bipolar and Müller (glia cells) cells complex.

There are two types of photoreceptors in the eye, the cones responsible for visual acuity, color and day vision and the rods, responsible of black and white night vision. Depending on the protocol used, it is possible to assess cones and rods functions separately by changing the state of adaptation of the retina. In light adapted retina (for instance in normal room light), with relatively bright flashes, only cones will contribute to the so-called "photopic ERG" (ph) since the very sensitive rods are saturated in normal room light condition. Following a proper dark adaptation period (of at least about 20 min) and using below cone threshold light flashes, only rods will be recorded in the so-called "scotopic ERG" (sc). However, with brighter flashes, both cones and rods will contribute to the scotopic response. Since rods outnumber cones by a factor close to 20, the mixed scotopic response is still dominated by rods.

Although a single flash intensity can provide some important information regarding the integrity of the cones or rods functions, more information can be derived with the used of various flash intensities that allow the generation of the luminance response function. The photopic and scotopic luminance response functions are quite different. Typically, the b-wave amplitude increases with increasing flash intensities until a maximum response is achieved. In the photopic ERG, after reaching the peak maximal response (known as the Vmax), the response will decrease with brighter flashes until a plateau is reach. This phenomenon known as the photopic hill is still unclear although it is believe that the cone OFF bipolar cells (those that hyperpolarize in the light and depolarize in the dark) could be implicated. In contrast, the scotopic luminance response function adopts a different shape, with rods amplitude increasing with flash intensities until a first plateau is observed. With brighter flashes, sufficiently high to trigger the cones, a second plateau will be observed.

Since a luminance response function was produced in the protocol, it was possible to detect the maximal amplitude (called Vmax) observed both for the cones and the rods. More precisely, for the cone function, the Vmax correspond to the maximal response of the photopic hill. The photopic hill is also characterized with fixed intensities such as intensity 7.5 cd·s/m$^2$ ("int1" in Tables) and an average of the response at three intensities (13.33, 23.71 and 50 cd·s/m$^2$) referred to as "3-int" in the different tables. For the rod function (scotopic), the Vmax refer to the saturating amplitude observed at the 0.1 cd·s/m$^2$ intensity, where rods only are involved in the response (referred to as "Vmax" in Tables). The response at a higher intensity, where both cones and rods are then involved is also recorded (flash intensity of 1 cd·s/m$^2$ referred to as "int2" in Tables). Another parameter can be derived, namely the log K parameter which is interpreted as retinal sensitivity. The log K parameter is derived following the sigmoid curve fitting of the luminance response curve up to the Vmax and corresponds to the intensity necessary to reach one half the Vmax. In summary, various parameters can be measured from the ERG such as: log K, a- and b-waves amplitudes (including the maximal amplitude, Vmax) and latencies (i.e., implicit times of both the a-wave and b-wave).

The ERG can be recorded several ways. The pupil is usually dilated to better stimulate the entire retina but the ERG can also be recorded undilated using brighter flashes. There are a number of corneal ERG electrodes that are in common use. Some are speculum structures that hold the eye open and have a contact lens with a wire ring that "floats" on the cornea supported by a small spring. Some versions use carbon, wire or gold foil to record electrical activity. There are also cotton wick electrodes. There are yet other simpler ERG recording devices using gold Mylar tape that can be inserted between the lower lid and sclera/cornea. Most electrodes are monopolar, i.e., are referred to another electrode site most commonly on the forehead or lateral canthus. Some are bipolar with the reference electrodes built into a metal surface on a speculum. The ERG can also be recorded using skin electrodes placed just above and below the eye, or below the eye and next to the lateral canthus. Since skin electrodes are not in direct contact with the eye leading to a significant attenuation in amplitude of the ERG, so a higher number of individual responses to flash stimulation are usually averaged by computer.

There are also several methods of stimulating the eye. It is possible to use a strobe lamp that is mobile and can be placed in front of a person whether sitting or reclining. Ganzfeld (globe) with a chin rest and fixation points are often used (e.g., Colordome™ and Espion™ Visual Electrophysiology System from Diagnosys LLC, Veris Compact™ from Electro-Diagnostic Imaging Inc, MonPack™ and MonColor™ from Metrovision).

Either strobe lamp or Ganzfeld methods of flash presentation can be used to record the ERG following a single flash or to average responses to several flashes with the aid of a computer.

In a first aspect, the present invention provides a method for the diagnosis, screening, prognosis, differential diagnosis, prediction, pharmacodynamic, monitoring and stratification of a psychiatric disorder (e.g. a major psychiatric disorder), said method including the following steps:

a) Measuring one or more ERG parameters in a patient, for example one or more of the following ERG parameters:
Cone a-wave amplitude;
Cone a-wave implicit time;
Cone b-wave amplitude;
Cone b-wave implicit time;
Rod a-wave amplitude;
Rod a-wave implicit time;
Rod b-wave amplitude;
Rod b-wave implicit time;
Log K and/or
Vmax b) Comparing the measured ERG parameter(s) with corresponding reference (normal subjects) or other related diseases, and/or optionally processing specific ERG parameter(s) with appropriate algorithms (i.e. the algorithms/models defined herein or obtained by the methods for identifying a model as defined herein) for the diagnosis, screening, prognosis, differential diagnosis, prediction, pharmacodynamics, monitoring and stratification of a psychiatric disorder In an embodiment, the psychiatric disorder is a major psychiatric disorder, such as schizophrenia (SZ), bipolar disorder (BP) or major depressive disorder (MDD). In an embodiment, the psychiatric disorder is SZ.

There are different phases of major psychiatric disorders (e.g., SZ): prodromal (or beginning), active, and stabilized. They tend to occur in sequence and appear in cycles throughout the course of the illness.

Prodromal Phase:

The first stage is called the prodromal stage and refers to the year before the illness appears. During the prodromal phase, symptoms develop gradually. This phase is typically characterized by the lost of interest in usual pursuits and withdrawal from friends and family members. During this phase, the subjects may become easily confused, have trouble concentrating, and feel listless and apathetic, preferring to spend most of their days alone. Occasionally, these symptoms reach a plateau and do not develop further but, in most cases, an active phase of the illness follows. The prodromal period can last weeks or months.

Active Phase:

Active (or acute) phase in SZ is typically characterized by delusions, hallucinations, marked distortions in thinking and disturbances in behaviour and feelings. This phase most often appears after a prodromal period. On occasion, these symptoms can appear suddenly. Patients in the active phase of schizophrenia often need antipsychotic medication to alleviate their symptoms.

Stabilized Phase:

After an active phase, subject may have an improvement of active symptoms, present a degree of improvement in social adaptation. Patients in this stage do not appear psychotic but may experience some negative symptoms such as lack of emotional expression or low energy and a degree of social difficulties.

In an embodiment, the methods disclosed herein are performed during the prodromal (or beginning) phase of the major psychiatric disorder (e.g., SZ). In another embodiment, the methods disclosed herein are performed during the active phase of the major psychiatric disorder (e.g., SZ). In another embodiment, the methods disclosed herein are performed during the active phase of the major psychiatric disorder (e.g., SZ) and after the subject has been treated using antipsychotic medication to alleviate their symptoms.

In another embodiment, the above-mentioned method is performed during the stabilized phase of the major psychiatric disorder (e.g., SZ).

In another embodiment, the methods disclosed herein are performed on a subject that is at risk (e.g., based on family antecedents, genetic factors and/or other risk factors, for example) of developing a major psychiatric disorder (e.g., SZ).

Methods of monitoring and of diagnosis according to the invention are useful to confirm the existence of a disorder, or predisposition thereto; to monitor development of the disorder by assessing onset and progression, or to assess amelioration or regression of the disorder. Methods of monitoring and of diagnosis according to the invention are also useful as drug development tools (e.g., for patient screening, evaluation of therapeutic benefits in clinical studies) or as companion diagnostic test for psychotropic drugs.

Identification of Models Based on ERG Profiles that Permit to Discriminate Between Groups of Subjects In the studies described herein, the present inventors have developed models (algorithms) based on flash ERG parameters that permits to distinguish with good accuracy, sensitivity and specificity patients suffering from psychiatric disorders (SZ, BP, MDD), psychiatric patients' response to treatments, and psychiatric patients' clinical or cognitive features.

Accordingly, in an aspect, the present invention provides a method of identifying a model, based on one or more ERG parameters, that permits to discriminate between a first group of subjects and a second group of subjects that differ by at least one characteristics, wherein said first group and/or second group of subjects suffer from a psychiatric disorder or a has a predisposition thereto, said method comprising:

(a) measuring a plurality of ERG parameters in said subjects;

(b) performing a logistic regression analysis using the plurality of ERG parameters measured to identify a model that permits to discriminate between the first group and the second group of subjects.

In an embodiment, the age and/or gender are included as covariate(s) in the logistic regression analysis.

Discriminate as used herein means that the model is suitable to calculate a probability or likelihood that a test subject belongs to the first group or the second group (i.e. has the at least one characteristics of the first or second group).

The at least one characteristics that differ between the two groups, may be, for example, the presence vs. absence of a psychiatric disorder or a predisposition thereto (e.g., SZ, BP or MDD subjects vs. non-affected subjects), the type of psychiatric disorder or predisposition thereto (e.g., SZ vs. BP, SZ vs. MDD, BP vs. MDD), the response to psychotropic medication (e.g., good vs. poor responders), the social, occupational, and psychological functioning of the subjects (e.g., subjects with high vs. low scores on the GAS scale or PANSS), or any other characteristic (e.g., mental, physical, clinical, medical or pharmacological characteristics) that differs between a first group of subjects and a second group of subjects.

In an embodiment, the at least one characteristics comprises the type of psychiatric disorder or predisposition thereto, and wherein the first group of subjects suffer from a first psychiatric disorder or has a predisposition thereto and said second group of subjects suffer from a second psychiatric disorder or has a predisposition thereto. In another embodiment, the at least one characteristics comprises the presence or absence of the psychiatric disorder or predisposition thereto, and wherein said first group of subjects suffer from a psychiatric disorder or has a predisposition thereto and said second group of subjects do not suffer from a psychiatric disorder or do not have a predisposition thereto. In another embodiment, the at least one characteristics comprises the response to a psychotropic medication, and wherein said first group of subjects are good responders to a psychotropic medication and said second group of subjects are poor responders to said psychotropic medication. In an embodiment, the psychotropic medication is an antipsychotic medication or a mood stabilizer medication. In a further embodiment, the psychotropic medication comprises quetiapine, aripiprazole, olanzapine, lithium or clozapine.

In an embodiment, the logistic regression analysis is multiple stepwise logistic regression analysis. In an embodiment, both age and gender are included as covariate in said logistic regression analysis.

In an embodiment, the method comprises measuring at least 2 ERG parameters. In another embodiment, the method comprises measuring at least 3 ERG parameters. In another embodiment, the method comprises measuring at least 4 ERG parameters. In another embodiment, the method comprises measuring at least 5 ERG parameters. In another embodiment, the method comprises measuring at least 6 ERG parameters. In another embodiment, the method comprises measuring at least 7 ERG parameters. In another embodiment, the method comprises measuring at least 8 ERG parameters.

In an embodiment, the one or more ERG parameters are flash ERG parameters. In a further embodiment, the ERG parameters measured are the cone a-Wave amplitude (phAamp), the cone a-Wave implicit time (phAlat), the cone b-Wave amplitude (phBamp), the cone b-Wave implicit time (phBlat), the rod a-Wave amplitude (scAamp), the rod a-Wave implicit time (scAlat), rod b-Wave amplitude (scBamp), the rod b-Wave implicit time (scBlat), the Log K and/or the Vmax. In another embodiment, the ERG parameters measured are the cone a-Wave amplitude (phAamp), the cone a-Wave implicit time (phAlat), the cone b-Wave amplitude (phBamp), the cone b-Wave implicit time (phBlat), the rod a-Wave amplitude (scAamp), the rod a-Wave implicit time (scAlat), rod b-Wave amplitude (scBamp) and/or the rod b-Wave implicit time (scBlat). In another embodiment, the ERG parameters measured are the cone a-Wave amplitude (phAamp), the cone a-Wave implicit time (phAlat), the cone b-Wave amplitude (phBamp), the cone b-Wave implicit time (phBlat), the rod a-Wave amplitude (scAamp), the rod a-Wave implicit time (scAlat), rod b-Wave amplitude (scBamp) and the rod b-Wave implicit time (scBlat).

In an embodiment, the method further comprises determining the accuracy, sensitivity and/or specificity of the model. The overall assessment of the accuracy of the model may be obtained, for example, by calculating the Area Under the Receiver Operating Curve (AU-ROC). The fitted model provided, for each subject, the logit of the probability to belong to one of the two groups in the comparison and a cut-off value (e.g., 0.5, 0.6, 0.7 or 0.8) on this probability determined the predicted group membership for this subject. Then a 2×2 table may be obtained by crossing the predicted group membership with the true one. Estimates of the sensitivity and specificity of the regression model may be obtained from the 2×2 table by calculating the proportion of subjects from the first and second groups that were correctly classified. A corresponding odds ratio (OR) may also be calculated from the 2×2 table as a measure of the strength of the association between the predicted and true group membership. Given that an OR value of 1 represents an absence of association (or relatedness) between the predicted and observed group membership, values greater than 1 rather suggest that the predicted group membership is often accurate, i.e. predicting the true group membership. Theoretically, OR takes values ranging from 0 to ∞, the higher values revealing stronger relatedness.

The model may take the form of an algorithm for providing assessment of a specific outcome (e.g., clinical outcome), as explained above. Such an algorithm may have the following formula, in an embodiment in which the age and gender are included as covariates:

$$\text{probability score} = \text{Exp}(b_0 + b_a * x_a + b_g * x_g + b_1 * x_1 + \ldots + b_n * x_n) / [1 + \text{Exp}(b_0 + b_a * x_a + b_g * x_g + b_1 * x_1 + \ldots + b_n * x_n)],$$

wherein
$b_0$ is an intercept value;
$b_a$ is the regression coefficient of the age covariate;
$x_a$ is the age value;
$b_g$ is the regression coefficient of the gender covariate;
$x_g$ is the gender value (taking 1 if the subject is a female and 0 if the subject is a male);
$b_1$ is the regression coefficient of the first marker (e.g, a first ERG parameter);
$x_1$ is the value measured for the first marker (e.g, the first ERG parameter);
$b_0$ is the regression coefficient of the $n^{th}$ marker (e.g, the $n^{th}$ ERG parameter); and
$x_n$ is the value measured for the $n^{th}$ marker (e.g, the $n^{th}$ ERG parameter).

Having identified a model that provides an estimate of the likelihood or probability to belong to a first or second group, it is thus possible to use the model to estimate of the likelihood or probability that a test subject (a subject undergoing diagnosis for a psychiatric disorder) belongs to the first group (e.g., suffers from a given psychiatric disorder, such as SZ) or to the second group (does not suffer from the psychiatric disorder (SZ), or suffers from a different psychiatric disorder (e.g., BP). Accordingly, in another aspect, the present invention provides method of determining the likelihood that a test subject belongs to a first group of subjects or a second group of subjects that differ by at least one characteristics, said method comprising
(a) measuring at least one ERG parameter in said test subject;
(b) analysing the at least one ERG parameter measured using the model identified by the method defined above to determine the likelihood that the test subject belongs to the first group or second group of subjects.

Diagnosis of Psychiatric Disorders

In the studies described herein, the present inventors have shown that certain ERG parameters (individual ERG parameters and/or combination thereof) permit to distinguish patients suffering from psychiatric disorders (SZ, BP, MDD) from healthy subjects (i.e. not suffering from psychiatric disorders). Thus, in an aspect, the present invention provides the use of any of the ERG parameters showing statistical significance (e.g., p<0.05, 0.01, 0.005 or preferably 0.001) identified by the univariate analyses described in the Example below (see, e.g., Tables 2, 8, 10, 13, 15) for the diagnosis of psychiatric disorders.

Accordingly, in an aspect, the present invention provides a method for determining whether a subject suffers from schizophrenia (SZ) or has a predisposition thereto, said method comprises measuring at least (i) the cone b-wave implicit time, and/or (ii) the cone b-wave amplitude, in the subject, and wherein (a) a cone b-wave implicit time that is higher, and/or a cone b-wave amplitude that is lower, relative to the corresponding parameter(s) measured in a control subject not suffering from SZ; or (b) a cone b-wave implicit time that is substantially similar or higher, and/or a cone b-wave amplitude that is substantially similar or lower, relative to the corresponding parameter(s) measured in a control patient suffering from SZ, is indicative that said subject suffers from SZ or has a predisposition thereto.

In an embodiment, the method comprises measuring the cone b-wave implicit time. In another embodiment, the method comprises measuring the cone b-wave amplitude. In another embodiment, the method comprises measuring both the cone b-wave implicit time and the cone b-wave amplitude.

In an embodiment, the method further comprises measuring one or more of the following ERG parameters: (iii) the cone a-wave amplitude, (iv) the rod a-wave amplitude and/or (v) the rod b-wave amplitude, in the subject, and wherein (a) a cone a-wave amplitude, a rod a-wave amplitude and/or a rod b-wave amplitude that is lower, relative to the corresponding parameter(s) measured in a control subject not suffering from SZ, or (b) a cone a-wave amplitude, a rod a-wave amplitude and/or a rod b-wave amplitude that is substantially similar or lower, relative to the corresponding parameter(s) measured in a control patient suffering from SZ, is indicative that said subject suffers from SZ or has a predisposition to suffer from SZ.

In an embodiment, the method comprises measuring the (i) cone b-wave implicit time, (ii) the cone b-wave amplitude, or both the cone b-wave implicit time and the cone b-wave amplitude, with one or any combination of (iii) the cone a-wave amplitude, (iv) the rod a-wave amplitude and (v) the rod b-wave amplitude. For example, the method may comprise measuring parameters (i) and (iii); parameters (i), (ii) and (iii); parameters (i), (iii) and (iv); parameters (i), (ii), (iii) and (v); parameters (i) to (v), etc.

In an embodiment, the method comprises measuring one or more of the ERG parameters exhibiting statistically significant differences between SZ (5 years or less of disease duration) and CT, as assessed by univariate analysis, depicted in Table 13.

In another aspect, the present invention provides the use of one or more of the above-mentioned ERG parameters as biomarkers for the diagnosis of SZ, or of a predisposition thereto.

The ERG parameter values obtained in the subject being assessed may be compared to corresponding ERG parameter values (e.g., "control" or "reference" or "standard" values) measured/obtained in "control" subjects, which may be (1) subjects not suffering from the disease (e.g., SZ) or not at risk or predisposed to suffering from the disease ("healthy subjects"), or (2) patients suffering from the disease (e.g., SZ) or at risk of or predisposed to suffering from the disease (e.g., SZ). The corresponding control value may be a value corresponding to an average or median value calculated based of the values measured in several reference or control subjects (e.g., a pre-determined or established standard value). The control value may be a pre-determined "cut-off" value recognized in the art or established based on values measured in a group of control subjects. The corresponding reference/control value may be adjusted or normalized for age, gender, race, or other parameters. The control value can thus be a single number/value, equally applicable to every patient individually, or the control level can vary, according to specific subpopulations of patients (e.g., male, female).

Thus, for example, older men might have a different control value than younger men, and women might have a different control value than men. The predetermined standard value can be arranged, for example, where a tested population is divided equally (or unequally) into groups, such as a low-risk group, a medium-risk group and a high-risk group or into quadrants or quintiles, the lowest quadrant or quintile being individuals with the lowest risk (e.g., ERG parameter value(s) slightly diverging from those measured in "healthy" subjects) and the highest quadrant or quintile being individuals with the highest risk (i.e., e.g., ERG parameter value(s) greatly diverging from those measured in "healthy" subjects). It will also be understood that the control values according to the invention may be, in addition to predetermined values, ERG parameter values measured in other samples (e.g. from healthy/normal subjects, or patients) tested in parallel with the subject being assessed.

"Substantially similar" as used herein refers to a value that is not statistically different relative to the control value, for example a value that is within about ±0.2, 0.3, 0.4, 0.5, 0.6, 0.7, 0.8, 0.9 or 1.0 standard deviation (SD) relative to a control (mean) value obtained in control subjects.

"Higher" and "lower" refer to values that are statistically different relative to the control value, for example values that are more than about ±0.2, 0.3, 0.4, 0.5, 0.6, 0.7, 0.8, 0.9 or 1.0 SD (e.g., ±1.5SD, ±2SD, ±3SD), relative to a control (mean) value obtained in control subjects.

The skilled person would understand that this may vary from one parameter to another, and would be able to determine the "cut-off" suitable for determining whether a value is substantially similar to a control value, for example using an appropriate statistical test. For example, a parameter that is highly variable between subjects, a value within 1.0 SD may be considered substantially similar, whereas for a parameter that is only slightly variable between subjects, a value within 0.2 SD may be considered substantially similar. A statistical test such as an ANCOVA could provide an estimate of an effect size (characterizing the difference between an ERG value relative to the control value) that could be used to determine the appropriate "cut-off" suitable for a particular parameter.

In another aspect, the present invention provides a method for determining whether a subject suffers from bipolar disorder (BP) or has a predisposition thereto, said method comprises measuring at least (i) the cone a-wave implicit time, (ii) the cone b-wave implicit time, (iii) the rod a-wave amplitude, (iv) the rod a-wave implicit time, (v) the rod b-wave amplitude, and/or (vi) the log K, in the subject, wherein (a) a cone a-wave implicit time, a rod a-wave amplitude, a rod a-wave implicit time, and/or a rod b-wave amplitude, that is lower, and/or a cone b-wave implicit time, and/or a log K that is higher, relative to the corresponding parameter(s) measured in a control subject not suffering from BP, or (b) a cone a-wave implicit time, a rod a-wave amplitude, a rod a-wave implicit time, and/or a rod b-wave amplitude, that is substantially similar or lower, and/or a log K, and/or a cone b-wave implicit time that is substantially similar or higher, relative to the corresponding parameter(s) measured in a control patient suffering from BP, is indicative that said subject suffers from BP or has a predisposition thereto.

In an embodiment, the method comprises measuring (i) the cone a-wave implicit time. In another embodiment, the method comprises measuring (ii) the cone b-wave implicit time. In another embodiment, the method comprises measuring (iii) the rod a-wave amplitude. In another embodiment, the method comprises measuring (iv) the rod a-wave implicit time. In another embodiment, the method comprises measuring (v) the rod b-wave amplitude. In another embodiment, the method comprises measuring (vi) the log K. In another embodiment, the method comprises measuring any combinations of parameters (i) to (vi), for example (i) and (ii); (i) and (iv); (iii) and (iv); (i), (ii) and (iii); (i) to (iv), (i) to (vi), etc.

In another aspect, the present invention provides the use of one or more of the above-mentioned ERG parameters as biomarkers for the diagnosis of BP, or of a predisposition thereto.

In another aspect, the present invention provides a method for determining whether a subject suffers from major depressive disorder (MDD) or has a predisposition thereto, said method comprises measuring at least (i) the rod a-wave amplitude and/or (ii) the rod b-wave amplitude, in the subject, wherein (a) a rod a-wave amplitude, and/or a rod b-wave amplitude that is lower, relative to the corresponding parameter(s) measured in a control subject not suffering from MDD, or (b) a rod a-wave amplitude, and/or a rod b-wave amplitude that is substantially similar or lower, relative to the corresponding parameter(s) measured in a control patient suffering from MDD, is indicative that said subject suffers from MDD or has a predisposition thereto. In an embodiment, the method comprises measuring (i) the rod a-wave amplitude. In an embodiment, the method comprises measuring (ii) the rod b-wave amplitude. In another embodiment, the method comprises measuring (i) the rod a-wave amplitude and (ii) the rod b-wave amplitude.

In another aspect, the present invention provides the use of one or more of the above-mentioned ERG parameters as biomarkers for the diagnosis of MDD, or of a predisposition thereto.

In embodiments, the ERG values for one or more of the ERG parameters are subjected to one or more transformation analyses. As used herein, "transformation analyses" can be any suitable mathematical operation, including but not limited to generalized models (e.g., logistic or logit regression, ROC regression, generalized additive models), multivariate analysis (e.g., discriminant analysis, principal components analysis, factor analysis). In an embodiment, the one or more transformation analyses comprises logistic regression analysis, and in a further embodiment the logistic regression analysis comprises (i) adjusting the value of one or more of the ERG parameters by an appropriate weighting coefficient (e.g., regression coefficient) to produce a weighted score for each ERG value, and (ii) combining the weighted score for each ERG value to generate the probability score (e.g. the probability that the subject suffers from a psychiatric disease (e.g., SZ, BP) or has a predisposition thereto, etc.). In various embodiments, the levels of one, two, three, four, five, or more ERG values may be adjusted by an appropriate weighting coefficient. In an embodiment, the transformation analysis is performed using a suitable software, in a further embodiment the Statistical Analysis Software (SAS).

As will be understood by those of skill in the art based on the teachings herein, weighting coefficients can be determined by a variety of techniques and can vary widely. In one example of determining appropriate weighting coefficients, multiple logistic regression (MLR) is performed using the ERG parameters measured within two groups of patients, for example, one with a psychiatric disease (e.g., SZ) and one without the psychiatric disease. There are several methods for variable (ERG parameter) selection that can be used with MLR, whereby the ERG parameters not selected are eliminated from the model and the weighting coefficients for each predictive ERG parameter remaining in the model are determined. These weighting coefficients can then be, for example, multiplied by the ERG parameter value measured in the subject and then, for example, summed to calculate a probability score (e.g., the probability that the subject suffers from a psychiatric disease (e.g., SZ, BP) or has a predisposition thereto).

In an embodiment, the probability score is determined using a regression algorithm that includes other parameters/variables as covariate, in a further embodiment age, gender, or both age and gender.

In an embodiment, the cut-off probability score is 0.5, in further embodiment 0.55, 0.6, 0.65, 0.7, 0.75 or 0.8. The cut-off probability score is determine by the maximization of the sensitivity and specificity of the prediction obtained by the regression algorithm. As shown in Example 2 below (e.g., Table 3C), the sensitivity and specificity as well as OR may be significantly improved by using a more stringent cut-off probability score for predicting a subject in the SZ group (a cut-off probability score of 0.80 for classifying a subject as being SZ and a cut-off probability score of 0.20 for classifying a subject as being CT).

In another aspect, the present invention provides a method for determining whether a subject suffers from schizophrenia (SZ) or has a predisposition thereto, said method (a) measuring one or more ERG parameters, in an embodiment one or more of the following ERG parameters in the subject: the cone a-Wave amplitude, the cone a-Wave implicit time, the cone b-Wave amplitude, the cone b-Wave implicit time, the rod a-Wave amplitude, the rod a-Wave implicit time, rod b-Wave amplitude and the rod b-Wave implicit time, in the subject; (b) calculating an SZ probability score (i.e., probability that the subject suffers from SZ) by adjusting the value of one or more of the ERG parameters by one or more transformation analyses; and (c) determining whether a subject suffers from schizophrenia (SZ) or has a predisposition thereto based on the SZ probability score. In an embodiment, the one or more transformation analyses comprises logistic regression analysis, in a further embodiment the logistic regression analysis comprises (i) adjusting the value of one or more of the ERG parameters by an appropriate weighting coefficient to produce a weighted score for each ERG value, and (ii) combining the weighted score for each ERG value to generate the SZ probability score. In an embodiment, the appropriate weighting coefficients are determined based on the ERG parameter value(s) measured in a population of SZ patients and in a population of non-SZ (control, "healthy") subjects. In an embodiment, the logistic regression model was determined using ERG parameter values measured in a first population of SZ subjects and a second population of control subjects.

In an embodiment, the SZ probability score is determined using at least one of logistic regression models 1, 2a-2h, 3, 4, 5 or 6 set forth in Table 3A or models 1, 2a-2h, 3, 4 or 5 set forth in Table 14A. It will be understood that the reference to logistic regression models set forth in the Tables described herein means that the intercept value and the regression coefficients indicated for each model (either the ranges defined by the 95% CI or the specific values) are used in the algorithm to calculate the probability score. For example, for model 2a of Table 3A, the method comprises measuring at least the cone a-wave amplitude in the subject, and incorporating that measured value (as well as the gender and age of the subject) in the following formula, to obtain the SZ probability score:

SZprobability score=Exp[2.56−0.35(gender)−0.02(age)−0.14(phAamp)]/(1+Exp[2.56−0.35(gender)−0.02(age)−0.14(phAamp)])

in which
Gender=1 if the subject is a female and 0 if the subject is a male; and
phAamp=cone a-Wave amplitude, fixed intensity of 7.5 cd×s/m²(int1).

The same approach may be applied to all the models set forth in the Tables presented herein.

In an embodiment, the method further comprises measuring the cone a-Wave amplitude, in combination with one or more of the above ERG parameters.

In an embodiment, the SZ probability score is determined using a regression algorithm that includes age, gender, or both age and gender, as covariate. In an embodiment, the method comprises measuring:

the cone a-Wave amplitude, and an SZ probability score of more than 0.5 when calculated using a regression algorithm (see model 2a in Table 3A for the estimate of the coefficients) is indicative that subject suffers from schizophrenia (SZ) or has a predisposition thereto:

the cone a-Wave implicit time, and an SZ probability score of more than 0.5 when calculated using a regression algorithm (see model 2b in Table 3A for the estimate of the coefficients) is indicative that subject suffers from schizophrenia (SZ) or has a predisposition thereto:

the cone b-Wave amplitude, and an SZ probability score of more than 0.5 when calculated using a regression algorithm (see model 2c in Table 3A for the estimate of the coefficients) is indicative that subject suffers from schizophrenia (SZ) or has a predisposition thereto:

the cone b-Wave implicit time, and an SZ probability score of more than 0.5 when calculated using a regression algorithm (see model 2d in Table 3A for the estimate of the coefficients) is indicative that subject suffers from schizophrenia (SZ) or has a predisposition thereto;

the rod a-Wave amplitude, and an SZ probability score of more than 0.5 when calculated using a regression algorithm (see model 2e in Table 3A for the estimate of the coefficients) is indicative that subject suffers from schizophrenia (SZ) or has a predisposition thereto;

the rod a-Wave implicit time, and an SZ probability score of more than 0.5 when calculated using a regression algorithm (see model 2f in Table 3A for the estimate of the coefficients) is indicative that subject suffers from schizophrenia (SZ) or has a predisposition thereto;

the rod b-Wave amplitude, and the rod b-Wave implicit time, and an SZ probability score of more than 0.5 when calculated using a regression algorithm (see model 2g in Table 3A for the estimate of the coefficients) is indicative that subject suffers from schizophrenia (SZ) or has a predisposition thereto; or the rod b-Wave implicit time, and an SZ probability score of more than 0.5 when calculated using a regression algorithm (see model 2h in Table 3A for the estimate of the coefficients) is indicative that subject suffers from schizophrenia (SZ) or has a predisposition.

In an embodiment, the SZ probability score is calculated using at least 2 ERG parameters, e.g., 2, 3, 4, 5 or 6 ERG parameters. The present inventors have shown that using combinations of ERG parameters permits to increase the predictive value of the methods.

In an embodiment, the method comprises measuring:
the cone b-Wave implicit time and the rod a-Wave implicit time, and an SZ probability score of more than 0.5 when calculated using a regression algorithm (see model 3 in Table 3A for the estimate of the coefficients) is indicative that subject suffers from schizophrenia (SZ) or has a predisposition thereto;

the cone b-Wave implicit time, the rod a-Wave implicit time and the rod b-Wave amplitude, and an SZ probability score of more than 0.5 when calculated using a regression algorithm (see model 4 in Table 3A for the estimate of the coefficients) is indicative that subject suffers from schizophrenia (SZ) or has a predisposition thereto;

the cone b-Wave implicit time, the rod a-Wave implicit time, the rod b-Wave amplitude, and the cone a-Wave amplitude, and an SZ probability score of more than 0.5 when calculated using a regression algorithm (see model 5 in Table 3A for the estimate of the coefficients) is indicative that subject suffers from schizophrenia (SZ) or has a predisposition thereto;

the cone b-Wave implicit time, the rod a-Wave implicit time, the rod b-Wave amplitude, the cone a-Wave amplitude and the cone a-Wave implicit time, and an SZ probability score of more than 0.5 when calculated using a regression algorithm (see model 6 in Table 3A for the estimate of the coefficients) is indicative that subject suffers from schizophrenia (SZ) or has a predisposition thereto;

the cone b-Wave implicit time, the rod a-Wave implicit time, the rod b-Wave amplitude, the cone a-Wave amplitude, the cone a-Wave implicit time and the rod b-Wave implicit time, and an SZ probability score of more than 0.5 when calculated using a regression algorithm (see model 1 in Table 3A for the estimate of the coefficients) is indicative that subject suffers from schizophrenia (SZ) or has a predisposition thereto. In an embodiment, the regression algorithm is of the formula below:

$$SZprobability\ score = Exp[-19.03 - 0.15(gender) - 0.04(age) + 1.61(phBlat) - 0.86(scAlat) - 0.02(scBamp) - 0.11(phAamp) - 0.65(phAlat) + 0.10(scBlat)]/(1 + Exp[-19.03 - 0.15(gender) - 0.04(age) + 1.61(phBlat) - 0.86(scAlat) - 0.02(scBamp) - 0.11(phAamp) - 0.65(phAlat) + 0.10(scBlat)])$$

in which

Gender=1 if the subject is a female and 0 if the subject is a male;

phBlat=cone b-Wave implicit time, average of three intensities (13.33, 23.71 and 50 cd·s/m$^2$; 3-int);

scAlat=rod a-Wave implicit time, flash intensity of 1 cd×s/m$^2$ (int2);

scBamp=rod b-Wave amplitude, flash intensity of 1 cd×s/m$^2$ (int2);

phAamp=cone a-Wave amplitude, fixed intensity of 7.5 cd×s/m$^2$ (int1);

phAlat=cone a-Wave implicit time, average of three intensities (13.33, 23.71 and 50 cd·s/m$^2$; 3-int); and scBlat=rod b-Wave implicit time, flash intensity of 1 cd×s/m$^2$ (int2).

As noted above, in all the algorithm formulas described herein, the intercept value and the regression coefficients (for each variable) may vary within the ranges defined by the 95% confidence intervals (95% CI) set forth in the Tables below. Thus, accordingly, in the formula just-noted formula, the intercept value (−19.03) may be a value from about −30.7 to about −8.2 (see Table 3A, model 1). Similarly, in the just-noted formula, the regression coefficient for cone b-wave implicit time (1.61) may vary from about 1.23 to about 2.05 (see Table 3A, model 1). Accordingly, in an embodiment, the formula is:

$$SZprobability\ score = Exp[[-30.7\ to\ -8.2] + [-0.50\ to\ 0.23](gender) - [0\ to\ 0.08](age) + [1.23\ to\ 2.05](phBlat) - [0.49\ to\ 1.26](scAlat) - [0.01\ to\ 0.03](scBamp) - [0.03\ to\ 0.20](phAamp) - [0.18\ to\ 1.13](phAlat) + [0.02\ to\ 0.19](scBlat)]/(1 + Exp[[-30.7\ to\ -8.2] + [-0.50\ to\ 0.23](gender) - [0\ to\ 0.08](age) + [1.23\ to\ 2.05](phBlat) - [0.49\ to\ 1.26](scAlat) - [0.01\ to\ 0.03](scBamp) - [0.03\ to\ 0.20](phAamp) - [0.18\ to\ 1.13](phAlat) + [0.02\ to\ 0.19](scBlat)]$$

In another embodiment, the intercept value and the regression coefficients (for each variable) may vary by about 20% or less, in an embodiment by about 10% or 5% or less. Thus, accordingly, the formula just-noted formula, the intercept value (19.03) may be a value from about 15.2 to about 22.8 (about 20%), or from about 17.1 to about 20.9 (about 10%), or from about 18 to about 20 (about 5%). Similarly, in the just-noted formula, the regression coefficient for phBlat (1.61) may vary from about 1.41 to about 1.81, or from about 1.51 to about 1.71, etc.

The skilled person would understand that these variations apply to all the algorithms/formulas described herein.

In an embodiment, the method comprises calculating the SZ probability score using the above-described regression algorithms.

In another embodiment, the SZ probability score is determined using logistic regression model 1 set forth in Table 14A.

In another aspect, the present invention provides a method for determining whether a subject suffers from a bipolar disorder (BP) or has a predisposition thereto, said method comprising (a) measuring one or more ERG parameters, in an embodiment one or more of the following ERG parameters in the subject: the cone a-Wave amplitude, the cone a-Wave implicit time, the cone b-Wave amplitude, the cone b-Wave implicit time, the rod a-Wave amplitude, the rod a-Wave implicit time, rod b-Wave amplitude and the rod b-Wave implicit time, in the subject; (b) calculating a BP probability score by adjusting the value of one or more of the ERG parameters by one or more transformation analyses; and (c) determining whether the subject suffers from bipolar disorder (BP) or has a predisposition thereto based on the BP probability score. In an embodiment, the one or more transformation analyses comprises logistic regression analysis, in a further embodiment the logistic regression analysis comprises (i) adjusting the value of one or more of the ERG parameters by an appropriate weighting coefficient to produce a weighted score for each ERG value, and (ii) combining the weighted score for each ERG value to generate the BP probability score. In an embodiment, the appropriate weighting coefficients are determined based on the ERG parameter value(s) measured in a population of BP patients and in a population of non-BP (control, "healthy") subjects. In an embodiment, the BP probability score is determined using a regression algorithm that includes age, gender, or both age and gender, as covariate. In an embodiment, the logistic regression model was determined using ERG parameter values measured in a first population of BP subjects and a second population of control subjects.

In an embodiment, the BP probability score is determined using at least one of logistic regression models 1, 2a-2h, 3, 4, 5 or 6 set forth in Table 9A.

In an embodiment, the method comprises measuring:

the cone a-Wave amplitude, and a BP probability score of more than 0.5 when calculated using a regression algorithm (see model 2a in Table 9A for the estimate of the coefficients) is indicative that subject suffers from BP or has a predisposition;

the cone a-Wave implicit time, and a BP probability score of more than 0.5 when calculated using a regression algorithm (see model 2b in Table 9A for the estimate of the coefficients) is indicative that subject suffers from BP or has a predisposition;

the cone b-Wave amplitude, and a BP probability score of more than 0.5 when calculated using a regression algorithm (see model 2c in Table 9A for the estimate of the coefficients) is indicative that subject suffers from BP or has a predisposition thereto;

the cone b-Wave implicit time, and a BP probability score of more than 0.5 when calculated using a regression algorithm (see model 2d in Table 9A for the estimate of the coefficients) is indicative that subject suffers from BP or has a predisposition thereto;

the rod a-Wave amplitude, and a BP probability score of more than 0.5 when calculated using a regression algorithm (see model 2e in Table 9A for the estimate of the coefficients) is indicative that subject suffers from BP or has a predisposition thereto;

the rod a-Wave implicit time, and a BP probability score of more than 0.5 when calculated using a regression algorithm (see model 2f in Table 9A for the estimate of the coefficients) is indicative that subject suffers from BP or has a predisposition thereto;

the rod b-Wave amplitude, and a BP probability score of more than 0.5 when calculated using a regression algorithm (see model 2g in Table 9A for the estimate of the coefficients) is indicative that subject suffers from BP or has a predisposition thereto;

the rod b-Wave implicit time, and a BP probability score of more than 0.5 when calculated using a regression algorithm (see model 2h in Table 9A for the estimate of the coefficients) is indicative that subject suffers from BP or has a predisposition thereto;

the cone b-Wave implicit time and the rod a-Wave implicit time, and a BP probability score of more than 0.5 when calculated using a regression algorithm (see model 3 in Table 9A for the estimate of the coefficients) is indicative that subject suffers from BP or has a predisposition thereto;

the cone b-Wave implicit time, the rod a-Wave implicit time and the rod a-Wave amplitude, and a BP probability score of more than 0.5 when calculated using a regression algorithm (see model 4 in Table 9A for the estimate of the coefficients) is indicative that subject suffers from BP or has a predisposition thereto;

the cone b-Wave implicit time, the rod a-Wave implicit time, the rod b-Wave amplitude and the cone a-Wave implicit time, and a BP probability score of more than 0.5 when calculated using a regression algorithm (see model 5 in Table 9A for the estimate of the coefficients) is indicative that subject suffers from BP or has a predisposition thereto;

the cone b-Wave amplitude, the rod a-Wave implicit time, the rod b-Wave amplitude and the cone a-Wave implicit time, and a BP probability score of more than 0.5 when calculated using a regression algorithm (see model 6 in Table 9A for the estimate of the coefficients) is indicative that subject suffers from BP or has a predisposition thereto;

the cone b-Wave implicit time, the rod a-Wave implicit time, the rod b-Wave amplitude, the rod b-wave implicit time, the cone b-Wave amplitude and the cone a-Wave implicit time, and a BP probability score of more than 0.5 when calculated using a regression algorithm of the formula below is indicative that subject suffers from BP or has a predisposition thereto:

$$BP\text{probability score} = \mathrm{Exp}[-14.15+0.57(\text{gender})-0.002(\text{age})+1.46(\text{phBlat})-1.24(\text{scAlat})-0.03(\text{scBamp})+0.17(\text{scBlat})+0.04(\text{phBamp})-0.55(\text{phAlat})]/(1+\mathrm{Exp}[-14.15+0.57(\text{gender})-0.002(\text{age})+1.46(\text{phBlat})-1.24(\text{scAlat})-0.03(\text{scBamp})+0.17(\text{scBlat})+0.04(\text{phBamp})-0.55(\text{phAlat})])$$

in which:

Gender=1 if the subject is a female and 0 if the subject is a male;

phBlat=cone b-Wave implicit time, average of three intensities (13.33, 23/1 and 50 cd·s/m$^2$; 3-int);

scAlat=rod a-Wave implicit time, flash intensity of 1 cd×s/m$^2$ (int2);

scBamp=rod b-Wave amplitude, flash intensity of 1 cd×s/m$^2$ (int2);

scBlat=rod a-Wave implicit time, flash intensity of 1 cd×s/m$^2$ (int2);

phBamp=cone a-Wave amplitude, peak maximal response (Vmax); and phAlat=cone a-Wave implicit time, average of three intensities (13.33, 23.71 and 50 cd·s/m$^2$; 3-int).

As noted above, in all the algorithm formulas described herein, the intercept value and the regression coefficients may vary within the 95% CI disclosed in the Tables, or by about 20% or less, in an embodiment by about 10% or 5% or less.

In another aspect, the present invention provides a method for determining whether a subject suffers from major depression disorder (MDD) or has a predisposition thereto, said method comprising (a) measuring one or more ERG parameters, in an embodiment one or more of the following ERG parameters in the subject: the cone a-Wave amplitude, the cone a-Wave implicit time, the cone b-Wave amplitude, the cone b-Wave implicit time, the rod a-Wave amplitude, the rod a-Wave implicit time and the rod b-Wave implicit time, in the subject; (b) calculating an MDD probability score by adjusting the value of one or more of the ERG parameters by one or more transformation analyses; and (c) determining whether the subject suffers from MDD or has a predisposition thereto based on said MDD probability score. In an embodiment, the one or more transformation analyses comprises logistic regression analysis, in a further embodiment the multiple logistic regression analysis comprises (i) adjusting the value of one or more of the ERG parameters by an appropriate weighting coefficient to produce a weighted score for each ERG value, and (ii) combining the weighted score for each ERG value to generate the MDD probability score. In an embodiment, the appropriate weighting coefficients are determined based on the ERG parameter value(s) measured in a population of MDD patients and in a population of non-MDD (control, "healthy") subjects. The skilled person would be able to readily identify suitable logistic regression algorithms based on ERG parameters and combinations of ERG parameters that would permit to predict MDD for a given subject (i.e. the probability that a subject suffers from MDD) based on the ERG parameters measured in the subject, for example using the methodology described in the example below for SZ and BP.

In an embodiment, the above-mentioned method is an aid for the diagnosis of psychiatric disorders (e.g., SZ, BP, MDD). Accordingly, the above-mentioned methods may be performed in combination with other methods or markers for diagnosing psychiatric disorders (e.g., SZ, BP, MDD), for example evaluation by a trained mental-health professional, administration of a variety of personality tests and neuropsychological tests, neurocognitive measurements, gathering of background (including medical) information about the individual (e.g., patient's self-reported experiences, behavior reported by relatives or friends), presence of biological and/or genetic markers associated with the psychiatric disorder, etc. In another embodiment, the above-mentioned methods based on ERG parameters are performed on subjects suspected of suffering from a psychiatric disorder (e.g., SZ, BP or MDD), and are used to confirm the diagnosis.

Identification and Monitoring of Subjects Predisposed or at Risk of Developing a Psychiatric Disorder (Asymptomatic, Non-Affected)

The present inventors have shown that the assessment of ERG parameters in asymptomatic, non-affected young subject may be useful for detecting subjects at risk of developing a psychiatric disorder in the future. The subjects identified as being at risk could be more closely monitored.

Thus, in another aspect, the present invention provides a method for determining whether an asymptomatic young subject is at risk of suffering from a psychiatric disorder (e.g., to detect whether an asymptomatic patient is a SZ patient, to assess the risk/likelihood that a subject develops the disease or condition at a later time), said method comprising:

measuring one or more ERG parameters, in an embodiment one or more of the following ERG parameters in the subject: the rod a-Wave amplitude, the rod a-Wave implicit time and/or the rod b-Wave implicit time, in the subject; wherein (i) a rod a-Wave amplitude that is lower, a rod a-Wave implicit time that is higher, and/or a rod b-Wave implicit time that is higher, relative to the corresponding parameter(s) measured in a control subject not at risk of suffering from a psychiatric disorder; or (ii) a rod a-Wave amplitude that is substantially similar or lower, a rod a-Wave implicit time that is substantially similar or higher, and/or rod b-Wave implicit time that is substantially similar or higher, relative to the corresponding parameter(s) measured in a control subject at risk of suffering from a psychiatric disorder, is indicative that the asymptomatic young subject is at risk of suffering from a psychiatric disorder.

In an embodiment, the method further comprises measures the rod b-Wave amplitude, and wherein (i) a rod b-Wave amplitude that is lower relative to the corresponding parameter measured in a control subject not at risk of suffering from a psychiatric disorder, or (ii) a rod b-Wave amplitude that is substantially similar or lower relative to the corresponding parameter measured in a control subject at risk of suffering from a psychiatric disorder, is indicative that the asymptomatic young subject is at risk of suffering from a psychiatric disorder.

In another aspect, the present invention provides the use of one or more of the above-mentioned ERG parameters as biomarkers for the identification of asymptomatic young subjects at risk of suffering from a psychiatric disorder.

In an embodiment, the asymptomatic young subject is 25 years old or less, in further embodiments 24, 23, 22, 21, 20, 19, or 18 years old or less.

In an embodiment, the psychiatric disorder is SZ or BP.

In embodiments, the ERG values for one or more of the ERG parameters are subjected to one or more transformation analyses. Thus, in another aspect, the present invention provides a method for determining whether an asymptomatic young subject is at risk of suffering from a psychiatric disorder, said method comprising (a) measuring one or more of the following ERG parameters in the subject: the cone a-Wave amplitude, the cone a-Wave implicit time, the cone b-Wave amplitude, the cone b-Wave implicit time, the rod a-Wave amplitude, the rod a-Wave implicit time, the rod a-Wave amplitude and the rod b-Wave implicit time, in the subject; (b) calculating a psychiatric disorder risk probability score by adjusting the value of one or more of the ERG parameters by one or more transformation analyses; and (c) determining whether the asymptomatic young subject is at risk of suffering from a psychiatric disorder based on said psychiatric disorder risk probability score.

In an embodiment, the one or more transformation analyses comprise logistic regression analysis, wherein the logistic regression analysis comprises (i) adjusting the value of one or more of the ERG parameters by an appropriate weighting coefficient to produce a weighted score for each ERG value, and (ii) combining the weighted score for each ERG value to generate the psychiatric disorder risk probability score. In an embodiment, the psychiatric disorder risk probability score is determined using a regression algorithm that includes age, gender, or both age and gender, as covariate. In an embodiment, the logistic regression model was determined using ERG parameter values measured in a first population of nonaffected high-risk offspring (HR) of SZ or BP subjects and a second population of control subjects.

In an embodiment, the psychiatric disorder risk probability score is determined using at least one of logistic regression models 1, 2a-2h or 3 set forth in Table 12A.

In an embodiment, the method comprises measuring:

the cone a-Wave amplitude, and a psychiatric disorder probability score of more than 0.5 when calculated using a regression algorithm (see model 2a in Table 12A for the estimate of the coefficients) is indicative that subject is at risk of suffering from a psychiatric disorder;

the cone a-Wave implicit time, and a psychiatric disorder probability score of more than 0.5 when calculated using a regression algorithm (see model 2b in Table 12A for the estimate of the coefficients) is indicative that subject is at risk of suffering from a psychiatric disorder;

the cone b-Wave amplitude, and a psychiatric disorder risk probability score of more than 0.5 when calculated using a regression algorithm (see model 2c in Table 12A for the estimate of the coefficients) is indicative that subject is at risk of suffering from a psychiatric disorder;

the cone b-Wave implicit time, and a psychiatric disorder risk probability score of more than 0.5 when calculated using a regression algorithm (see model 2d in Table 12A for the estimate of the coefficients is indicative that subject is at risk of suffering from a psychiatric disorder;

the rod a-Wave amplitude, and a psychiatric disorder risk probability score of more than 0.5 when calculated using a regression algorithm (see model 2e in Table 12A for the estimate of the coefficients) indicative that subject is at risk of suffering from a psychiatric disorder;

the rod a-Wave implicit time, and a psychiatric disorder risk probability score of more than 0.5 when calculated using a regression algorithm (see model 2f in Table 12A for the estimate of the coefficients) is indicative that subject is at risk of suffering from a psychiatric disorder;

the rod b-Wave amplitude, and a psychiatric disorder risk probability score of more than 0.5 when calculated using a regression algorithm (see model 2g in Table 12A for the estimate of the coefficients) is indicative that subject is at risk of suffering from a psychiatric disorder;

the rod b-Wave implicit time, and a psychiatric disorder risk probability score of more than 0.5 when calculated using a regression algorithm (see model 2h in Table 12A for the estimate of the coefficients) is indicative that subject is at risk of suffering from a psychiatric disorder;

the rod b-Wave implicit time and the rod b-wave amplitude, and a psychiatric disorder risk probability score of more than 0.5 when calculated using a regression algorithm (see model 3 in Table 12A for the estimate of the coefficients) is indicative that subject is at risk of suffering from a psychiatric disorder;

the rod b-Wave amplitude, the cone b-Wave implicit time and the cone b-Wave amplitude, and a psychiatric disorder risk probability score of more than 0.5 when calculated using a regression algorithm of the formula below is indicative that subject is at risk of suffering from a psychiatric disorder:

Psychiatric disorder risk probability score=Exp[−16.35+0.36(gender)+0.20(age)−0.05(scBamp)+0.50(phBlat)+0.07(phBamp)]/(1+Exp[−16.35+0.36(gender)+0.20(age)−0.05(scBamp)+0.50(phBlat)+0.07(phBamp)])

in which:

Gender=1 if the subject is a female and 0 if the subject is a male;

scBamp=rod b-Wave amplitude, flash intensity of 1 cd×s/m$^2$ (int2);

phBlat=cone b-Wave implicit time, peak maximal response (Vmax); and phBamp=cone b-Wave amplitude, peak maximal response (Vmax).

Differential Diagnosis

In the studies described herein, the present inventors have shown that certain ERG parameters permit to distinguish patients suffering from a first psychiatric disorder (e.g., SZ) from patients suffering from a second psychiatric disorder (e.g., BP). The present invention thus provides methods for the differential diagnosis of psychiatric disorders Accordingly, in another aspect, the present invention provides a method for the differential diagnosis of SZ from BP (i.e. for determining whether a subject suspected of suffering from SZ or BP suffers from or is predisposed to suffering from SZ or BP), said method comprising measuring (i) the cone a-wave amplitude; (ii) the cone a-wave implicit time; (iii) the cone b-wave amplitude, (iv) the rod a-wave implicit time; and/or (v) the log K in the subject; wherein (a)
(i) a cone a-wave amplitude, a log K, and/or a cone b-wave amplitude that is/are similar or lower, and/or a cone a-wave implicit time and/or a rod a-wave implicit time that is/are similar or higher relative to the corresponding value(s) measured in subjects known to suffer from SZ, or to be predisposed thereto, or
(ii) a cone a-wave amplitude, a log K, and/or a cone b-wave amplitude that is/are higher, and/or a cone a-wave implicit time and/or a rod a-wave implicit time that is/are lower to the corresponding value(s) measured in subjects known to suffer from BP or to be predisposed thereto, is indicative that said subject suffers from SZ or is predisposed thereto; and (b)
(i) a cone a-wave amplitude, a log K, and/or a cone b-wave amplitude that is/are similar or higher, and/or a cone a-wave implicit time and/or a rod a-wave implicit time that is/are similar or lower, relative to the corresponding value(s) measured in subjects known suffer from BP or to be predisposed thereto, or
(ii) a cone a-wave amplitude, a log K, and/or a cone b-wave amplitude that is lower, and/or a cone a-wave implicit time and/or a rod a-wave implicit time that is/are higher, relative to the corresponding value(s) measured in subjects known to suffer from SZ or to be predisposed thereto, is indicative that said subject suffers from BP or is predisposed thereto.

In an embodiment, the method comprises measuring (i) the cone a-wave amplitude. In an embodiment, the method comprises measuring (ii) the cone a-wave implicit time. In an embodiment, the method comprises measuring (iii) the cone b-wave amplitude. In an embodiment, the method comprises measuring (iv) the rod a-wave implicit time. In an embodiment, the method comprises measuring (v) the log K. In an embodiment, the method comprises measuring two or three of parameters (i)-(v). In an embodiment, the method comprises measuring parameters (i) to (v). In an embodiment, the method comprises measuring one or more of the ERG parameters exhibiting statistical significance (as assessed by univariate analysis) between SZ and BP subjects depicted in Table 15.

In another aspect, the present invention provides a method for the differential diagnosis of SZ from MDD (i.e. for determining whether a subject suspected of suffering from SZ or MDD suffers from or is predisposed to suffering from SZ or MDD), said method comprising measuring the cone b-wave implicit time in the subject; wherein (a)
(i) a cone b-wave implicit time is similar or higher relative to the corresponding value(s) measured in subjects known to suffer from SZ, or to be predisposed thereto, or
(ii) a cone b-wave implicit time that is higher relative to the corresponding value(s) measured in subjects known to suffer from MDD or to be predisposed thereto, is indicative that said subject suffers from SZ or is predisposed thereto; and (b)
(i) a cone b-wave implicit time that is similar or lower relative to the corresponding value(s) measured in subjects known suffer from MDD or to be predisposed thereto or
(ii) a cone b-wave implicit time that is lower relative to the corresponding value(s) measured in subjects known to suffer from SZ or to be predisposed thereto, is indicative that said subject suffers from MDD or is predisposed thereto.

In another aspect, the present invention provides method for the differential diagnosis of BP from MDD (i.e. for determining whether a subject suspected of suffering from BP or MDD suffers from or is predisposed to suffering from BP or MDD), said method comprising measuring (i) the cone a-wave amplitude and/or (ii) the rod a-wave implicit time in the subject; wherein (a)
(i) a cone b-wave implicit time that is similar or higher and/or a rod a-wave implicit time that is similar or lower relative to the corresponding value(s) measured in subjects known to suffer from BP, or to be predisposed thereto, or
(ii) a cone b-wave implicit time that is higher and/or a rod a-wave implicit time that is lower relative to the corresponding value(s) measured in subjects known to suffer from MDD or to be predisposed thereto, is indicative that said subject suffers from BP or is predisposed thereto; and (b)
(i) a cone b-wave implicit time that is similar or lower and/or a rod a-wave implicit time that is similar or higher relative to the corresponding value(s) measured in subjects known suffer from MDD or to be predisposed thereto, or (i) a cone b-wave implicit time that is lower and/or a rod a-wave implicit time that is higher, relative to the corresponding value(s) measured in subjects known to suffer from BP or to be predisposed thereto, is indicative that said subject suffers from MDD or is predisposed thereto.

In another aspect, the present invention provides the use of one or more of the above-mentioned ERG parameters as biomarkers for the differential diagnosis of SZ and BP, or of a predisposition thereto.

In another aspect, the present invention provides the use of one or more of the above-mentioned ERG parameters as biomarkers for the differential diagnosis of SZ and MDD, or of a predisposition thereto.

In another aspect, the present invention provides the use of one or more of the above-mentioned ERG parameters as biomarkers for the differential diagnosis of BP and MDD, or of a predisposition thereto.

In embodiments, the ERG values for one or more of the ERG parameters are subjected to one or more transformation analyses.

In another aspect, the present invention provides a method for determining whether a subject (i) suffers from SZ or has a predisposition thereto or (ii) suffers from BP or has a predisposition thereto, said method comprises: (a) measuring one or more of the following ERG parameters in the subject: the cone a-Wave amplitude, the cone a-Wave implicit time, the cone b-Wave amplitude, the cone b-Wave implicit time, the rod a-Wave amplitude, the rod a-Wave implicit time, rod b-Wave amplitude and the rod b-Wave implicit time, in the subject; (b) calculating an SZ or BP probability score by adjusting the value of one or more of the ERG parameters by one or more transformation analyses; and (c) determining whether the subject suffers from SZ or BP or has a predisposition thereto based on the SZ or BP probability score probability score. In an embodiment, the one or more transformation analyses comprises logistic regression analysis, in a further embodiment the logistic regression analysis comprises (i) adjusting the value of one or more of the ERG parameters by an appropriate weighting coefficient to produce a weighted score for each ERG value, and (ii) combining the weighted score for each ERG value to generate the SZ (or BP) probability score. In an embodiment, the appropriate weighting coefficients are determined based on the ERG parameter value(s) measured in a population of SZ patients and in a population of BP patients. In an embodiment, the SZ (or BP) probability score is determined using a regression algorithm that includes age, gender, or both age and gender, as covariate. In an embodiment, the logistic regression model was determined using ERG parameter values measured in a first population of SZ subjects and a second population of BP subjects. In an embodiment, the SZ or BP probability score is determined using at least one of logistic regression models 7, 8a-8h, 9 or 10 set forth in Table 9A or models 1, 2a-2h set forth in Table 16A.

In an embodiment, the method comprises measuring:

the cone a-Wave amplitude, and wherein an SZ probability score of more than 0.5 when calculated using a regression algorithm (see model 8a in Table 9A for the estimate of the coefficients) is indicative that subject suffers from SZ or has a predisposition, and an SZ probability score of less than 0.5 is indicative that subject suffers from BP or has a predisposition thereto;

the cone a-Wave implicit time, and wherein an SZ probability score of more than 0.5 when calculated using a regression algorithm (see model 8b in Table 9A for the estimate of the coefficients) is indicative that subject suffers from SZ or has a predisposition, and an SZ probability score of less than 0.5 is indicative that subject suffers from BP or has a predisposition thereto;

the cone b-Wave amplitude, and wherein an SZ probability score of more than 0.5 when calculated using a regression algorithm (see model 8c in Table 9A for the estimate of the coefficients) is indicative that subject suffers from SZ or has a predisposition thereto, and an SZ probability score of less than 0.5 is indicative that subject suffers from BP or has a predisposition thereto;

the cone b-Wave implicit time, and wherein an SZ probability score of more than 0.5 when calculated using a regression algorithm (see model 8d in Table 9A for the estimate of the coefficients) is indicative that subject suffers from SZ or has a predisposition thereto, and an SZ probability score of less than 0.5 is indicative that subject suffers from BP or has a predisposition thereto;

the rod a-Wave amplitude, and wherein an SZ probability score of more than 0.5 when calculated using a regression algorithm (see model 8e in Table 9A for the estimate of the coefficients) is indicative that subject suffers from SZ or has a predisposition thereto, and an SZ probability score of less than 0.5 is indicative that subject suffers from BP or has a predisposition thereto;

the rod a-Wave implicit time, and wherein an SZ probability score of more than 0.5 when calculated using a regression algorithm (see model 8f in Table 9A for the estimate of the coefficients) is indicative that subject suffers from SZ or has a predisposition thereto, and an SZ probability score of less than 0.5 is indicative that subject suffers from BP or has a predisposition thereto;

the rod b-Wave amplitude, and wherein an SZ probability score of more than 0.5 when calculated using a regression algorithm (see model 8g in Table 9A for the estimate of the coefficients) is indicative that subject suffers from SZ or has a predisposition thereto, and an SZ probability score of less than 0.5 is indicative that subject suffers from BP or has a predisposition thereto;

the rod b-Wave implicit time, and wherein an SZ probability score of more than 0.5 when calculated using a regression algorithm (see model 8h in Table 9A for the estimate of the coefficients) is indicative that subject suffers from SZ or has a predisposition thereto, and an SZ probability score of less than 0.5 is indicative that subject suffers from BP or has a predisposition thereto;

the rod a-Wave implicit time and the cone a-Wave amplitude, and wherein an SZ probability score of more than 0.5 when calculated using a regression algorithm (see model 9 in Table 9A for the estimate of the coefficients) is indicative that subject suffers from SZ or has a predisposition thereto, and an SZ probability score of less than 0.5 is indicative that subject suffers from BP or has a predisposition thereto;

the rod a-Wave implicit time, the cone a-Wave amplitude and the rod b-wave amplitude, and wherein an SZ probability score of more than 0.5 when calculated using a regression algorithm (see model 10 in Table 9A for the estimate of the coefficients) is indicative that subject suffers from SZ or has a predisposition thereto, and an SZ probability score of less than 0.5 is indicative that subject suffers from BP or has a predisposition thereto;

the cone a-Wave amplitude, the rod a-Wave implicit time and the rod b-wave amplitude, and wherein an SZ probability score of more than 0.5 when calculated using a regression algorithm of the formula below is indicative that subject suffers from SZ or has a predisposition thereto, and an SZ probability score of less than 0.5 when calculated using a regression algorithm of the formula below is indicative that subject suffers from BP or has a predisposition thereto:

$$SZ\text{probability score}=\text{Exp}[-4.26-0.91(\text{gender})-0.04(\text{age})-0.18(\text{phAamp})+0.08(\text{scAlat}_{vmax})+0.01(\text{scBamp})+0.22(\text{scAlat}_{int2})]/(1+\text{Exp}[-4.26-0.91(\text{gender})-0.04(\text{age})-0.18(\text{phAamp})+0.08(\text{scAlat}_{vmax})+0.01(\text{scBamp})+0.22(\text{scAlat}_{int2})])$$

in which:
Gender=1 if the subject is a female and 0 if the subject is a male;
phAamp=cone a-Wave amplitude, average of three intensities (13.33, 23.71 and 50 cd·s/m², 3-int);
scAlat$_{vmax}$=rod a-Wave implicit time, saturating amplitude at first plateau, flash intensity of 0.1 cd×s/m² (Vmax);
scBamp=rod b-Wave amplitude, saturating amplitude at first plateau, flash intensity of 0.1 cd×s/m² (Vmax);
scAlat$_{int2}$=rod a-Wave implicit time, flash intensity of 1 cd×s/m² (int2).

In an embodiment, the SZ probability score is calculated using the regression algorithm according to model 1 of Table 16A.

In another aspect, the present invention provides a method for determining whether a subject suffers from or is predisposed to suffering from schizophrenia (SZ) or major depression (MDD), said method comprising (a) measuring one or more of the following ERG parameters in the subject: the cone a-Wave amplitude, the cone a-Wave implicit time, the cone b-Wave amplitude, the cone b-Wave implicit time, the rod a-Wave amplitude, the rod a-Wave implicit time, the rod b-Wave amplitude and the rod b-Wave implicit time, in the subject; (b) calculating an SZ or MDD probability score by adjusting the value of one or more of the ERG parameters by one or more transformation analyses; and (c) determining whether the subject suffers from SZ or MDD or has a predisposition thereto based on said SZ or MDD probability score. In an embodiment, the one or more transformation analyses comprises logistic regression analysis, in a further embodiment the logistic regression analysis comprises (i) adjusting the value of one or more of the ERG parameters by an appropriate weighting coefficient to produce a weighted score for each ERG value, and (ii) combining the weighted score for each ERG value to generate the SZ (or MDD) probability score. In an embodiment, the appropriate weighting coefficients (logistic regression model) are determined based on the ERG parameter value(s) measured in a population of SZ patients and in a population of MDD patients. The skilled person would be able to readily identify suitable logistic regression algorithms based on ERG parameters and combinations of ERG parameters that would permit to predict SZ or MDD for a given subject (i.e. the probability that a subject suffers from SZ or MDD) based on the ERG parameters measured in the subject, for example using the methodology described in the example below for the differential diagnosis of SZ and BP.

In an embodiment, the above-mentioned method is an aid for the differential diagnosis of psychiatric disorders (e.g., SZ, BP, MDD). Accordingly, the above-mentioned methods may be performed in combination with other methods or markers for diagnosing psychiatric disorders (e.g., SZ, BP, MDD), for example evaluation by a trained mental-health professional, administration of a variety of personality tests and neuropsychological tests, neurocognitive measurements, gathering of background (including medical) information about the individual (e.g., patient's self-reported experiences, behavior reported by relatives or friends), presence of biological and/or genetic markers associated with the psychiatric disorder, etc. In another embodiment, the above-mentioned methods based on ERG parameters are performed on subjects suspected of suffering from a psychiatric disorder (e.g., SZ, BP or MDD), and are used to confirm the diagnosis (i.e. to aid in determining the specific psychiatric disorder (e.g., SZ or BP) afflicting the patients).

In another aspect, the present invention provides a method for identifying one or more ERG parameters useful for the differential diagnosis of psychiatric disorders (i.e. for discriminating between subjects suffering from a first psychiatric disorder, and subjects suffering from a second psychiatric disorder), said method comprising: selecting subjects suffering from said first psychiatric disorder and subjects suffering second psychiatric disorder; measuring one or more ERG parameters in the subjects; and identifying the one or more ERG parameters (the individual parameters and/or combinations of parameters) that best discriminate between the subjects suffering from said first psychiatric disorder and the subjects suffering second psychiatric disorder.

In an embodiment, if said first psychiatric disorder is SZ, said second disorder is not BP.

In an embodiment, the method is for identifying one or more ERG parameters useful for the differential diagnosis of SZ and MDD or of a predisposition thereto, said method comprising: selecting a group of subjects suffering from SZ; selecting a group of subjects suffering from MDD; measuring one or more ERG parameters in the subjects; and identifying the one or more ERG parameters that permit to discriminate between the subjects suffering from SZ and those suffering from MDD.

In another embodiment, the method is for identifying one or more ERG parameters useful for the differential diagnosis of BP and MDD or a predisposition thereto, said method comprising: selecting a group of subjects suffering from BP; selecting a group of subjects suffering from MDD; measuring one or more ERG parameters in the subjects; and identifying the one or more ERG parameters that permit to discriminate between the subjects suffering from BP and those suffering from MDD.

In an embodiment, the identification of the one or more ERG parameters that best discriminate between the subjects suffering from the first psychiatric disorder and the subjects suffering the second psychiatric disorder includes processing or converting the raw target detection data (e.g., mathematically, statistically or otherwise) using a statistical method (e.g., logistic or logit regression, cluster analysis, ANCOVA) that takes into account subject data or other data such as age; gender; race; disease stage/phase, medication, etc. The algorithm may also take into account factors such as the presence, diagnosis and/or prognosis of a subject's condition other than the major psychiatric disorder. As will be clear to the skilled artisan to which the present invention pertains, from above and below, numerous combinations of data parameters and/or factors may be used by the algorithm or algorithms encompassed herein, to obtain the desired output. In an embodiment, the method comprises determining or identifying one or more logistic regression algorithms, based on the one or more ERG parameters (and optionally other variables such as age, gender, etc.), that permits to predict whether a subject suffer from a first or second psychiatric disorder.

Prediction of Response to Treatment

In the studies described herein, the present inventors have shown that certain ERG parameters permit to distinguish patients that respond to psychotropic medication (good responders, whose medical/clinical condition significantly improved following psychotropic medication) from patients who do not, or who poorly, respond to the psychotropic medication (whose medical/clinical condition showed little or no improvement following psychotropic medication).

Accordingly, in another aspect, the present invention provides a method for predicting if a subject suffering from a psychiatric disorder (e.g., SZ, BP) or having a predisposition thereto is likely to respond to a psychotropic medication, the method comprising measuring the cone a-wave amplitude and the rod a-wave implicit time by ERG in the subject, wherein (a)
- (i) a cone a-wave amplitude that is higher, and a rod a-wave implicit time that is lower, relative to the corresponding values in a control subject who do not respond to the psychotropic drug and/or
- (ii) a cone a-wave amplitude that is substantially similar or higher, and a rod a-wave implicit time that is substantially similar or lower, relative to the corresponding values in a control subject who responds to the psychotropic drug;
- is indicative that said subject's likelihood to respond to the psychotropic medication is more than about 50% (e.g., about 55%, 60%, 65%, 70%, 75%, 80%, 85%, 90% or more); and (b)
- (i) a cone a-wave amplitude that is lower, and a rod a-wave implicit time that is higher, relative to the corresponding values in a control subject who responds well to the psychotropic drug; and/or
- (ii) a cone a-wave amplitude that is substantially similar or lower, and a rod a-wave implicit time that is substantially similar or higher, relative to the corresponding values in a control subject who poorly responds to the psychotropic drug;
- is indicative that said subject's likelihood to respond to psychotropic medication is less than about 50% (e.g., about 45%, 40%, 35%, 30%, 25%, 20%, 15%, 10% or less).

In another aspect, the present invention provides the use of the above-mentioned ERG parameters (cone a-wave amplitude and the rod a-wave implicit time) for predicting if a subject suffering from a psychiatric disorder (e.g., SZ) or having a predisposition thereto is likely to respond to a psychotropic medication.

Psychotropic medication as used herein refers to drugs used for the management of mental and emotional disorders such as psychiatric disorders, and includes for example antidepressants, stimulants, antipsychotics, mood stabilizers (e.g., lithium), anxiolytics. In a further embodiment, the central core of the psychotropic medication comprises a thienobenzodiazepine, such as olanzapine (e.g., Zyprexa®). In another embodiment, the antipsychotic medication comprises quetiapine (e.g., Seroquel®). In another embodiment, the antipsychotic comprises aripiprazole (e.g., Abilify®). In another embodiment, the psychotropic medication does not comprise clozapine (e.g., Clozaril®). In another embodiment, the psychotropic medication is a mood stabilizer medication. In another embodiment, the mood stabilizer medication comprises lithium.

In another aspect, the present invention provides a method for predicting if a subject suffering from a psychiatric disorder (e.g., SZ) or having a predisposition thereto is likely to respond to olanzapine, the method comprising measuring the cone a-wave implicit time and the rod a-wave implicit time by ERG in the subject, wherein (a)
- (i) a cone a-wave amplitude that is similar or higher, and/or a rod a-wave implicit time that are is substantially similar or lower, relative to the corresponding value in a control subject who responds to olanzapine, or
- (ii) a cone a-wave amplitude that is higher and/or a rod a-wave implicit time that is lower, relative to the corresponding value in a control subject who do not respond to olanzapine;
- is indicative that said subject's likelihood to respond to olanzapine is more than 50%, and (b)
- (i) a cone a-wave amplitude that is similar or lower and/or a rod a-wave implicit time that is substantially similar or higher, relative to the corresponding value in a control subject who do not respond to olanzapine, or
- (ii) a cone a-wave amplitude that is lower and/or a rod a-wave implicit time that is higher, relative to the corresponding value in a control subject who responds to olanzapine
- is indicative that said subject's likelihood to respond to olanzapine is less than 50%.

In another aspect, the present invention provides the use of the above-mentioned ERG parameters (cone a-wave amplitude and rod a-wave implicit time) for predicting if a subject suffering from a psychiatric disorder (e.g., SZ) or having a predisposition thereto is likely to respond to olanzapine.

In another aspect, the present invention provides a method for predicting if a subject suffering from a psychiatric disorder (e.g., SZ) or having a predisposition thereto is likely to respond to quetiapine, the method comprising measuring the cone b-wave amplitude by ERG in the subject, wherein (a)
- (i) a cone b-wave amplitude that is substantially similar or higher, relative to the corresponding value in a control subject who responds to quetiapine, or
- (ii) a cone b-wave amplitude that is higher, relative to the corresponding value in a control subject who do not respond to quetiapine;
- is indicative that said subject's likelihood to respond to quetiapine is more than 50%, and (b)
- (i) a cone b-wave amplitude that is substantially similar or lower, relative to the corresponding value in a control subject who do not respond to quetiapine, or
- (ii) a cone b-wave amplitude that is lower, relative to the corresponding value in a control subject who responds to quetiapine
- is indicative that said subject's likelihood to respond to quetiapine is less than 50%.

In another aspect, the present invention provides the use of the above-mentioned ERG parameters (cone b-wave amplitude) for predicting if a subject suffering from a psychiatric disorder (e.g., SZ) or having a predisposition thereto is likely to respond to quetiapine.

In another aspect, the present invention provides a method for predicting if a subject suffering from a psychiatric disorder (e.g., SZ or BP) or having a predisposition thereto is likely to respond to quetiapine, the method comprising measuring the cone b-wave implicit time and the rod a-wave implicit time by ERG in the subject, wherein (a)
- (i) a cone b-wave implicit time and/or a rod a-wave implicit time that are substantially similar or higher, relative to the corresponding value in a control subject who responds to quetiapine, or (ii) a cone b-wave implicit time and/or a rod a-wave implicit time that are higher, relative to the corresponding value in a control subject who do not respond to quetiapine;
is indicative that said subject's likelihood to respond to quetiapine is more than 50%, and (b)
(i) a cone b-wave implicit time and/or a rod a-wave implicit time that are substantially similar or lower, relative to the corresponding value in a control subject who do not respond to quetiapine, or
(ii) a cone b-wave implicit time and/or a rod a-wave implicit time that are lower, relative to the corresponding value in a control subject who responds to quetiapine;
is indicative that said subject's likelihood to respond to quetiapine is less than 50%.

In another aspect, the present invention provides the use of the above-mentioned ERG parameters (cone b-wave implicit time and/or a rod a-wave implicit time) for predicting if a subject suffering from a psychiatric disorder (e.g., SZ or BP) or having a predisposition thereto is likely to respond to quetiapine.

In another aspect, the present invention provides a method for predicting if a subject suffering from a psychiatric disorder (e.g., SZ) or having a predisposition thereto is likely to respond to aripiprazole (trade name Abilify®), the method comprising measuring the rod a-wave amplitude by ERG in the subject, wherein (a)
(i) a rod a-wave amplitude that is substantially similar or lower, relative to the corresponding value in a in a control subject who responds to aripiprazole; or
(ii) a rod a-wave amplitude that is lower, relative to the corresponding value in a in a control subject who do not respond to aripiprazole;
is indicative that said subject's likelihood to respond to aripiprazole is more than 50%; and (b)
(i) a rod a-wave amplitude that is substantially similar or higher, relative to the corresponding values in a control subject who do not respond to aripiprazole; or
(ii) a rod a-wave amplitude that is higher, relative to the corresponding values in a control subject who responds to aripiprazole
is indicative that said subject's likelihood to respond to aripiprazole is less than 50%.

In another aspect, the present invention provides the use of the above-mentioned ERG parameter (rod a-wave amplitude) for predicting if a subject suffering from a psychiatric disorder (e.g., SZ) or having a predisposition thereto is likely to respond to aripiprazole (Abilify®).

In another aspect, the present invention provides a method for predicting if a subject suffering from a psychiatric disorder (e.g., BP) or having a predisposition thereto is likely to respond to lithium, the method comprising measuring the rod a-wave implicit time by ERG in the subject, wherein (a)
(i) a rod a-wave implicit time that is substantially similar or higher, relative to the corresponding value in a in a control subject who responds to lithium; or
(ii) a rod a-wave implicit time that is higher, relative to the corresponding value in a in a control subject who do not respond to lithium;
is indicative that said subject's likelihood to respond to lithium is more than 50%; and (b)
(i) a rod a-wave implicit time that is substantially similar or lower, relative to the corresponding values in a control subject who do not respond to lithium; or
(ii) a rod a-wave implicit time that is lower, relative to the corresponding values in a control subject who responds to lithium;
is indicative that said subject's likelihood to respond to lithium is less than 50%.

In another aspect, the present invention provides the use of the above-mentioned ERG parameter (rod a-wave implicit time) for predicting if a subject suffering from a psychiatric disorder (e.g., BP) or having a predisposition thereto is likely to respond to lithium.

In embodiments, the ERG values for one or more of the ERG parameters are subjected to one or more transformation analyses.

Accordingly, in another aspect, the present invention provides a method for predicting if a subject suffering from a psychiatric disorder or having a predisposition thereto is likely to respond to a psychotropic medication, the method comprising: (a) measuring one or more ERG parameters, in an embodiment one or more of the following ERG parameters, in the subject: the cone a-Wave amplitude, the cone a-Wave implicit time, the cone b-Wave amplitude, the cone b-Wave implicit time, the rod a-Wave amplitude, the rod a-Wave implicit time, rod b-Wave amplitude and the rod b-Wave implicit time, in the subject; (b) calculating a psychotropic medication response probability score by adjusting the value of one or more of the ERG parameters by one or more transformation analyses; and (c) determining whether the subject is likely to respond to the psychotropic medication based on the psychotropic medication response probability score.

In an embodiment, the psychiatric disorder is SZ. In an embodiment, the psychotropic medication comprises an antipsychotic.

In an embodiment, the one or more transformation analyses comprises logistic regression analysis, in a further embodiment the logistic regression analysis comprises (i) adjusting the value of one or more of the ERG parameters by an appropriate weighting coefficient to produce a weighted score for each ERG value, and (ii) combining the weighted score for each ERG value to generate the psychotropic medication probability score of more than 0.5 (or lower than 0.5). In an embodiment, the appropriate weighting coefficients (logistic regression algorithm) are determined based on the ERG parameter value(s) measured in a population of patients who respond to the psychotropic medication and in a population of patients who do not respond to the psychotropic medication. In an embodiment, the psychotropic medication response probability score is determined using a regression algorithm that includes age, gender, or both age and gender, as covariate.

In an embodiment, the psychotropic medication responsive probability score is determined using at least one of logistic regression models 1 or 2a-2h set forth in Table 6A.

In an embodiment, the method comprises measuring:
the cone a-Wave amplitude, and a psychotropic medication response probability score of more than 0.5 when calculated using a regression algorithm (see model 2a in Table 6A for the estimate of the coefficients) is indicative that subject is likely to respond to a psychotropic medication;
the cone a-Wave implicit time, and a psychotropic medication response probability score of more than 0.5 when calculated using a regression algorithm (see model 2b in Table 6A for the estimate of the coefficients) is indicative that subject is likely to respond to a psychotropic medication;

the cone b-Wave amplitude, and a psychotropic medication response probability score of more than 0.5 when calculated using a regression algorithm (see model 2c in Table 6A for the estimate of the coefficients) is indicative that subject is likely to respond to a psychotropic medication;

the cone b-Wave implicit time, and a psychotropic medication response probability score of more than 0.5 when calculated using a regression algorithm (see model 2d in Table 6A for the estimate of the coefficients) is indicative that subject is likely to respond to a psychotropic medication;

the rod a-Wave amplitude, and a psychotropic medication response probability score of more than 0.5 when calculated using a regression algorithm (see model 2e in Table 6A for the estimate of the coefficients) is indicative that subject is likely to respond to a psychotropic medication;

the rod a-Wave implicit time, and a psychotropic medication response probability score of more than 0.5 when calculated using a regression algorithm (see model 2f in Table 6A for the estimate of the coefficients) is indicative that subject is likely to respond to a psychotropic medication;

the rod b-Wave amplitude, and a psychotropic medication response probability score of more than 0.5 when calculated using a regression algorithm (see model 2g in Table 6A for the estimate of the coefficients) is indicative that subject is likely to respond to a psychotropic medication;

the rod b-Wave implicit time, and a psychotropic medication response probability score of more than 0.5 when calculated using a regression algorithm (see model 2h in Table 6A for the estimate of the coefficients) is indicative that subject is likely to respond to a psychotropic medication;

the rod a-Wave implicit time and the cone a-Wave amplitude, and a psychotropic medication response probability score of more than 0.5 when calculated using a regression algorithm of the formula below is indicative that subject is likely to respond to a psychotropic medication:

$$\text{Psychotropic medication response probability score} = \text{Exp}[4.08 - 0.03(\text{gender}) + 0.04(\text{age}) - 0.29(\text{scAlat}) + 0.10(\text{phAamp})]/(1 + \text{Exp}[4.08 - 0.03(\text{gender}) + 0.04(\text{age}) - 0.29(\text{scAlat}) + 0.10(\text{phAamp})])$$

in which

Gender=1 if the subject is a female and 0 if the subject is a male;

scAlat=rod a-Wave implicit time, flash intensity of 1 cd×s/m$^2$ (int2); and phAamp=cone a-Wave amplitude, fixed intensity of 7.5 cd×s/m$^2$ (int1).

In an embodiment, the central core of the psychotropic medication comprises a thienobenzodiazepine, preferably olanzapine. In another embodiment, the psychotropic medication does not comprise clozapine.

In an embodiment, the psychotropic medication responsive probability score is determined using at least one of logistic regression models 3 or 4a-4h or 5 set forth in Table 6A.

In an embodiment, method comprises measuring:

the cone a-Wave amplitude, and a psychotropic medication (olanzapine) response probability score of more than 0.5 when calculated using a regression algorithm (see model 4a in Table 6A for the estimate of the coefficients) is indicative that subject is likely to respond to the psychotropic medication (olanzapine);

the cone a-Wave implicit time, and a psychotropic medication (olanzapine) response probability score of more than 0.5 when calculated using a regression algorithm (see model 4b in Table 6A for the estimate of the coefficients) is indicative that subject is likely to respond to the psychotropic medication (olanzapine);

the cone b-Wave amplitude, and a psychotropic medication (olanzapine) response probability score of more than 0.5 when calculated using a regression algorithm (see model 4c in Table 6A for the estimate of the coefficients) is indicative that subject is likely to respond to the psychotropic medication (olanzapine);

the cone b-Wave implicit time, and a psychotropic medication (olanzapine) response probability score of more than 0.5 when calculated using a regression algorithm (see model 4d in Table 6A for the estimate of the coefficients) is indicative that subject is likely to respond to the psychotropic medication (olanzapine);

the rod a-Wave amplitude, and a psychotropic medication (olanzapine) response probability score of more than 0.5 when calculated using a regression algorithm (see model 4e in Table 6A for the estimate of the coefficients) is indicative that subject is likely to respond to the psychotropic medication (olanzapine);

the rod a-Wave implicit time, and a psychotropic medication (olanzapine) response probability score of more than 0.5 when calculated using a regression algorithm (see model 4f in Table 6A for the estimate of the coefficients) is indicative that subject is likely to respond to the psychotropic medication (olanzapine);

the rod b-Wave amplitude, and a psychotropic medication (olanzapine) response probability score of more than 0.5 when calculated using a regression algorithm (see model 4g in Table 6A for the estimate of the coefficients) is indicative that subject is likely to respond to the psychotropic medication (olanzapine);

the rod b-Wave implicit time, and a psychotropic medication (olanzapine) response probability score of more than 0.5 when calculated using a regression algorithm (see model 4h in Table 6A for the estimate of the coefficients) is indicative that subject is likely to respond to the psychotropic medication (olanzapine);

the rod a-Wave implicit time and the cone a-Wave amplitude, and a psychotropic medication (olanzapine) response probability score of more than 0.5 when calculated using a regression algorithm (see model 5 in Table 6A for the estimate of the coefficients) is indicative that subject is likely to respond to the psychotropic medication (olanzapine);

the rod a-Wave implicit time and the cone a-Wave amplitude, and a psychotropic medication (olanzapine) response probability score of more than 0.5 when calculated using a regression algorithm of the formula below is indicative that subject is likely to respond to the psychotropic medication (olanzapine):

$$\text{Psychotropic medication(olanzapine)response probability score} = \text{Exp}[754.71 - 42.44(\text{gender}) - 7.80(\text{age}) - 36.68(\text{scAlat}_{int2}) + 10.44(\text{phAamp}) + 9.51(\text{scAlat}_{vmax})]/(1 + \text{Exp}[754.71\ 42.44(\text{gender}) - 7.80(\text{age}) - 36.68(\text{scAlat}_{int2}) + 10.44(\text{phAamp}) + 9.51(\text{scAlat}_{vmax})])$$

in which

Gender=1 if the subject is a female and 0 if the subject is a male;

scAlat$_{int2}$=rod a-Wave implicit time, flash intensity of 1 cd×s/m² (int2);

phAamp=cone a-Wave amplitude, average of three intensities (13.33, 23/1 and 50 cd·s/m²; 3-int); and scAlat$_{vmax}$=rod a-Wave implicit time, peak maximal response (Vmax).

In another embodiment, the psychotropic medication comprises quetiapine. In another embodiment, the psychotropic medication does not comprise clozapine.

In an embodiment, the psychotropic medication response probability score is determined using at least one of logistic regression models 6 or 7a-7h set forth in Table 6A.

In an embodiment, the method comprises measuring:

the cone a-Wave amplitude, and a psychotropic medication (quetiapine) response probability score of more than 0.5 when calculated using a regression algorithm (see model 7a in Table 6A for the estimate of the coefficients) is indicative that subject is likely to respond to the psychotropic medication (quetiapine);

the cone a-Wave implicit time, and a psychotropic medication (quetiapine) response probability score of more than 0.5 when calculated using a regression algorithm (see model 7b in Table 6A for the estimate of the coefficients) is indicative that subject is likely to respond to the psychotropic medication (quetiapine);

the cone b-Wave amplitude, and a psychotropic medication (quetiapine) response probability score of more than 0.5 when calculated using a regression algorithm (see model 7c in Table 6A for the estimate of the coefficients) is indicative that subject is likely to respond to the psychotropic medication (quetiapine);

the cone b-Wave implicit time, and a psychotropic medication (quetiapine) response probability score of more than 0.5 when calculated using a regression algorithm (see model 7d in Table 6A for the estimate of the coefficients) is indicative that subject is likely to respond to the psychotropic medication (quetiapine);

the rod a-Wave amplitude, and a psychotropic medication (quetiapine) response probability score of more than 0.5 when calculated using a regression algorithm (see model 7e in Table 6A for the estimate of the coefficients) is indicative that subject is likely to respond to the psychotropic medication (quetiapine);

the rod a-Wave implicit time, and a psychotropic medication (quetiapine) response probability score of more than 0.5 when calculated using a regression algorithm (see model 7f in Table 6A for the estimate of the coefficients) is indicative that subject is likely to respond to the psychotropic medication (quetiapine);

the rod b-Wave amplitude, and a psychotropic medication (quetiapine) response probability score of more than 0.5 when calculated using a regression algorithm (see model 7g in Table 6A for the estimate of the coefficients) is indicative that subject is likely to respond to the psychotropic medication (quetiapine);

the rod b-Wave implicit time, and a psychotropic medication (quetiapine) response probability score of more than 0.5 when calculated using a regression algorithm (see model 7h in Table 6A for the estimate of the coefficients) is indicative that subject is likely to respond to the psychotropic medication (quetiapine);

the rod a-Wave amplitude and the cone b-Wave amplitude, and a psychotropic medication (quetiapine) response probability score of more than 0.5 when calculated using a regression algorithm of the formula below is indicative that subject is likely to respond to the psychotropic medication (quetiapine):

Psychotropic medication(quetiapine)response probability score=Exp[2.28−0.50(gender)−0.19(age)+0.34(phBamp)−0.61(scAamp)]/(1+Exp[2.28−0.50(gender)−0.19(age)+0.34(phBamp)−0.61(scAamp)])

in which

Gender=1 if the subject is a female and 0 if the subject is a male;

phBamp=cone b-Wave amplitude, fixed intensity of 7.5 cd×s/m² (int1); and scAamp=rod a-Wave amplitude, peak maximal response (Vmax).

In another embodiment, the psychotropic medication comprises aripiprazole (Abilify®). In another embodiment, the psychotropic medication does not comprise clozapine.

In an embodiment, the psychotropic medication response probability score is determined using at least one of logistic regression models 8 or 9a-9g set forth in Table 6A.

In an embodiment, the method comprises measuring:

the cone a-Wave amplitude, and a psychotropic medication (aripiprazole, Abilify®) response probability score of more than 0.5 when calculated using a regression algorithm (see model 9a in Table 6A for the estimate of the coefficients) is indicative that subject is likely to respond to the psychotropic medication (aripiprazole, Abilify®);

the cone a-Wave implicit time, and a psychotropic medication (aripiprazole, Abilify®) response probability score of more than 0.5 when calculated using a regression algorithm (see model 9b in Table 6A for the estimate of the coefficients) is indicative that subject is likely to respond to the psychotropic medication (aripiprazole, Abilify®);

the cone b-Wave amplitude, and a psychotropic medication (aripiprazole, Abilify®) response probability score of more than 0.5 when calculated using a regression algorithm (see model 9c in Table 6A for the estimate of the coefficients) is indicative that subject is likely to respond to the psychotropic medication (aripiprazole, Abilify®);

the cone b-Wave implicit time, and a psychotropic medication (aripiprazole, Abilify®) response probability score of more than 0.5 when calculated using a regression algorithm (see model 9d in Table 6A for the estimate of the coefficients) is indicative that subject is likely to respond to the psychotropic medication (aripiprazole, Abilify®);

the rod a-Wave amplitude, and a psychotropic medication (aripiprazole, Abilify®) response probability score of more than 0.5 when calculated using a regression algorithm (see model 8 in Table 6A for the estimate of the coefficients) is indicative that subject is likely to respond to the psychotropic medication (aripiprazole, Abilify®);

the rod a-Wave implicit time, and a psychotropic medication (aripiprazole, Abilify®) response probability score of more than 0.5 when calculated using a regression algorithm (see model 9e in Table 6A for the estimate of the coefficients) is indicative that subject is likely to respond to the psychotropic medication (aripiprazole, Abilify®);

the rod b-Wave amplitude, and a psychotropic medication (aripiprazole, Abilify®) response probability score of more than 0.5 when calculated using a regression algorithm (see model 9f in Table 6A for the estimate of the coefficients) is indicative that subject is likely to respond to the psychotropic medication (aripiprazole, Abilify®);

the rod b-Wave implicit time, and a psychotropic medication (aripiprazole, Abilify®) response probability score of more than 0.5 when calculated using a regression algorithm (see model 9g in Table 6A for the estimate of the coefficients) is indicative that subject is likely to respond to the psychotropic medication; or In an embodiment, the psychiatric disorder is SZ or BR In an embodiment, the psychotropic medication comprises an antipsychotic.

In an embodiment, the central core of the psychotropic medication comprises quetiapine. In another embodiment, the psychotropic medication does not comprise clozapine.

In an embodiment, the psychotropic medication responsive probability score is determined using at least one of logistic regression models 15, 16a-16h, 17, 18 or 19 set forth in Table 20A.

In an embodiment, method comprises measuring:

the cone a-Wave amplitude, and a psychotropic medication (quetiapine) response probability score of more than 0.5 when calculated using a regression algorithm (see model 16a in Table 20A for the estimate of the coefficients) is indicative that subject is likely to respond to the psychotropic medication (quetiapine);

the cone a-Wave implicit time, and a psychotropic medication (quetiapine) response probability score of more than 0.5 when calculated using a regression algorithm (see model 16b in Table 20A for the estimate of the coefficients) is indicative that subject is likely to respond to the psychotropic medication (quetiapine);

the cone b-Wave amplitude, and a psychotropic medication (quetiapine) response probability score of more than 0.5 when calculated using a regression algorithm (see model 16c in Table 20A for the estimate of the coefficients) is indicative that subject is likely to respond to the psychotropic medication (quetiapine);

the cone b-Wave implicit time, and a psychotropic medication (quetiapine) response probability score of more than 0.5 when calculated using a regression algorithm (see model 16d in Table 20A for the estimate of the coefficients) is indicative that subject is likely to respond to the psychotropic medication (quetiapine);

the rod a-Wave amplitude, and a psychotropic medication (quetiapine) response probability score of more than 0.5 when calculated using a regression algorithm (see model 16e in Table 20A for the estimate of the coefficients) is indicative that subject is likely to respond to the psychotropic medication (quetiapine);

the rod a-Wave implicit time, and a psychotropic medication (quetiapine) response probability score of more than 0.5 when calculated using a regression algorithm (see model 16f in Table 20A for the estimate of the coefficients) is indicative that subject is likely to respond to the psychotropic medication (quetiapine);

the rod b-Wave amplitude, and a psychotropic medication (quetiapine) response probability score of more than 0.5 when calculated using a regression algorithm (see model 16g in Table 20A for the estimate of the coefficients) is indicative that subject is likely to respond to the psychotropic medication (quetiapine);

the rod b-Wave implicit time, and a psychotropic medication (quetiapine) response probability score of more than 0.5 when calculated using a regression algorithm (see model 16h in Table 20A for the estimate of the coefficients) is indicative that subject is likely to respond to the psychotropic medication (quetiapine);

the cone b-Wave implicit time and rod b-Wave implicit time, and a psychotropic medication (quetiapine) response probability score of more than 0.5 when calculated using a regression algorithm (see model 17 in Table 20A for the estimate of the coefficients) is indicative that subject is likely to respond to the psychotropic medication (quetiapine);

the cone a-Wave amplitude and rod b-Wave implicit time, and a psychotropic medication (quetiapine) response probability score of more than 0.5 when calculated using a regression algorithm (see model 18 in Table 20A for the estimate of the coefficients) is indicative that subject is likely to respond to the psychotropic medication (quetiapine);

the cone a-Wave amplitude, rod a-Wave implicit time and rod b-Wave implicit time, and a psychotropic medication (quetiapine) response probability score of more than 0.5 when calculated using a regression algorithm (see model 19 in Table 20A for the estimate of the coefficients) is indicative that subject is likely to respond to the psychotropic medication (quetiapine);

the cone a-wave amplitude, cone b-wave amplitude, rod a-Wave implicit time, rod b-Wave amplitude and the rod b-Wave implicit time, and a psychotropic medication (quetiapine) response probability score of more than 0.5 when calculated using a regression algorithm of the formula below is indicative that subject is likely to respond to the psychotropic medication (quetiapine):

$$\text{Psychotropic medication(quetiapine)response probability score} = \text{Exp}[-69.38 - 2.73(\text{gender}) - 0.44(\text{age}) + 0.69(\text{phAamp}) - 0.31(\text{phBamp}) + 4.61(\text{scAlat}) + 0.15(\text{scBamp}) - 0.66(\text{scBlat})]/(1 + \text{Exp}[-69.38 - 2.73(\text{gender}) - 0.44(\text{age}) + 0.69(\text{phAamp}) - 0.31(\text{phBamp}) + 4.61(\text{scAlat}) + 0.15(\text{scBamp}) - 0.66(\text{scBlat})])$$

in which

Gender=1 if the subject is a female and 0 if the subject is a male;

phAamp=cone a-Wave amplitude, peak maximal response (Vmax);

phBamp=cone b-Wave amplitude, fixed intensity of 7.5 cd×s/m² (int1);

scAlat=rod a-Wave implicit time, fixed intensity of 1 cd×s/m² (int2);

scBamp=rod b-Wave amplitude, peak maximal response (Vmax);

scBlat=rod b-Wave implicit time, fixed intensity of 1 cd×s/m² (int2).

In an embodiment, the psychiatric disorder is BP. In an embodiment, the psychotropic medication comprises a mood stabilizer (e.g., lithium). In an embodiment, the central core of the psychotropic medication comprises lithium. In another embodiment, the psychotropic medication does not comprise clozapine.

In an embodiment, the psychotropic medication responsive probability score is determined using at least one of logistic regression models 10, 11a-11h, 12, 13 or 14 set forth in Table 18A.

In an embodiment, method comprises measuring:

the cone a-Wave amplitude, and a psychotropic medication (lithium) response probability score of more than 0.5 when calculated using a regression algorithm (see model 11a in Table 18A for the estimate of the coefficients) is indicative that subject is likely to respond to the psychotropic medication (lithium);

the cone a-Wave implicit time, and a psychotropic medication (lithium) response probability score of more than 0.5 when calculated using a regression algorithm (see model 11b in Table 18A for the estimate of the coefficients) is indicative that subject is likely to respond to the psychotropic medication (lithium);

the cone b-Wave amplitude, and a psychotropic medication (lithium) response probability score of more than 0.5 when calculated using a regression algorithm (see model 11c in Table 18A for the estimate of the coefficients) is indicative that subject is likely to respond to the psychotropic medication (lithium);

the cone b-Wave implicit time, and a psychotropic medication (lithium) response probability score of more than 0.5 when calculated using a regression algorithm (see model 11*d* in Table 18A for the estimate of the coefficients) is indicative that subject is likely to respond to the psychotropic medication (lithium);

the rod a-Wave amplitude, and a psychotropic medication (lithium) response probability score of more than 0.5 when calculated using a regression algorithm (see model 11*e* in Table 18A for the estimate of the coefficients) is indicative that subject is likely to respond to the psychotropic medication (lithium);

the rod a-Wave implicit time, and a psychotropic medication (lithium) response probability score of more than 0.5 when calculated using a regression algorithm (see model 11*f* in Table 18A for the estimate of the coefficients) is indicative that subject is likely to respond to the psychotropic medication (lithium);

the rod b-Wave amplitude, and a psychotropic medication (lithium) response probability score of more than 0.5 when calculated using a regression algorithm (see model 11*g* in Table 18A for the estimate of the coefficients) is indicative that subject is likely to respond to the psychotropic medication (lithium);

the rod b-Wave implicit time, and a psychotropic medication (lithium) response probability score of more than 0.5 when calculated using a regression algorithm (see model 11*h* in Table 18A for the estimate of the coefficients) is indicative that subject is likely to respond to the psychotropic medication (lithium);

the rod b-Wave amplitude at both intensities, and a psychotropic medication (lithium) response probability score of more than 0.5 when calculated using a regression algorithm (see model 12 in Table 18A for the estimate of the coefficients) is indicative that subject is likely to respond to the psychotropic medication (lithium);

the rod b-Wave amplitude at both intensities and the rod b-wave implicit time, and a psychotropic medication (lithium) response probability score of more than 0.5 when calculated using a regression algorithm (see model 13 in Table 18A for the estimate of the coefficients) is indicative that subject is likely to respond to the psychotropic medication (lithium);

the cone a-Wave amplitude, the cone b-wave implicit time at both intensities and the rod a-wave implicit time, and a psychotropic medication (lithium) response probability score of more than 0.5 when calculated using a regression algorithm (see model 14 in Table 18A for the estimate of the coefficients) is indicative that subject is likely to respond to the psychotropic medication (lithium);

the cone a-Wave amplitude, the cone a-Wave implicit time and the cone b-wave implicit time at both intensities and the rod a-Wave implicit time, and a psychotropic medication (lithium) response probability score of more than 0.5 when calculated using a regression algorithm of the formula below is indicative that subject is likely to respond to the psychotropic medication (lithium):

$$\text{Psychotropic medication(lithium)response probability score} = \text{Exp}[-61.12 + 3.12(\text{gender}) + 0.10(\text{age}) + 0.16(\text{phAamp}) + 1.05(\text{phAlat}) - 2.49(\text{phBlat}_{vmax}) + 0.77(\text{phBlat}_{3int}) + 3.17(\text{scAlat})]/(1 + \text{Exp}[-61.12 + 3.12(\text{gender}) + 0.10(\text{age}) + 0.16(\text{phAamp}) + 1.05(\text{phAlat}) - 2.49(\text{phBlat}_{vmax}) + 0.77(\text{phBlat}_{3int}) + 3.17(\text{scAlat})])$$

in which

Gender=1 if the subject is a female and 0 if the subject is a male;

phAamp=cone a-Wave amplitude, peak maximal response (Vmax);

phAlat=cone a-Wave implicit time, flash intensity of 7.5 cd×s/m² (int1);

phBlat$_{vmax}$=cone b-Wave implicit time, peak maximal response (Vmax);

phBlat$_{3int}$=cone b-Wave implicit time, average of three intensities (13.33, 23.71 and 50 cd·s/m²; 3-int); and scAlat=rod a-Wave implicit time, flash intensity of 1 cd×s/m² (int2).

In another aspect, the present invention provides a method for identifying one or more ERG parameters useful for discriminating between subjects suffering from a psychiatric disorder (e.g., a major psychiatric disorder such as SZ) having a likelihood to respond to a psychotropic drug of more than 50% (subjects who will be good responders), and subjects suffering from a psychiatric disorder having a likelihood to respond to a psychotropic medication of less than 50% (subjects who will be poor or non-responders), said method comprising:

administering the psychotropic drug to a group of subjects;

determining whether the subjects have responded to the psychotropic drug;

measuring one or more ERG parameters in the subjects; and identifying the one or more ERG parameters that best discriminate between the subjects who responded to the psychotropic medication and the subjects who did not respond (or who responded poorly) to the psychotropic drug.

In an embodiment, the identification of the one or more ERG parameters that best discriminate between the subjects who responded to the psychotropic drug and the subjects who did not respond to the psychotropic drug includes processing or converting the raw target detection data (e.g., mathematically, statistically or otherwise) using a statistical method (e.g., logistic or logit regression, cluster analysis, ANCOVA) that takes into account subject data or other data such as age; race; disease stage/phase, medication, etc. The algorithm may also take into account factors such as the presence, diagnosis and/or prognosis of a subject's condition other than the major psychiatric disorder. As will be clear to the skilled artisan to which the present invention pertains, from above and below, numerous combinations of data parameters and/or factors may be used by the algorithm or algorithms encompassed herein, to obtain the desired output. In an embodiment, the method comprises determining or identifying one or more logistic regression algorithms, based on the one or more ERG parameters (and optionally other variables such as age, gender, etc.), that permits to predict whether a subject will respond to psychotropic medication or not.

Methods of Stratification

In the studies described herein, the present inventors have shown that certain ERG parameters permit to identify different group of SZ patients with shared biological/clinical characteristics.

In another aspect, the present invention provides a method for the stratification of a subject suffering from a major psychiatric disorder (e.g., SZ), said method comprising measuring ERG parameters, in an embodiment (i) the cone b-wave implicit time, (ii) the rod a-wave implicit time, (iii) the rod b-wave amplitude, (iv) the cone a-wave amplitude, (v) the cone a-wave implicit time, and (vi) the rod b-wave implicit time, in said subject, wherein:

(a) a rod a-wave implicit time and/or a cone a-wave implicit time that is/are lower (e.g., less than about 1SD) relative to the corresponding value(s) in a control subject (not suffering from a major psychiatric disorder, e.g., SZ) defines a first group of stratification;
(b) a rod b-wave implicit time that is higher (e.g., more than about 1 SD or 1.5SD) relative to the corresponding value in a control subject defines a second group of stratification;
(c) a cone b-wave implicit time that is higher and a rod b-wave implicit time that is substantially similar relative to the corresponding values in a control subject defines a third group of stratification;
(d) a cone b-wave implicit time that is substantially similar relative to the corresponding value in a control subject defines a fourth group of stratification.

In an embodiment, the first group of stratification is further defined by a cone b-wave implicit time that is higher (e.g., more than about 1SD) relative to the corresponding values in a control subject. In an embodiment, the first group of stratification is further defined by a rod b-wave amplitude, a cone a-wave amplitude and a rod b-wave implicit time that are substantially similar or slightly lower (e.g., less than about 0.5SD lower) relative to the corresponding values in a control subject. In another embodiment, the first group of stratification is further defined by a lower global IQ, a lower visual episodic memory and a lower working memory relative to control subjects and to subjects from the other groups of stratification. In another embodiment, the first group of stratification is further defined by a better improvement of overall functioning (relative to the other stratification groups), as measured according to the Global Assessment Scale severity (GAS-S) and/or Global Assessment Scale functionality (GAS-F), following treatment with antipsychotic medication.

In an embodiment, the second group of stratification is further defined by a cone b-wave implicit time and a rod b-Wave implicit time that are higher (e.g., more than about 1.5SD, 2SD, 2.5SD or 3SD higher) relative to the corresponding values in a control subject. In an embodiment, the second group of stratification is further defined by rod b-wave amplitude and a cone a-wave amplitude that are lower (e.g., more than about 0.5 or 1SD lower) relative to the corresponding values in a control subject. In an embodiment, the second group of stratification is further defined by a rod a-wave implicit time and a cone a-wave implicit time that are substantially similar or slightly lower (less than about 0.5SD lower) relative to the corresponding values in a control subject.

In an embodiment, the third group of stratification is further defined by a cone b-wave implicit time that is higher (e.g., more than about 2SD or higher) relative to the corresponding values in a control subject. In an embodiment, the third group of stratification is further defined by a rod a-wave implicit time, a cone a-Wave implicit time and a rod b-Wave implicit time that are substantially similar (e.g., within 0.5SD) relative to the corresponding values in a control subject. In an embodiment, the third group of stratification is further defined by a rod b-wave amplitude and a cone a-wave amplitude that are lower (e.g., more than about 0.5SD lower) relative to the corresponding values in a control subject.

In another embodiment, the second and third groups of stratification are further by a poorer improvement of overall functioning (relative to the other stratification groups), as measured according to the Global Assessment Scale severity (GAS-S), the Global Assessment Scale functionality (GAS-F) and/or the Positive and Negative Syndrome Scale (PANSS) severity, following treatment with antipsychotic medication.

In an embodiment, the fourth group of stratification is further defined by a rod a-wave implicit time, a rod b-wave amplitude, a cone a-wave amplitude, a cone a-wave implicit time and a rod b-wave implicit time that are substantially similar or slightly lower (e.g., within 0.5SD or 0.3SD) relative to the corresponding values in a control subject.

In another embodiment, the fourth group of stratification is further defined by a higher/better processing speed relative to the first, second and third groups of stratification.

In the studies described herein, the present inventors have also shown that certain ERG parameters permit to identify different group of BP patients with shared biological/clinical characteristics.

In another aspect, the present invention provides a method for the stratification of a subject suffering from a major psychiatric disorder (e.g., BP), said method comprising measuring (i) the cone b-wave implicit time, (ii) the rod a-wave implicit time, (iii) the rod b-wave amplitude, (iv) the cone a-wave amplitude, (v) the cone a-wave implicit time, and (vi) the rod b-wave implicit time and/or (vii) the cone b-wave amplitude, in said subject, wherein:
(a) a rod b-wave amplitude, a cone a-wave amplitude and/or a cone b-wave amplitude that is/are lower (e.g., less than about 0.5 SD or 1SD), and/or a rod a-wave implicit time that is higher (more than about 0.5, 1 or 1.5SD) relative to the corresponding value(s) in a control subject (not suffering from a major psychiatric disorder, e.g., BP) defines a first group of stratification;
(b) a rod a-wave implicit time that is lower (e.g., less than about 0.5SD) relative to the corresponding value in a control subject defines a second group of stratification.

In an embodiment, the first group of stratification is further defined by a cone b-wave implicit time that is higher (more than about 1, 1.5 or 2SD) relative to the corresponding value(s) in a control subject, and/or a rod a-wave implicit time and/or a cone a-wave implicit time that are substantially similar (within about 0.5SD) relative to the corresponding value(s) in a control subject.

In an embodiment, the second group of stratification is further defined by a cone b-wave implicit time that is higher (more than about 0.5 or 1SD) relative to the corresponding value(s) in a control subject, and/or a rod b-wave amplitude, a cone a-wave amplitude, a cone a-wave implicit time, a rod b-wave implicit time and/or a cone b-wave amplitude that are substantially similar (within about 0.5SD) relative to the corresponding value(s) in a control subject.

Patient/Treatment Monitoring and Drug Screening

The assessment of ERG parameters may also be used for monitoring the condition of a psychiatric disorder in a subject having such a disorder, or of being predisposed thereto, for example for monitoring the efficacy of a therapy (either an existing therapy or a new therapy, e.g., during clinical trial) for psychiatric disorder.

Thus, in another aspect, the present invention provides a method for monitoring a patient's condition (e.g., for determining whether the patient's condition is improving or not following treatment, whether the patient is responding or not to the medication) in a patient suffering from or predisposed to a psychiatric disorder, the method comprising measuring one or more ERG parameters in the subject at a first time point (e.g., prior to administration of the medication, or at an earlier stage of the disease or therapy) and at a second (later) time point (e.g., after administration of the medication, or at a later stage of the disease or therapy), comparing the one or more ERG parameters obtained at the first and second time points to each other and/or to a control, wherein a normalization of one or more of the ERG parameters at the second time point is indicative that the patient's condition is improving (e.g., that the patient is responding to the medication), and wherein the absence of normalization of at least one ERG parameters at the second time point is indicative that the patient's condition is not improving (e.g., that the patient is not or poorly responding to the medication). "Normalization" as used herein refers to an ERG parameter that is more similar to an ERG parameter measured in a "healthy" subject (not suffering from or predisposed to a psychiatric disorder). For example, assuming that a given ERG parameter measured at the first time point is 3SD higher than the ERG parameter measured in a "healthy" subject, a value that is 0.5 or 1SD higher than the ERG parameter measured in a "healthy" subject at the second time point is considered a "normalization" of the ERG parameter.

In embodiments, the ERG values for one or more of the ERG parameters are subjected to one or more transformation analyses. According, in another aspect, the present invention provides a method of monitoring the response to a treatment in subject suffering from a major psychiatric disorder, said method comprising: (a) measuring one or more ERG parameters in the subject at a first, earlier time point and at a second, later time point, wherein said subject is treated between said first and second time points; (b) calculating major psychiatric disorder probability scores at said first and second time points by adjusting the value of one or more of the ERG parameters by one or more transformation analyses; and (c) monitoring the response to the treatment in the subject based on the major psychiatric disorder probability scores at said first and second time points. In another aspect, the present invention provides method of monitoring the condition of a subject suffering from a major psychiatric disorder, said method comprising: (a) measuring one or more ERG parameters in the subject at a first, earlier time point and at a second, later time point; (b) calculating major psychiatric disorder probability scores at said first and second time points by adjusting the value of one or more of the ERG parameters by one or more transformation analyses; (c) monitoring the condition the subject based on the major psychiatric disorder probability scores at said first and second time points.

In an embodiment, the one or more transformation analyses comprises logistic regression analysis, in a further embodiment the logistic regression analysis comprises (i) adjusting the value of one or more of the ERG parameters by an appropriate weighting coefficient to produce a weighted score for each ERG value, and (ii) combining the weighted score for each ERG value to generate the major psychiatric disorder probability score. In an embodiment, the appropriate weighting coefficients are determined based on the ERG parameter value(s) measured in a population of patients who suffers from a major psychiatric disorder and in a population of patients who do not suffer major psychiatric disorder. In an embodiment, the major psychiatric disorder probability score is determined using a regression algorithm that includes age, gender, or both age and gender, as covariate. It will be understood that: a decrease in the major psychiatric disorder probability score between said first and second time points is indicative that the subject is responsive to the treatment (that the patient's condition is improving): a stabilization or an increase in the major psychiatric disorder probability score between said first and second time points is indicative that the subject is not responsive to the treatment (that the patient's condition is not improving).

The monitoring may be performed at several occasions during the therapy. The time elapsed between the ERG measurements in the subject undergoing diagnosis or monitoring may be few days (e.g., 3 days, 5 days), a week, two weeks, a month, 2 months, 3 months, 6 months, 12 months, 2 years, 4 years, etc. ERG measurements may be performed prior to and/or during and/or following a therapy. ERG measurements may be performed at intervals over the remaining life, or a part thereof, of a subject.

Such method for monitoring efficacy of a therapy may be used, for example, for drug screening or in clinical trials, to monitor the therapeutic effectiveness of existing therapies and new therapies in human subjects, and may be incorporated into screens for new drug substances and combinations of substances.

Methods of Treatment

In an embodiment, the above-mentioned method further comprises selecting and/or administering a course of therapy or prophylaxis to said subject in accordance with the diagnostic, prognostic, prediction, stratification and/or monitoring result.

Thus, in another aspect, the present invention provides a method comprising detecting a psychiatric disorder or a predisposition thereto in a subject using the methods defined above, and if said subject has a psychiatric disorder or a predisposition thereto, treating the psychiatric disorder, for example by administering an appropriate psychotropic medication to the subject. For example, if it is determined based on the methods described herein that the subject suffers from SZ, or has a predisposition thereto, the method comprises administration of suitable medication for treatment for the treatment of SZ or for preventing the development of SZ. Alternatively, if it is determined based on the methods described herein that the subject suffers from BP, or has a predisposition thereto, the method comprises administration of suitable medication for treatment for the treatment of BP or for preventing the development of BP. Alternatively, if it is determined based on the methods described herein that the subject suffers from MDD, or has a predisposition thereto, the method comprises administration of suitable medication for treatment for the treatment of MDD or for preventing the development of MDD. Alternatively, if it is determined based on the methods described herein that the subject does not suffer from a psychiatric disorder or a predisposition thereto, the method comprises further evaluating the subject to determine his medical condition.

In another aspect, the present invention provides a method comprising monitoring a treatment (e.g., determining whether the patient's condition is improving or not following treatment, whether the patient is responding or not to the medication) in a patient suffering from or predisposed to a psychiatric disorder using the methods defined above, and if said patient's condition is improving, continue administering the same psychotropic medication to the subject. Alternatively, if the patient's condition is not improving, modifying the therapy (e.g., administering a different psychotropic medication or a combination of drugs to the subject, or modifying the dosage regimen).

In another aspect, the present invention provides a method comprising determining whether a subject suffering from a psychiatric disorder (e.g., SZ, BP, MDD) or having a predisposition thereto is likely to respond to a psychotropic medication using the method defined above, and if said subject is likely to respond to a psychotropic medication, administering the psychotropic medication to the subject. Alternatively, if the subject is not likely to respond to a psychotropic medication, administering a different psychotropic medication to the subject.

Use of Computers, Computer Programs

In an embodiment, one or more steps of the above-mentioned methods are performed using or by a computer (e.g., using computer algorithms), using a suitably programmed computer. According to various embodiments, the method can further comprise measuring one or more ERG parameters in a subject. In an embodiment, the ERG parameter value(s) obtained can subsequently be stored in a computer in a suitable computer readable form. The computer can subsequently be used to analyze the data and compare then to a control, determine an algorithm, apply the algorithm, etc. The data or results can then be displayed, for example, on a monitor, and/or printed. In embodiments, the methods further comprise transmitting the data or results over a communication network. For example, the data or results may be transferred from a laboratory testing facility (e.g., diagnostic laboratory) to a health care provider, who may analyse the data/results and/or choose the appropriate course of action based on the data/results (e.g., initiate therapy, continue therapy, interrupt therapy, modify the therapy, etc.).

In another embodiment, measuring the ERG of the present invention can include processing or converting the raw target detection data (e.g., mathematically, statistically or otherwise) using a statistical method (e.g., logistic or logit regression, cluster analysis, ANCOVA) that takes into account subject data or other data. Subject data may include (but is not limited to): age; race; disease stage/phase, medication, etc. The algorithm may also take into account factors such as the presence, diagnosis and/or prognosis of a subject's condition other than the major psychiatric disorder. As will be clear to the skilled artisan to which the present invention pertains, from above and below, numerous combinations of data parameters and/or factors may be used by the algorithm or algorithms encompassed herein, to obtain the desired output.

In accordance with the present invention, performing a "mathematical correlation", "mathematical transformation", "statistical method", or "clinical assessment algorithm" refers to any computational method or machine learning approach (or combinations thereof) that help associate the ERG parameter(s) with a clinical assessment of a psychiatric disorder, such as predicting, for example, the results of patient psychological evaluation or assessing the need to perform a patient psychological evaluation. A person of ordinary skill in the art will appreciate that different computational methods/tools may be selected for providing the mathematical correlations of the present invention, such as logistic regression (e.g., logistic regression such as multiple stepwise logistic regression), neural network, linear and quadratic discriminant analysis (LQA and QDA), Naïve Bayes, Random Forest and Support Vector Machines.

In one embodiment, the mathematical correlation can produce a range of output clinical assessment values that comprise a continuous or near-continuous range of values. Alternatively, the clinical assessment algorithm may produce a range of output clinical assessment values that comprise a range of discrete values. In a particular embodiment, the range of output clinical assessment values is two discrete values, such as two clinical assessment values selected from or clinically similar to the following group: "predisposed" and "not predisposed"; "µl" and "normal"; SZ or BP or MDD; "responsive to treatment" or "not responsive to treatment" and other two level output clinical assessment relevant to a clinical assessment of a major psychiatric disorder patient (or at risk). Of course, it will be understood that other such two clinical assessment values can be easily chosen by the skilled artisan using the methods of the present invention.

In another embodiment, the clinical assessment algorithm may compare one or more of the measured ERG parameters to one or more thresholds or control values (e.g., to classify them into two or more discrete clinical assessment values), or threshold probability score. In a particular embodiment, the threshold can enable classification into two or more discrete clinical assessment values relating to: afflicted with major psychiatric disorder (or predisposed thereto) or not; afflicted with a particular major psychiatric disorder (e.g., SZ) versus another (e.g., BP) or vs. another condition; likelihood of a therapy being successful; stratification into a group of patients exhibiting a certain profile (e.g., clinical profile). For example, a first clinical assessment value of "likely schizophrenia", "likely bipolar disorder", "likely to respond" to a particular antipsychotic medication, may correspond to an ERG parameter value or probability score (or a combination thereof) being below a first threshold, and a second clinical assessment value of "moderately likely schizophrenia", "moderately likely bipolar disorder" or "moderately likely to respond" to the antipsychotic medication, may correspond to an ERG parameter value or probability score (or a combination thereof) above a first threshold but below a second threshold. Accordingly, a third clinical assessment value of "unlikely schizophrenia", "unlikely bipolar disorder" or "unlikely to respond" to that antipsychotic medication may correspond to an ERG parameter value or probability score (or a combination thereof) which is above the second threshold.

In particular embodiments, the threshold values may be based on previous, and potentially current, testing of ERG parameters, known as positive or negative "control measurements" from individuals with a confirmed diagnosis of a major psychiatric disorder, and from other individuals such as those with other diseases/disorders as well as healthy individuals. Determining the ERG parameters by testing known healthy individuals and subjects with a confirmed diagnosis of a major psychiatric disorder allows the clinical assessment algorithm to identify the deterministic values for one or more thresholds, particularly as they relate to thresholds for determining whether the subject suffers from a major psychiatric disorder. Thresholds may also be determined based on testing of control samples from individuals with a known history of one or more of: disease evolution/progression; clinical success with one or more specific therapies such as a specific antipsychotic medication; and other known clinical outcomes. Alternatively or additionally, thresholds may be determined by ERG measurements made in the same subject at an earlier time point.

In another embodiment, the present invention can be used to monitor individuals who are otherwise susceptible, i.e., individuals who have been identified as genetically predisposed to a major psychiatric disorder (e.g., by genetic screening and/or family histories). Advancements in the understanding of genetics and developments in technology/epidemiology enable improved probabilities and risk assessments relating to major psychiatric disorders. Using family health histories and/or genetic screening, it is possible to estimate the probability that a particular individual has for developing certain types of major psychiatric disorders including SZ or BP. Those individuals that have been identified as being predisposed to developing a particular major psychiatric disorder can be monitored or screened to detect evidence of the development or evolution of major psychiatric disorder. Upon discovery of such evidence, early treatment can be undertaken to combat the disease.

In another embodiment, the clinical assessment of a psychiatric disorder in accordance with the present invention can further enable or include determining the particular or more suitable therapy that is to be given to a subject after the clinical assessment has been provided.

In another aspect, the present invention provides a program storage device readable by an electronic medium and tangibly storing instructions executable by the electronic medium to perform the one or more transformation analyses defined herein.

In another aspect, the present invention provides a computer program product comprising a computer useable medium that tangibly stores as computer readable code instructions to perform the one or more transformation analyses defined herein.

In another aspect, the present invention provides a computer-readable medium comprising code for controlling one or more processors to classify whether one or more ERG parameters measured in a subject is/are associated with a psychiatric disorder, said code comprising: instructions to apply a statistical process to a data set comprising a one or more ERG parameter value(s) to produce a statistically derived decision classifying said value(s) as psychiatric disorder (e.g., SZ or BP) value(s) or non-psychiatric disorder value(s).

In another aspect, the present invention provides a computer-readable medium comprising code for controlling one or more processors to perform the above-mentioned methods or any part of these methods.

In another aspect, the present invention provides a computer-readable medium comprising code for controlling one or more processors to classify whether one or more ERG parameters measured in a subject is/are associated with a response to a medication (antipsychotic medication) or not, said code comprising: instructions to apply a statistical process to a data set comprising a one or more ERG parameter value(s) to produce a statistically derived decision classifying said value(s) as responsive to a medication value(s) or non-responsive to a medication value(s).

In another aspect, the present invention provides a system for performing the above-mentioned methods, or any part of these methods.

In another aspect, the present invention provides a system for performing the one or more transformation analyses defined herein, said system comprising: (a) a data acquisition module configured to produce a data set comprising one or more ERG parameter value(s); (b) a data processing module configured to process the data set by applying one or more transformation analyses to the data set to produce a statistically derived probability score; and (c) a display module configured to display the statistically derived probability score.

In another aspect, the present invention provides a system for classifying whether one or more ERG parameters measured in a subject is/are associated with a psychiatric disorder, said system comprising: (a) a data acquisition module configured to produce a data set comprising one or more ERG parameter value(s); (b) a data processing module configured to process the data set by applying a statistical process to the data set to produce a statistically derived decision classifying said one or more ERG parameter value(s) as a psychiatric disorder (e.g., SZ or BP) value(s) or non-psychiatric disorder value(s); and (c) a display module configured to display the statistically derived decision.

In another aspect, the present invention provides a system for classifying whether one or more ERG parameters measured in a subject is/are associated with a response to a medication (antipsychotic medication) or not, said system comprising: (a) a data acquisition module configured to produce a data set comprising one or more ERG parameter value(s); (b) a data processing module configured to process the data set by applying a statistical process to the data set to produce a statistically derived decision classifying said one or more ERG parameter value(s) as responsive to a medication value(s) or non-responsive to a medication value(s); and (c) a display module configured to display the statistically derived decision.

MODE(S) FOR CARRYING OUT THE INVENTION

The present invention is illustrated in further details by the following non-limiting examples.

Example 1: Materials and Methods

Study Subjects for the Schizophrenia Studies.

The characteristics of the affected SZ patients and control subjects, are depicted in Table 1

TABLE 1

| Characteristics of the sample: 150 SZ cases and 150 controls | | |
|---|---|---|
| | SZ cases (N = 150) | Controls (N = 150) |
| | Mean (SD) or N (%) | |
| Age | 39.4 (9.9) | 40.6 (9.5) |
| % Male* | 80.7 | 62 |
| Age of onset | 25.0 (6.4) | — |
| Duration of illness | 13.7 (9.3) | — |
| IQ$^{b,*}$ | 82.6 (12.9) | 102.9 (11.7) |
| GAS-S (T3)$^a$ | 52.5 (8.8) | — |
| GAS-S (T1)$^a$ | 29.3 (10.1) | — |
| Olanzapine | 28 (19%) | 0 |
| Quetiapine | 32 (21%) | 0 |
| Clozapine | 45 (30%) | 0 |
| Risperidone | 32 (21%) | 0 |
| Abilify ® | 12 (8%) | 0 |
| Lithium | 7 (5%) | 0 |
| Synthroid | 1 (.7%) | 0 |

*Comparison between groups: p < .001
$^a$GAS-S for lifetime Global Assessment Scale - Severity, at two different period: - the time of first admission or first episode of illness (T1), - the last 6 to 24 months before the ERG recording (T3).
$^b$The IQ was measured on 127 SZ, and 121 controls.

Erg Procedure.

The ERG technique and protocol used in the present studies is as described in Hebert et al. (Hebert, M., et al. *Biol Psychiatry*, 2010. 67(3): p. 270-4), to provide retinal measures of both cones and rods. Recordings were obtained in both eyes (averaged for analysis) with DTL electrodes (Shieldex™ 33/9 Thread, Statex, Bremen, Germany) secured deep in the conjunctival sac. Ground and reference electrodes (Grass gold cup electrodes filled with Grass EC2 electrode cream) are secured to the forehead and external canthi. Photopic ERG was used to assess cone function (responsible for day vision). The subjects were light-adapted for 15 minutes to a light background set at 80 cd/m² provided by a Ganzfeld™ Color dome (Espion, Diagnosys LLC, Littleton, Mass.) in which an integrated camera allows continuous monitoring of the eyes during testing. The Ganzfeld Color dome allows the stimulation of the eye by means of an integrated xenon strobe (white flash) or LEDs (colored flash). A cone luminance-response function (LRF) was provided using 13 increasing white flash intensities ranging from 0.42 to 800 cd·s/m² with an inter-stimulus interval set at 2 seconds (first 9 intensities) and 5 seconds (last 4 intensities). Subjects were then dark-adapted for 30 minutes before the scotopic ERG was performed to assess rod function (night vision). A rod luminance response function was obtained using 12 increasing green flash (wavelength peak: 509 nm) intensities ranging from 0.001 to 1 cd·s/m² with an inter-stimulus interval set at 5 seconds (first 11 intensities) and 10 seconds (last 4 intensities). For all recordings, at least ten responses were averaged for each intensity in order to achieve a good signal to noise ratio. Each recorded waveform (total of 10×13 intensities for the cones and 10×12 intensities for the rods, for each eye) had to be replayed off-line in order to detect any corrupted waveforms (e.g., due to eyeblink) that were then deleted from the averaged waveform before analysis.

Waveform analysis was performed off-line. For each waveform the a-wave (originating from the photoreceptors) and the b-wave (originating from the bipolar cells) was measured. The a-wave was measured from baseline to the trough of the waveform whereas the b-wave was measured from the trough of the a-wave to the peak of the response. Therefore, an anomaly at the level of the a-wave could yield a significant change at the level of the b-wave as well. However, a b-wave reduction can be observed in the absence of an a-wave anomaly. Whereas in the former case, the origin of the deficit could be tied to the photoreceptor functioning (a-wave deficits), in the latter case, a selective b-wave reduction is indicative of an anomaly post synaptic to photoreceptors. Since a luminance response function was produced in the protocol, it was possible to detect the maximal amplitude observed both for the cones and the rods. This response called the Vmax was used for each of the 8 ERG parameters: a-wave, b-wave, amplitudes and implicit times for each system, i.e., cones and rods. More precisely, for the cone function, the Vmax correspond to the maximal response of the photopic hill. The photopic hill is also characterized with fixed intensities such as intensity 7.5 cd·s/m² ("int1" in Tables) and an average of the response at three intensities (13.33, 23.71 and 50 cd·s/m²) referred to as "3-int" in the different tables. For the rod function (scotopic), the Vmax refer to the saturating amplitude observed at the 0.1 cd·s/m² intensity, where rods only are involved in the response (referred to as "Vmax" in Tables). The response at a higher intensity, where both cones and rods are then involved is also recorded (flash intensity of 1 cd·s/m² referred to as "int2" in Tables). Other parameters such as the log K (the intensity necessary to reach the ½ Vmax) and the parameter n which is referring to the slope of the function were also measured. Photopic and scotopic log K and slope were calculated with Origin® 7.0 software (OriginLab Corporation, Northampton, Mass.), following sigmoidal curve fitting.

Neurocognitive Measurements.

The following cognitive domains were assessed in patients and in controls:

1) Intelligence:

A full standard intelligence scale (WISC-III or WAIS-III after 16 years) was completed to assess global intellectual level (Global IQ).

2) Attention:

The major subcomponents of attention were assessed: 2.1 Sustained attention: the Continuous Performance Test-II (CPT-II) Hit reaction time block change and Hit standard error block change variables (Conners, K., Continuous Performance Test II. *Psychological Assessment Resources,* 1999). 2.2 Speed of processing was measured with the Hit reaction time of the CPT-II. 2.3 Selective attention (i.e. the capacity to select target/distractive items) was measured with three variables of the CPT-II: Omissions (number of targets missed), Commissions (number of lures identified as targets), and Detectability (indicator of the capacity to discriminate target from distracters). 2.4 Inhibitory processes (i.e. capacity to suppress the activation of a distracter in order to decrease interference) was measured by the interference score of the Stroop (Golden, C., Stroop Color and Word Test, in Psychological Assessment Resources. 1976: Tampa, Fla., USA).

3) Motor Functions:

The Purdue Pegboard test (Tiffin, J., *Purdue Pegboard Test*, in *Psychological Assessment Resources*. 1948: Tampa, Fla., USA) was administered with the dominant hand, non-dominant hand, and with both hands (bimanual coordination).

4) Memory:

Episodic memory was assessed in visual and auditory modalities. Subjects completed the *Rey Complex Figure Test (RCFT)* (immediate recall and delayed recall) (Meyers, J. E. and Meyers, K. R., *Rey Complex Figure Test and Recognition Trial (RCFT)*, in *Psychological Assessment Resources.* 1995: Odessa, Fla., USA). They were also presented with 24 items, and asked to identify which items were included in the initial figure (recognition) in the *California Verbal Learning Test (CVLT)* (immediate recall and delayed recall) (Delis, D., Kramer, J., Kaplan, E., and Ober, B., *California verbal learning test manual*, in TX: *Psychological Corporation.* 1987: San Antonio, USA). The A1 variable represents their recall on the first trial, and reflects the encoding process of memory. They were also asked to recognize target words between distracters (recognition process). Working memory was assessed with the *Digit span* and with the *Spatial Span* (Weschler memory scale) (Weschler, D., *Wechsler Adult Intelligence Scale—Third edition.* 1997, San Antonio, Tex.: The Psychological Corporation; Weschler, D., *Weschler Memory Scale—Third edition.* 1997, San Antonio, Tex.: The Psychological Corporation; Weschler, D., *Weschler Abbreviated Scale of Intelligence.* 1999, USA: The Psychological Corporation).

5) Executive Functions:

5.1 Planning was assessed with 3 measures of the Tower of London (TOLDX) (Culbertson, W. and Zillmer, E., *Tower of London—TOL DX,* Psychological Assessment Resources: Tampa, Fla.), i.e. "number of problems solved in minimum moves", "rule violation" and "time violation". 5.2 Problem solving was assessed with the classical Wisconsin Card Sorting Test-128 cards (WCST: CV4) (Heaton, R. K., Chelune, G. J., Talley, J. L., Kay, G. G., and Curtiss, G., *Wisconsin card sorting test: manual revised and expanded.* Research edition (WCST-CV:4) 128 cards ed. 1993, Odessa, Fla.: Psychological Assessment Resources) (Total errors, categories completed, learning to learn). 5.3 Initiation/Strategic search was measured with the Verbal Fluency Test (French-Canadian version) (Lussier, F., Normes sur la fluidité verbale en condition phonologique et sémantique, 1996).

Assessment of the Response to Treatment.

A consensual clinical judgement of the response to treatment across life was made blind to ERG by a team made of a research psychiatrist and three experienced research nurses who reviewed the lifetime information about the patient.

These persons personally met to reach a consensus about a global clinical judgement: poor response, intermediate response and good response. The sources of information were the in-patient and out-patient lifetime medical charts, the rating of the PANSS positive and negative scales, the GAS severity and the GAS functionality scales. All the available information was reviewed to assess and rate the functioning at three different periods: —the time of first admission or first episode of illness (T1), —6 to 24 months after the last hospitalization or acute episode (T2)—the last 6 to 24 months with the same medication before the ERG recording (T3). A judgement of compliance to medication based on all sources of information was also taken into account as well as a sufficient dose of antipsychotic. All patients were treated by new generation antipsychotics that were transformed into olanzapine equivalent doses.

Statistical Analysis.

All statistical analyses were performed using the Statistical Analysis Software (SAS) version 9.2. First, univariate analysis were performed by comparing the 150 SZ patients to the 150 controls on each of the eight (8) ERG parameters by means of ANCOVAs (ANalysis of COVAriance) adjusting for age and gender. A corresponding effect size was calculated by subtracting the SZ from the controls average and dividing by a pooled standard deviation derived from the within mean square of the model. Given that eight ERG parameters were analyzed, a threshold of 0.00625 (0.05÷8) was used to detect a significant difference. The same univariate method was used when comparing any other two groups such as BP versus CT, SZ versus BP or Good versus Poor responder.

Second, prediction modeling was performed, based on a multiple stepwise logistic regression (using 0.05 as the significance threshold for the "entry" and "stay" selection in the model), to obtain the subset of ERG parameters that best predicted SZ. Age and gender were imposed in the model. The $R^2$ of the final model provided the proportion of the difference between SZ and controls that can be explained by the selected combination of ERG parameters. The overall assessment of the accuracy of the model was obtained by calculating the area under the Receiver Operating Curve (AU-ROC; Gilbert Saporta, *Probabilités Analyse des Donées et Statistique,* 3ième édition, 2011). The fitted model provides, for each subject, the logit of the probability to belong to one of the two groups in the comparison and a cut-off value of 0.5 on this probability determines the predicted group membership of the subject. A 2×2 table was obtained by crossing the predicted with the true group membership. Estimates of the sensitivity, the specificity (i.e. the proportion of SZ and control subjects, respectively, that were correctly classified) and the odds ratio (OR) can then be calculated from this prediction group membership table. An OR describes the strength of the association between the predicted and the true. Given that an OR value of 1 represents an absence of association (or relatedness) between the predicted and observed group membership, values greater than 1 rather suggest that the predicted group membership is often accurate, i.e. predicting the true group membership. Theoretically, OR takes values ranging from 0 to ∞, the higher values revealing stronger relatedness. This entire procedure of prediction modeling was repeated for the all other comparisons of two groups such as BP vs. CT or Good vs. Poor responders. For the latter comparison, a threshold of 0.10 was rather used.

Example 2: Assessment of ERG Parameters in SZ Patients and Controls

The comparison of SZ patients to controls on each of the eight ERG parameters is depicted in Table 2. As can be seen in the section "Effect size (p-value)" of Table 2, the SZ subjects differ significantly (p<0.0001) from controls on at least five ERG parameters (cone a-wave amplitude, cone b-wave amplitude, cone b-wave implicit time, rod a-wave amplitude and rod b-wave amplitude) with effect sizes ranging from 0.49 to 1.31 (in absolute value). These univariate results show that prediction modeling based on multiple logistic regression may detect a judicious subset of ERG parameters that best predict the group membership, as detailed below.

TABLE 2

Comparison of the 150 SZ patients to 150 controls on ERG parameters

| ERG parameters | Flash intensity[a] | Mean (SD) | | Effect size | P-value |
|---|---|---|---|---|---|
| | | 150 SZ | 150 CT | | |
| Cones | | | | | |
| a-Wave amplitude | int1 | 12.58 (5.2) | 15.60 (4.7) | 0.64 | <0.0001 |
| a-Wave implicit time | 3-int | 14.60 (1.0) | 14.80 (0.9) | 0.21 | 0.064 |
| b-Wave amplitude | Vmax | 83.25 (19.7) | 92.45 (18.0) | 0.51 | <0.0001 |
| b-Wave implicit time | 3-int | 32.92 (1.4) | 31.22 (1.3) | −1.31 | <0.0001 |
| Rods | | | | | |
| a-Wave amplitude | int2 | 58.55 (26.8) | 70.54 (24.5) | 0.49 | <0.0001 |
| a-Wave implicit time | int2 | 24.66 (1.7) | 24.82 (1.6) | 0.10 | 0.394 |
| b-Wave amplitude | int2 | 175.35 (46.8) | 202.84 (42.8) | 0.64 | <0.0001 |
| b-Wave implicit time | int2 | 49.19 (6.4) | 47.75 (5.8) | −0.25 | 0.033 |

Note that age and gender are included in all models as covariate

[a]In the photopic ERG, the peak maximal response correspond to the << Vmax >>, << int1 >> correspond to a fixed intensity of 7.5 cd × s/m$^2$ and << 3-int >> correspond to an average of three intensities. For the rod function (scotopic ERG), << Vmax >> refer to the saturating amplitude observed at the first plateau, where rods only are involved in the response (flash intensity of 0.1 cd × s/m$^2$) and << int2 >> refer to a flash intensity of 1 cd × s/m$^2$.

Table 3A shows that prediction modeling identified a model based on six ERG parameters that best predict if a subject has SZ with an overall accuracy of 0.92, a sensitivity of 0.82 and a specificity of 0.87, corresponding to an OR of 30 as shown in Table 3B. The final model fitted the following equation:

$$Log[P(SZ)/(1-P(SZ)]=-19.03-0.15(gender)-0.04(age)+1.61(phBlat)-0.86(scAlat)-0.02(scBamp)-0.11(phAamp)-0.645(phAlat)+0.10(scBlat)$$

in which, gender=1 if the subject is a female and 0 if the subject is a male;

phBlat=cone b-Wave implicit time, average of three intensities (13.33, 23.71 and 50 cd×s/m²; 3-int);

scAlat=rod a-Wave implicit time, flash intensity of 1 cd×s/m² (int2);

scBamp=rod b-Wave amplitude, flash intensity of 1 cd×s/m² (int2);

phAamp=cone a-Wave amplitude, fixed intensity of 7.5 cd×s/m² (int1);

phAlat=cone a-Wave implicit time, average of three intensities (3-int);

scBlat=rod b-Wave implicit time, flash intensity of 1 cd×s/m² (int2).

Table 3A also shows that other models including fewer ERG parameters (strictly 1, or exactly 2 or 3 or 4 or 5) can also predict SZ, but typically with a lower accuracy, sensitivity and/or specificity relative to the model based on six ERG parameters.

TABLE 3A

Parameter estimates of the multiple logistic regression to predict the group

Figure 2A:
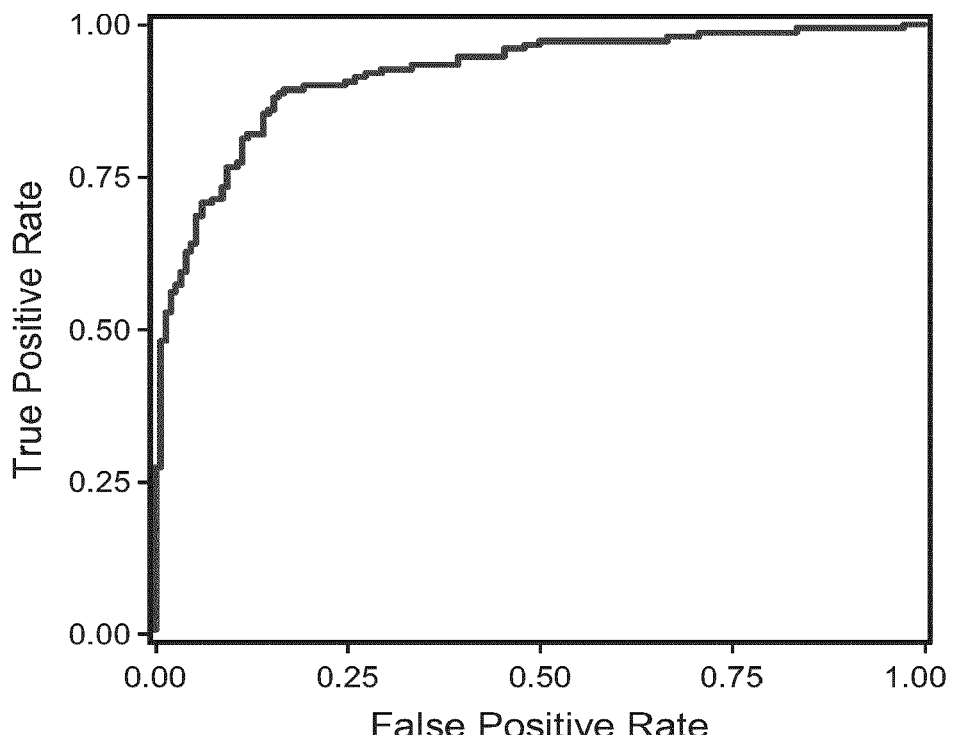
FIG. 2A shows the characteristics of the model predicting schizophrenia (SZ) based on 6 electroretinography (ERG) parameters (see Table 3A): A logistic stepwise regression analysis was performed entering all ERG parameters. Taken together, 6 ERG markers predicted disease with an accuracy of 92% (area under curve [AUC] from a receiving operating characteristic [ROC] analysis) corresponding to a sensitivity of 82% and a specificity of 87%.

| Parameter(flash intensity[a]) | Parameter estimate Value | 95% CI | $R^2$ | AUC | Sensitivity | Specificity |
|---|---|---|---|---|---|---|
| SZ Vs CT | | | | | | |
| Best model of the multiple logistic regression (model 1) | | | 0.48 | 0.92 (FIG. 2A) | 82% | 87% |
| Intercept | −19.03 | [−30.7; −8.2] | | | | |
| Age | −0.04 | [−0.08; 0] | | | | |
| Gender[b] | −0.15 | [−0.50; 0.23] | | | | |
| cone b-Wave implicit time (3-int) | 1.61 | [1.23; 2.05] | | | | |
| rod a-Wave implicit time (int2) | −0.86 | [−1.26; −0.49] | | | | |
| rod b-Wave amplitude (int2) | −0.02 | [−0.03; −0.01] | | | | |
| cone a-Wave amplitude (int1) | −0.11 | [−0.20; −0.03] | | | | |
| cone a-Wave implicit time (3-int) | −0.65 | [−1.13; −0.18] | | | | |
| rod b-Wave implicit time (int2) | 0.10 | [0.02; 0.19] | | | | |
| Models of the simple logistic regression | | | | | | |
| Model 2a | | | | | | |
| Intercept | 2.56 | [1.19; 4.0] | 0.13 | 0.70 | 67% | 59% |
| Age | −0.02 | [−0.04; 0.01] | | | | |
| Gender[b] | −0.35 | [−0.62; 0.07] | | | | |
| cone a-Wave amplitude (int1) | −0.14 | [−0.2; −0.08] | | | | |
| Model 2b | | | | | | |
| Intercept | 2.80 | [0.45; 5.25] | 0.06 | 0.66 | 69% | 51% |
| Age | −0.01 | [−0.03; 0.02] | | | | |
| Gender[b] | −0.51 | [−0.78; −0.25] | | | | |
| cone a-Wave implicit time (int1) | −0.17 | [−0.33; −0.02] | | | | |
| Model 2c | | | | | | |
| Intercept | 3.26 | [1.63; 4.97] | 0.11 | 0.68 | 63% | 63% |
| Age | −0.02 | [−0.05; 0] | | | | |
| Gender[b] | −0.31 | [0.03; 0.59] | | | | |
| cone b-Wave amplitude (3-int) | −0.03 | [−0.05; −0.02] | | | | |
| Model 2d | | | | | | |
| Intercept | −39.25 | [−49.3; −30.3] | 0.36 | 0.85 | 75% | 83% |
| Age | −0.06 | [−0.1; −0.03] | | | | |
| Gender[b] | −0.23 | [−0.55; 0.08] | | | | |
| cone b-Wave implicit time (3-int) | 1.30 | [1.01; 1.63] | | | | |
| Model 2e | | | | | | |
| Intercept | 2.07 | [0.75; 3.44] | 0.10 | 0.67 | 66% | 57% |
| Age | −0.02 | [−0.05; 0] | | | | |
| Gender[b] | −0.38 | [−0.65; −0.11] | | | | |
| rod a-Wave amplitude (int2) | −0.02 | [−0.03; −0.01] | | | | |
| Model 2f | | | | | | |
| Intercept | 2.18 | [0.07; 4.37] | 0.06 | 0.64 | 67% | 47% |
| Age | −0.01 | [−0.03; 0.01] | | | | |
| Gender[b] | −0.48 | [−0.75; −0.22] | | | | |
| rod a-Wave implicit time (Vmax) | −0.06 | [−0.13; 0] | | | | |
| Model 2g | | | | | | |
| Intercept | 3.43 | [1.88; 5.06] | 0.14 | 0.71 | 65% | 60% |
| Age | −0.02 | [−0.04; 0.01] | | | | |
| Gender[b] | −0.26 | [−0.55; 0.02] | | | | |
| rod b-Wave amplitude (int2) | −0.02 | [−0.02; −0.01] | | | | |
| Model 2h | | | | | | |
| Intercept | −2.22 | [−4.69; −0.01] | 0.07 | 0.66 | 69% | 53% |
| Age | −0.02 | [−0.05; 0] | | | | |
| Gender[b] | −0.41 | [−0.68; −0.15] | | | | |

TABLE 3A-continued

Parameter estimates of the multiple logistic regression to predict the group

| Parameter(flash intensity[a]) | Parameter estimate Value | 95% CI | $R^2$ | AUC | Sensitivity | Specificity |
|---|---|---|---|---|---|---|
| rod b-Wave implicit time (int2) | 0.06 | [0.01; 0.11] | | | | |
| Model based on 2 ERG parameters[c] | | | | | | |
| Model 3 | | | | | | |
| Intercept | −34.63 | [−45.0; −25.3] | 0.39 | .87 | 77% | 84% |
| Age | −0.05 | [−0.08; −0.02] | | | | |
| Gender[b] | −0.31 | [−0.65; 0.01] | | | | |
| cone b-Wave implicit time (3-int) | 1.49 | [1.16; 1.86] | | | | |
| rod a-Wave implicit time (int2) | −0.45 | [−0.68; −0.23] | | | | |
| Model based on 3 ERG parameters[c] | | | | | | |
| Model 4 | | | | | | |
| Intercept | −25.51 | [−36.6; −15.2] | 0.44 | .90 | 81% | 85% |
| Age | −0.04 | [−0.07; 0] | | | | |
| Gender[b] | −0.09 | [−0.45; 0.26] | | | | |
| cone b-Wave implicit time (3-int) | 1.53 | [1.18; 1.93] | | | | |
| rod a-Wave implicit time (int2) | −0.72 | [−1.02; −0.45] | | | | |
| rod b-Wave amplitude (int2) | −0.02 | [−0.03; −0.01] | | | | |
| Model based on 4 ERG parameters[c] | | | | | | |
| Model 5 | | | | | | |
| Intercept | −24.92 | [−36.3; −14.4] | 0.46 | .91 | 79% | 88% |
| Age | −0.04 | [−0.08; −0.01] | | | | |
| Gender[b] | −0.07 | [−0.44; 0.29] | | | | |
| cone b-Wave implicit time (3-int) | 1.55 | [1.19; 1.97] | | | | |
| rod a-Wave implicit time (int2) | −0.74 | [−1.04; −0.46] | | | | |
| rod b-Wave amplitude (int2) | −0.02 | [−0.03; −0.01] | | | | |
| cone a-Wave amplitude (int1) | −0.11 | [−0.19; −0.03] | | | | |
| Model based on 5 ERG parameters[c] | | | | | | |
| Model 6 | | | | | | |
| Intercept | −21.65 | [−33.2; −10.9] | 0.47 | .91 | 79% | 87% |
| Age | −0.04 | [−0.08; 0] | | | | |
| Gender[b] | −0.17 | [−0.55; 0.21] | | | | |
| cone b-Wave implicit time (3-int) | 1.62 | [1.24; 2.06] | | | | |
| rod a-Wave implicit time (int2) | −0.62 | [−0.94; −0.33] | | | | |
| rod b-Wave amplitude (int2) | −0.02 | [−0.03; −0.01] | | | | |
| cone a-Wave amplitude (int1) | −0.12 | [−0.20; −0.04] | | | | |
| cone a-Wave implicit time (3-int) | −0.58 | [−1.06; −0.13] | | | | |

[a] Note that age and gender are included in models as covariate
[b] In the photopic ERG, the peak maximal response correspond to the << Vmax >>, << int1 >> correspond to a fixed intensity of 7.5 cd × s/m² and << 3-int >> correspond to an average of three intensities. For the rod function (scotopic ERG), << Vmax >> refer to the saturating amplitude observed at the first plateau, where rods only are involved in the response (flash intensity of 0.1 cd × s/m²) and << int2 >> refer to a flash intensity of 1 cd × s/m².
[c] When more than one model based on the same number of ERG parameters was possible, only the model that provided the higher accuracy according to the AUC is presented.

TABLE 3B

Prediction of SZ cases vs. controls

| As predicted by the ERGs | Group sample SZ | CT | |
|---|---|---|---|
| SZ | 123 (82%) | 20 (13%) | |
| CT | 27 (18%) | 130 (87%) | |
| Total | 150 | 150 | OR = 30 |

TABLE 3C

Prediction of SZ cases vs. controls using cut-off values of 0.80 and 0.20 for classifying SZ and CT respectively

| Sample | Percentage of uncertain subjects[a] | Sensitivity | Specificity | OR |
|---|---|---|---|---|
| Total sample | 37% | 92% (91/99) | 93% (84/90) | 159 |
| Split-Half Procedure | | | | |
| Train data | 35% | 92% (47/51) | 96% (44/46) | 259 |
| Test data | 35% | 90% (44/49) | 92% (45/49) | 99 |

[a] Subjects with a probability of being SZ in between the cut-off values, i.e. between 0.2 and 0.8.

Table 3C shows that when using a more stringent cut-off value for predicting a subject in the SZ group, the sensitivity and specificity as well as OR were greatly improved (Table 3C). Indeed, with the cut-off probability values of 0.80 and 0.20 for classifying a subject as SZ or CT respectively, the sensitivity and specificity were found well above 0.90 and the OR reached 99 in the test sample and easily exceeded 100 in the train and total samples.

Example 3: ERG Profile and Response to Psychotropic Treatment

The response to antipsychotic treatment in patients of the different ERG strata is depicted in Table 4. The Chi-square test for this 2×2 table revealed a significant p-value (p=0.0015) indicating that the strata are related to the response to psychotropic treatment. Indeed, stratum 1 contains SZ subjects having a very high probability (0.76) of being good responders, while strata 2 or 3 predict rather low chance (0.31 or 0.35) to respond well.

TABLE 4

Response to antipsychotic treatment depends on ERG strata

| ERG Stratum | Good response | Poor-intermediate response | Total |
|---|---|---|---|
| 1 | 76% (22) | 24% (7) | 29 |
| 2 | 31% (8) | 69% (18) | 26 |
| 3 | 38% (20) | 62% (33) | 53 |
| 4 | 58% (14) | 42% (10) | 24 |

$X^2_3 = 15.4$, $p = .0015$

In univariate analysis, when, on each ERG parameter, the good responders to any medication (antipsychotic treatment) were compared to the poor-intermediate responders, significant differences were observed on two ERG parameters (cone a-wave amplitude, with an effect size of 0.5, p=0.005; and a rod a-wave implicit time, with an effect size of −0.52, p=0.003; see Table 5A).

TABLE 5A

Comparison of the Good vs. Poor-intermediate responders to any medication on eight ERG parameters

| ERG parameters[a] | Flash intensity[a] | Mean (SD) | | Effect size | P-value |
|---|---|---|---|---|---|
| | | Good responders (N = 64) | Poor-intermediate responders (N = 68) | | |
| Cones | | | | | |
| a-Wave amplitude | int1 | 13.75 (4.8) | 11.61 (4.9) | 0.50 | 0.0045 |
| a-Wave implicit time | 3-int | 14.51 (1.0) | 14.74 (1.0) | −0.27 | 0.1231 |
| b-Wave amplitude | int1 | 68.05 (20.7) | 61.07 (21.3) | 0.38 | 0.0324 |
| b-Wave implicit time | int1 | 29.19 (1.9) | 29.85 (1.9) | −0.39 | 0.0254 |
| Rods | | | | | |
| a-Wave amplitude | int2 | 62.20 (25.5) | 51.61 (26.2) | 0.46 | 0.0086 |
| a-Wave implicit time | int2 | 24.21 (1.8) | 25.07 (1.9) | −0.52 | 0.0033 |
| b-Wave amplitude | int2 | 180.31 (45.6) | 168.32 (46.9) | 0.29 | 0.0938 |
| b-Wave implicit time | int2 | 47.78 (7.9) | 51.09 (8.1) | −0.47 | 0.0078 |

Note that age and gender are included in all models as covariate

[a]In the photopic ERG, the peak maximal response correspond to the << Vmax >>, << int1 >> correspond to a fixed intensity of 7.5 cd × s/m² and << 3-int >> correspond to an average of three intensities. For the rod function (scotopic ERG), << Vmax >> refer to the saturating amplitude observed at the first plateau, where rods only are involved in the response (flash intensity of 0.1 cd × s/m²) and << int2 >> refer to a flash intensity of 1 cd × s/m².

When comparing the good and poor-intermediate SZ responders to olanzapine (univariate analysis), two ERG parameters showed differences with p-values below 0.05 (cone a-wave amplitude, ES=0.95, p=0.03; rod a-wave implicit time, ES=−1.01, p=0.022; see Table 5B). The comparison of the good with the poor-intermediate SZ responders to quetiapine on each of the eight ERG parameters allow the identification of one ERG parameter with a p-value below 0.05 (cone b-wave amplitude, ES=1.17, p-value=0.019; see Table 5C). For the SZ subjects taking aripiprazole (Abilify®), the stronger difference between the good and the poor-intermediate responders in univariate analysis was observed for the rod a-wave amplitude (ES=−0.96, p-value=0.18; see Table 5D). These univariate results show that prediction modeling based on multiple logistic regression may detect a subset of ERG parameters that best predict the group membership, as detailed below.

TABLE 5B

Comparison of the good responders vs. the poor-intermediate responders to olanzapine on ERG parameters.

| ERG parameters[a] | Flash intensity[b] | Mean (SD) | | Effect size | P-value |
|---|---|---|---|---|---|
| | | Good responders (N = 15) | Poor-intermediate responders (N = 10) | | |
| Cones | | | | | |
| a-Wave amplitude | int1 | 15.54 (6.0) | 10.06 (6.0) | 0.95 | 0.0303 |
| a-Wave implicit time | int1 | 15.27 (1.8) | 16.46 (1.9) | −0.66 | 0.1186 |
| b-Wave amplitude | 3-int | 83.00 (18.6) | 68.47 (18.7) | 0.81 | 0.0617 |
| b-Wave implicit time | int1 | 29.22 (1.9) | 30.11 (1.9) | −0.48 | 0.2506 |
| Rods | | | | | |
| a-Wave amplitude | Vmax | 24.04 (10.7) | 18.96 (10.7) | 0.49 | 0.2421 |
| a-Wave implicit time | int2 | 23.27 (1.7) | 24.98 (1.8) | −1.01 | 0.0225 |
| b-Wave amplitude | int2 | 187.55 (42.4) | 166.12 (42.5) | 0.52 | 0.2147 |
| b-Wave implicit time | int2 | 47.04 (9.5) | 52.56 (9.5) | −0.60 | 0.1556 |

[a]Note that age and gender are included in all models as covariate

[b]In the photopic ERG, the peak maximal response correspond to the << Vmax >>, << int1 >> correspond to a fixed intensity of 7.5 cd × s/m² and << 3-int >> correspond to an average of three intensities. For the rod function (scotopic ERG), << Vmax >> refer to the saturating amplitude observed at the first plateau, where rods only are involved in the response (flash intensity of 0.1 cd × s/m²) and << int2 >> refer to a flash intensity of 1 cd × s/m².

TABLE 5C

Comparison of the good responders vs. the poor-intermediate responders to quetiapine on ERG parameters

| | | Mean (SD) | | | |
|---|---|---|---|---|---|
| ERG parameters[a] | Flash intensity[b] | Good responders (N = 15) | Poor-intermediate responders (N = 7) | Effect size | P-value |
| Cones | | | | | |
| a-Wave amplitude | int1 | 12.24 (4.3) | 8.96 (4.1) | 0.83 | 0.0868 |
| a-Wave implicit time | 3-int | 14.50 (1.2) | 15.21 (1.1) | −0.68 | 0.1551 |
| b-Wave amplitude | int1 | 67.63 (14.9) | 51.69 (14.2) | 1.17 | 0.0194 |
| b-Wave implicit time | 3-int | 32.75 (1.2) | 33.39 (1.1) | −0.60 | 0.2070 |
| Rods | | | | | |
| a-Wave amplitude | Vmax | 18.32 (6.4) | 23.59 (6.1) | −0.90 | 0.0651 |
| a-Wave implicit time | int2 | 24.25 (1.2) | 24.56 (1.2) | −0.28 | 0.5433 |
| b-Wave amplitude | Vmax | 146.93 (31.2) | 138.01 (29.8) | 0.31 | 0.5017 |
| b-Wave implicit time | int2 | 47.96 (5.4) | 51.68 (5.2) | −0.75 | 0.1172 |

[a]Note that age and gender are included in all models as covariate
[b]In the photopic ERG, the peak maximal response correspond to the « Vmax », « int1 » correspond to a fixed intensity of 7.5 cd × s/m$^2$ and « 3-int » correspond to an average of three intensities. For the rod function (scotopic ERG), « Vmax » refer to the saturating amplitude observed at the first plateau, where rods only are involved in the response (flash intensity of 0.1 cd × s/m$^2$) and « int2 » refer to a flash intensity of 1 cd × s/m$^2$.

TABLE 5D

Comparison of the good responders Vs the poor-intermediate responders to aripiprazole (Abilify ®) on ERG parameters

| | | Mean (SD) | | | |
|---|---|---|---|---|---|
| ERG parameters[a] | Flash intensity[b] | Good responders (N = 5) | Poor-intermediate responders (N = 5) | Effect size | P-value |
| Cones | | | | | |
| a-Wave amplitude | Vmax | 18.69 (4.5) | 21.10 (4.5) | −0.54 | 0.4289 |
| a-Wave implicit time | int1 | 14.88 (1.5) | 15.68 (1.5) | −0.52 | 0.4400 |
| b-Wave amplitude | 3-int | 86.36 (23.5) | 70.55 (23.6) | 0.67 | 0.3282 |
| b-Wave implicit time | int1 | 29.39 (0.9) | 29.77 (0.9) | −0.42 | 0.5348 |
| Rods | | | | | |
| a-Wave amplitude | Vmax | 12.53 (7.6) | 19.81 (7.6) | −0.96 | 0.1804 |
| a-Wave implicit time | int2 | 25.84 (2.3) | 23.87 (2.3) | 0.86 | 0.2207 |
| b-Wave amplitude | int2 | 172.79 (52.8) | 158.24 (53.1) | 0.28 | 0.6781 |
| b-Wave implicit time | Vmax | 77.01 (14.5) | 68.32 (14.6) | 0.60 | 0.3809 |

[a]Note that age and gender are included in all models as covariate
[b]In the photopic ERG, the peak maximal response correspond to the « Vmax », « int1 » correspond to a fixed intensity of 7.5 cd × s/m$^2$ and « 3-int » correspond to an average of three intensities. For the rod function (scotopic ERG), « Vmax » refer to the saturating amplitude observed at the first plateau, where rods only are involved in the response (flash intensity of 0.1 cd × s/m$^2$) and « int2 » refer to a flash intensity of 1 cd × s/m$^2$.

Prediction modeling of the response to any treatment in the total sample of 150 SZ patients was performed, and two ERG parameters were identified, namely the rod a-wave implicit time and the cone a-wave amplitude, that, together, best predicted if a SZ subject is a good responder to any treatment, with an overall accuracy of 0.70 (see Table 6A) and an a corresponding odds ratio (OR) of 3.7 (see Table 6B). More importantly, when conducting prediction modeling in subsamples composed of patients taking particular antipsychotic molecules without clozapine (i.e. olanzapine, n=25 patients; quetiapine, n=22 patients; and aripiprazole (Abilify®), n=12), it was observed that these three medications may display a specific ERG signature marking better and poorer responders. Indeed, a model based on three ERG parameters (Table 6A) was capable of perfectly predicting the true classification of good versus poor-intermediate responders to olanzapine, yielding an OR of ∞ (Table 6C). Also, for quetiapine, a model based on two ERG parameters (Table 6A) was capable of predicting good versus poor-intermediate responders with a high accuracy (AUC=0.96) corresponding to an OR of 39 (Table 6D). Moreover, based on 10 SZ subjects taking aripiprazole (Abilify®), one ERG parameter (Table 6A) capable of predicting good versus poor-intermediate responders with an accuracy of 0.84 was detected, corresponding to an OR of 6 (Table 6E). Other models including fewer ERG parameters (strictly 1, or exactly 2) that can possibly predict SZ good responders, but with lesser accuracy, are also reported in Table 6A.

TABLE 6A

Parameter estimates of the multiple logistic regression to predict the good responders to treatment

Figure 3A:
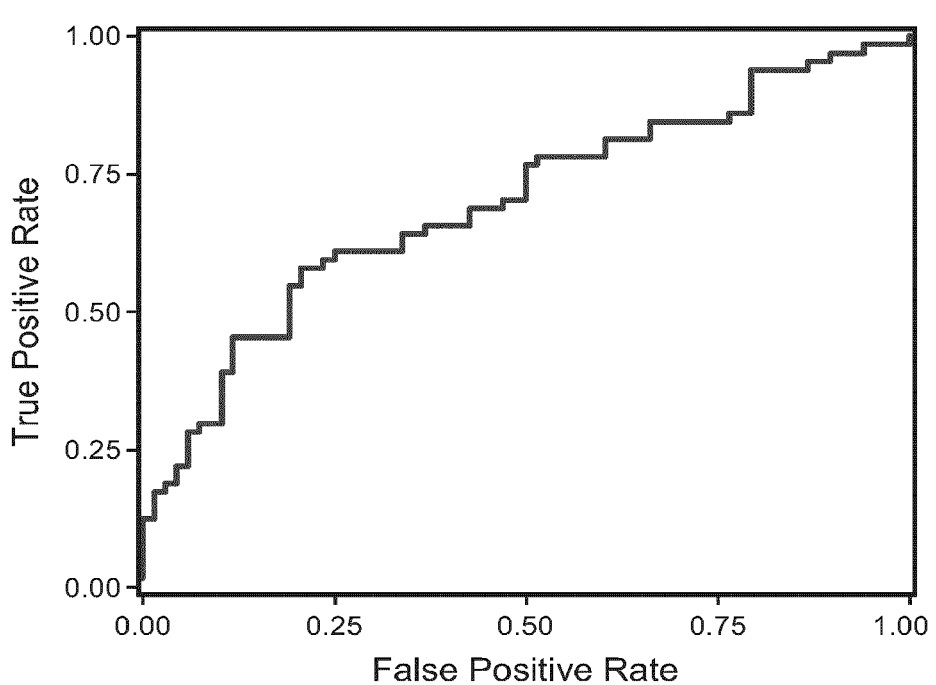
FIG. 3A is the ROC curve of the model predicting, for SZ subjects, good relative to poor-intermediate responders to any medication, based on 2 ERG parameters (see Table 6A), with an AUC of 70% corresponding to a sensitivity of 61% and a specificity of 71%.
Figure 3B:
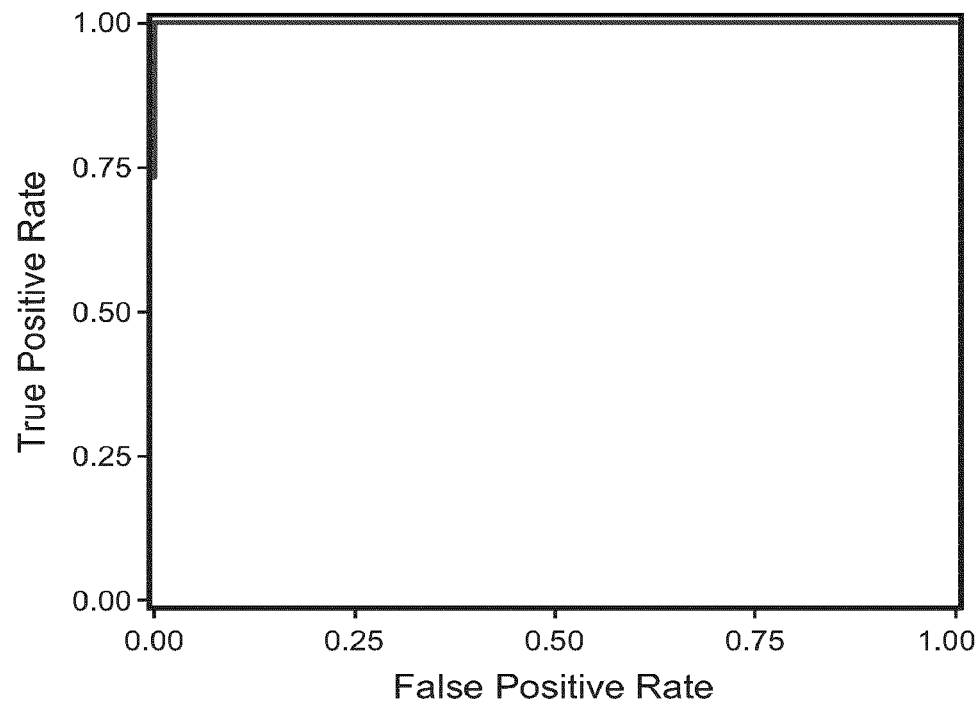
FIG. 3B is the ROC curve of the model predicting good relative to poor-intermediate responders SZ subjects taking olanzapine (without clozapine), based on 3 ERG parameters (see Table 6A), with an AUC of 100% corresponding to a sensitivity and a specificity of 100%.

| Good vs. Poor intermediate response | Parameter estimate | | | | | |
|---|---|---|---|---|---|---|
| Parameter(flash intensity[a]) | Value | 95% CI | $R^2$ | AUC | Sensitivity | Specificity |
| SZ sample taking any medication | | | | | | |
| Best model of the multiple logistic regression (model 1) | | | 0.11 | 0.70 (FIG. 3A) | 61% | 71% |
| intercept | 4.08 | [−1.93; 10.63] | | | | |
| age | 0.04 | [0; 0.09] | | | | |
| gender[b] | −0.03 | [−0.49; 0.44] | | | | |
| rod a-Wave implicit time (int2) | −0.29 | [−0.56; −0.05] | | | | |
| cone a-Wave amplitude (int1) | 0.10 | [0.01; 0.20] | | | | |
| Models of the simple logistic regression | | | | | | |
| Model 2a | | | | | | |
| intercept | −2.75 | [−5.02; −0.64] | 0.07 | 0.65 | 64% | 47% |
| age | 0.03 | [−0.01; 0.07] | | | | |
| gender[b] | 0.06 | [−0.39; 0.51] | | | | |
| cone a-Wave amplitude (int1) | 0.13 | [0.04; 0.23] | | | | |
| Model 2b | | | | | | |
| intercept | 3.31 | [−2.19; 9.17] | 0.03 | 0.62 | 68% | 42% |
| age | 0.03 | [−0.01; 0.08] | | | | |
| gender[b] | 0.04 | [−0.4; 0.49] | | | | |
| cone a-Wave implicit time (3-int) | −0.32 | [−0.75; 0.08] | | | | |
| Model 2c | | | | | | |
| intercept | −2.91 | [−5.52; −0.45] | 0.05 | 0.62 | 65% | 45% |
| age | 0.04 | [0; 0.08] | | | | |
| gender[b] | 0.01 | [−0.44; 0.46] | | | | |
| cone b-Wave amplitude (int1) | 0.02 | [0; 0.04] | | | | |
| Model 2d | | | | | | |
| intercept | 5.02 | [−0.06; 10.51] | 0.06 | 0.63 | 59% | 38% |
| age | 0.04 | [0; 0.09] | | | | |
| gender[b] | 0.03 | [−0.42; 0.48] | | | | |
| cone b-Wave implicit time (Vmax) | −0.21 | [−0.4; −0.04] | | | | |
| Model 2e | | | | | | |
| intercept | −2.60 | [−4.89; −0.5] | 0.06 | 0.65 | 71% | 44% |
| age | 0.03 | [−0.01; 0.08] | | | | |
| gender[b] | 0.08 | [−0.38; 0.53] | | | | |
| rod a-Wave amplitude (int2) | 0.02 | [0.01; 0.04] | | | | |
| Model 2f | | | | | | |
| intercept | 6.89 | [1.45; 13.01] | 0.08 | 0.68 | 59% | 36% |
| age | 0.04 | [0; 0.09] | | | | |
| gender[b] | −0.01 | [−0.47; 0.45] | | | | |
| rod a-Wave implicit time (int2) | −0.35 | [−0.61; −0.12] | | | | |
| Model 2g | | | | | | |
| intercept | −2.41 | [−4.92; −0.02] | 0.03 | 0.61 | 60% | 50% |
| age | 0.03 | [−0.01; 0.07] | | | | |
| gender[b] | 0.00 | [−0.45; 0.46] | | | | |
| rod b-Wave amplitude (int2) | −0.01 | [0; 0.02] | | | | |
| Model 2h | | | | | | |
| intercept | 2.85 | [−0.38; 6.71] | 0.07 | 0.68 | 65% | 38% |
| age | 0.03 | [−0.01; 0.07] | | | | |
| gender[b] | 0.02 | [−0.42; 0.47] | | | | |
| rod b-Wave implicit time (int2) | −0.09 | [−0.16; −0.02] | | | | |
| SZ taking olanzapine without clozapine | | | | | | |
| Best model of the multiple logistic regression (model3) | | | 0.72 | 1 (FIG. 3B) | 100% | 100% |
| intercept | 754.71 | [−277; 1787] | | | | |
| age | −7.80 | [−18.6; 3.00] | | | | |
| gender[b] | −42.44 | [−101.2; 16.3] | | | | |
| rod a-Wave implicit time (int2) | −36.68 | [−87.2; 13.85] | | | | |
| cone a-Wave amplitude (3-int) | 10.44 | [−4.28; 25.15] | | | | |
| rod a-Wave implicit time (Vmax) | 9.51 | [−4.07; 23.10] | | | | |
| Models of the simple logistic regression | | | | | | |
| Model 4a | | | | | | |
| intercept | 9.63 | [−4.15; 28.45] | 0.39 | 0.87 | 80% | 80% |
| age | −0.31 | [−0.8; −0.02] | | | | |
| gender[b] | −0.86 | [−2.94; 0.64] | | | | |
| cone a-Wave amplitude (int1) | 0.41 | [0.08; 0.97] | | | | |

TABLE 6A-continued

Parameter estimates of the multiple logistic regression to predict the good responders to treatment

Figure 3C:
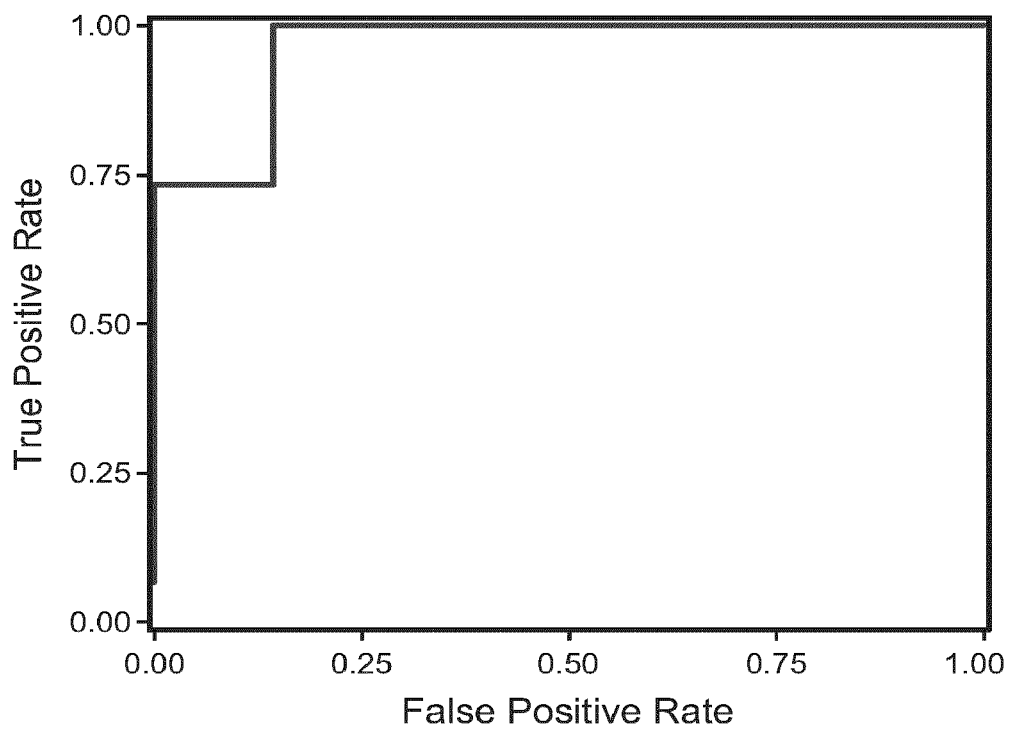
FIG. 3C is the ROC curve of the model predicting good relative to poor-intermediate responders SZ subjects taking quetiapine (without clozapine), based on 2 ERG parameters (see Table 6A), with an AUC of 96% corresponding to a sensitivity of 87% and a specificity of 86%.

| Good vs. Poor intermediate response | Parameter estimate | | $R^2$ | AUC | Sensitivity | Specificity |
|---|---|---|---|---|---|---|
| Parameter(flash intensity[a]) | Value | 95% CI | | | | |
| Model 4b | | | | | | |
| intercept | 15.87 | [3.97; 33.28] | 0.26 | 0.79 | 87% | 60% |
| age | −0.19 | [−0.51; 0] | | | | |
| gender[b] | 0.11 | [−1.08; 1.3] | | | | |
| cone a-Wave implicit time (int1) | −0.42 | [−1.1; 0.14] | | | | |
| Model 4c | | | | | | |
| intercept | 6.64 | [−4.42; 21.51] | 0.32 | 0.84 | 67% | 70% |
| age | −0.25 | [−0.58; −0.03] | | | | |
| gender[b] | −0.25 | [−1.51; 0.96] | | | | |
| cone b-Wave amplitude (Vmax) | 0.06 | [0; 0.14] | | | | |
| Model 4d | | | | | | |
| intercept | 18.44 | [1.65; 41.16] | 0.23 | 0.77 | 73% | 60% |
| age | −0.19 | [−0.51; 0.01] | | | | |
| gender[b] | −0.26 | [−1.62; 0.97] | | | | |
| cone b-Wave implicit time (int1) | −0.31 | [−0.97; 0.23] | | | | |
| Model 4e | | | | | | |
| intercept | 7.92 | [−2.19; 22.78] | 0.24 | 0.81 | 73% | 60% |
| age | −0.19 | [−0.51; 0.01] | | | | |
| gender[b] | 0.12 | [−1.16; 1.43] | | | | |
| rod a-Wave amplitude (Vmax) | 0.06 | [−0.04; 0.19] | | | | |
| Model 4f | | | | | | |
| intercept | 45.87 | [14.98; 103.7] | 0.42 | 0.88 | 93% | 70% |
| age | −0.16 | [−0.52; 0.08] | | | | |
| gender[b] | −0.85 | [−2.54; 0.51] | | | | |
| rod a-Wave implicit time (int2) | −1.57 | [−3.68; −0.36] | | | | |
| Model 4g | | | | | | |
| intercept | 9.00 | [−1.43; 23.52] | 0.26 | 0.80 | 80% | 70% |
| age | −0.27 | [−0.62; −0.04] | | | | |
| gender[b] | −0.13 | [−1.32; 1.03] | | | | |
| rod b-Wave amplitude (int2) | 0.02 | [−0.01; 0.06] | | | | |
| Model 4h | | | | | | |
| intercept | 20.89 | [5.27; 44.34] | 0.31 | 0.85 | 87% | 80% |
| age | −0.15 | [−0.47; 0.07] | | | | |
| gender[b] | −0.41 | [−1.79; 0.82] | | | | |
| rod b-Wave implicit time (int2) | −0.28 | [−0.71; 0] | | | | |
| Model based on 2 ERG parameters[c] | | | | | | |
| Model 5 | | | | | | |
| intercept | 54.02 | [8.69; 147.4] | 0.58 | 0.97 | 80% | 93% |
| age | −0.46 | [−1.31; 0.03] | | | | |
| gender[b] | −1.91 | [−5.39; 0.05] | | | | |
| rod a-Wave implicit time (int2) | −2.09 | [−5.68; −0.41] | | | | |
| cone a-Wave amplitude (3-int) | 0.90 | [0.18; 2.7] | | | | |
| SZ taking quetiapine without clozapine | | | | | | |
| Best model of the multiple logistic regression (model 6) | | | 0.53 | 0.96 (FIG. 3C) | 87% | 86% |
| intercept | 2.28 | [−30.2; 38.9] | | | | |
| age | −0.19 | [−1.17; 0.36] | | | | |
| gender[b] | −0.50 | [−5.11; 3.01] | | | | |
| cone b-Wave amplitude (int1) | 0.34 | [0.09; 0.97] | | | | |
| rod a-Wave amplitude (Vmax) | −0.61 | [−1.81; −0.13] | | | | |
| Models of the simple logistic regression | | | | | | |
| Model 7a | | | | | | |
| intercept | −1.40 | [−7.19; 3.87] | 0.15 | 0.75 | 93% | 29% |
| age | −0.01 | [−0.12; 0.11] | | | | |
| gender[b] | 0.24 | [−0.95; 1.59] | | | | |
| cone a-Wave amplitude (int1) | 0.23 | [−0.01; 0.53] | | | | |
| Model 7b | | | | | | |
| intercept | 47.62 | [15.63; 98.65] | 0.41 | 0.87 | 93% | 71% |
| age | 0.02 | [−0.12; 0.19] | | | | |
| gender[b] | −0.29 | [−2.24; 1.7] | | | | |
| cone a-Wave implicit time (Vmax) | −3.13 | [−6.50; −1.02] | | | | |

TABLE 6A-continued

Parameter estimates of the multiple logistic regression to predict the good responders to treatment

Figure 3D:
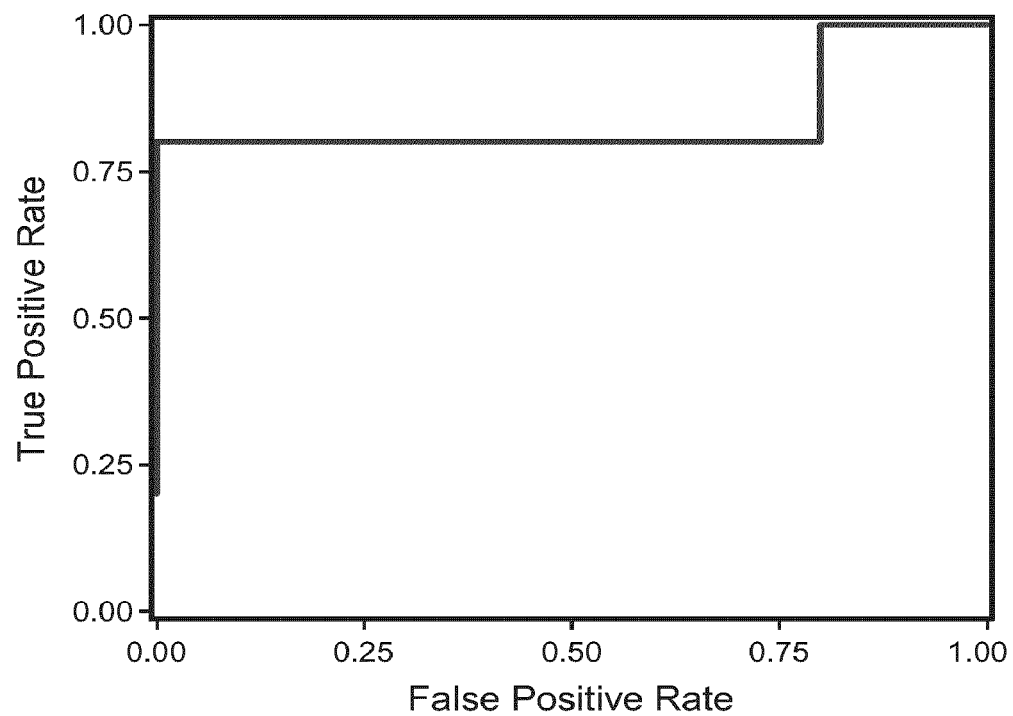
FIG. 3D is the ROC curve of the model predicting good relative to poor-intermediate responders SZ subjects taking aripiprazole (Abilify®) (without clozapine), based on one ERG parameter (see Table 6A), with an AUC of 84% corresponding to a sensitivity of 80% and a specificity of 60%.

| Good vs. Poor intermediate response | Parameter estimate | | | | | |
|---|---|---|---|---|---|---|
| Parameter(flash intensity[a]) | Value | 95% CI | $R^2$ | AUC | Sensitivity | Specificity |
| Model 7c | | | | | | |
| intercept | −12.76 | [−32.11; −1.08] | 0.30 | 0.82 | 80% | 43% |
| age | 0.15 | [−0.02; 0.43] | | | | |
| gender[b] | −0.69 | [−2.79; 0.83] | | | | |
| cone b-Wave amplitude (int1) | 0.13 | [0.03; 0.30] | | | | |
| Model 7d | | | | | | |
| intercept | 23.88 | [−6.55; 63.95] | 0.09 | 0.74 | 100% | 43% |
| age | 0.02 | [−0.09; 0.15] | | | | |
| gender[b] | 0.15 | [−0.97; 1.39] | | | | |
| cone b-Wave implicit time (3-int) | −0.73 | [−1.99; 0.24] | | | | |
| Model 7e | | | | | | |
| intercept | 9.98 | [0.52; 23.87] | 0.19 | 0.73 | 80% | 43% |
| age | −0.13 | [−0.35; 0.03] | | | | |
| gender[b] | 0.02 | [−1.28; 1.37] | | | | |
| rod a-Wave amplitude (Vmax) | −0.20 | [−0.45; −0.01] | | | | |
| Model 7f | | | | | | |
| intercept | 8.90 | [−13.6; 33.8] | 0.02 | 0.61 | 100% | 0% |
| age | −0.01 | [−0.12; 0.09] | | | | |
| gender[b] | 0.19 | [−1.02; 1.49] | | | | |
| rod a-Wave implicit time (int2) | −0.31 | [−1.29; 0.59] | | | | |
| Model 7g | | | | | | |
| intercept | −1.01 | [−8.63; 6.38] | 0.03 | 0.62 | 100% | 0% |
| age | 0.00 | [−0.11; 0.10] | | | | |
| gender[b] | −0.09 | [−1.21; 1.10] | | | | |
| rod b-Wave amplitude (Vmax) | 0.01 | [−0.02; 0.05] | | | | |
| Model 7h | | | | | | |
| intercept | 9.72 | [−0.79; 29.04] | 0.13 | 0.71 | 93% | 14% |
| age | 0.03 | [−0.09; 0.16] | | | | |
| gender[b] | −0.13 | [−1.36; 1.09] | | | | |
| rod b-Wave implicit time (int2) | −0.20 | [−0.62; 0.02] | | | | |
| SZ taking ability without clozapine | | | | | | |
| Best model of the multiple logistic regression (model 8) | | | 0.28 | 0.84 (FIG. 3D) | 80% | 60% |
| intercept | 7.85 | [−1.23; 21.72] | | | | |
| age | −0.13 | [−0.40; 0.05] | | | | |
| gender[b] | 1.11 | [−0.70; 4.04] | | | | |
| rod a-Wave amplitude (Vmax) | −0.19 | [−0.61; 0.02] | | | | |
| Models of the simple logistic regression | | | | | | |
| Model 9a | | | | | | |
| intercept | 3.66 | [−3.06; 12.61] | 0.13 | 0.68 | 60% | 80% |
| age | 0.02 | [−0.17; 0.25] | | | | |
| gender[b] | −0.29 | [−2.21; 1.29] | | | | |
| cone a-Wave amplitude (Vmax) | −0.21 | [−0.91; 0.16] | | | | |
| Model 9b | | | | | | |
| intercept | 4.38 | [−17.8; 33.9] | 0.04 | 0.64 | 40% | 60% |
| age | −0.04 | [−0.20; 0.11] | | | | |
| gender[b] | 0.13 | [−1.27; 1.77] | | | | |
| cone a-Wave implicit time (Vmax) | −0.20 | [−2.09; 1.28] | | | | |
| Model 9c | | | | | | |
| intercept | −3.38 | [−17.6; 5.91] | 0.18 | 0.72 | 60% | 80% |
| age | −0.01 | [−0.19; 0.15] | | | | |
| gender[b] | −0.44 | [−2.72; 1.21] | | | | |
| cone b-Wave amplitude (3-int) | 0.05 | [−0.02; 0.18] | | | | |
| Model 9d | | | | | | |
| intercept | 23.85 | [−27.9; 91.5] | 0.10 | 0.68 | 60% | 80% |
| age | −0.03 | [−0.20; 0.12] | | | | |
| gender[b] | 0.12 | [−1.27; 1.58] | | | | |
| cone b-Wave implicit time (int1) | −0.77 | [−3.05; 1.01] | | | | |

TABLE 6A-continued

Parameter estimates of the multiple logistic regression to predict the good responders to treatment

| Good vs. Poor intermediate response | Parameter estimate | | | | | |
|---|---|---|---|---|---|---|
| Parameter(flash intensity[a]) | Value | 95% CI | $R^2$ | AUC | Sensitivity | Specificity |
| Model 9e | | | | | | |
| intercept | −23.21 | [−107.3; 3.55] | 0.30 | 0.84 | 60% | 80% |
| age | −0.16 | [−0.62; 0.05] | | | | |
| gender[b] | 0.29 | [−1.28; 2.39] | | | | |
| rod a-Wave implicit time (int2) | 1.19 | [−0.05; 5.32] | | | | |
| Model 9f | | | | | | |
| intercept | 0.12 | [−7.93; 7.75] | 0.06 | 0.64 | 60% | 60% |
| age | −0.04 | [−0.21; 0.10] | | | | |
| gender[b] | −0.08 | [−1.62; 1.43] | | | | |
| rod b-Wave amplitude (int2) | 0.01 | [−0.02; 0.05] | | | | |
| Model 9g | | | | | | |
| intercept | −1.72 | [−10.21; 6.19] | 0.16 | 0.64 | 60% | 60% |
| age | 0.01 | [−1.55; 1.60] | | | | |
| gender[b] | −0.10 | [−0.38; 0.07] | | | | |
| rod b-Wave implicit time (Vmax) | 0.08 | [−0.04; 0.28] | | | | |

[a] In the photopic ERG, the peak maximal response correspond to the « Vmax », « int1 » correspond to a fixed intensity of 7.5 cd × s/m$^2$ and « 3-int » correspond to an average of three intensities. For the rod function (scotopic ERG), « Vmax » refer to the saturating amplitude observed at the first plateau, where rods only are involved in the response (flash intensity of 0.1 cd × s/m$^2$) and « int2 » refer to a flash intensity of 1 cd × s/m$^2$.
[b] Female = 1 and male = 0
[c] When more than one model based on the same number of ERG parameters was possible, only the model that provided the higher accuracy according to the AUC is presented.

TABLE 6B

Prediction of good response to any medication in the total sample of 150 SZ patients

| As predicted | Observed response to treatment | | |
|---|---|---|---|
| by the ERGs | Good | Poor-Intermediate | |
| Good response | 61% (39) | 29% (20) | |
| Poor-Intermediate response | 39% (25) | 71% (48) | |
| Total | 64 | 68 | OR = 3.7 |

TABLE 6C

Prediction of good response to olanzapine without taking clozapine

| As predicted | Observed response to treatment | | |
|---|---|---|---|
| by the ERGs | Good | Poor-Intermediate | |
| Good response | 100% (15) | 0% | |
| Poor-Intermediate response | 0% | 100% (10) | |
| Total | 15 | 10 | OR = ∞ |

TABLE 6D

Prediction of good response to quetiapine without taking clozapine

| As predicted | Observed response to treatment | | |
|---|---|---|---|
| by the ERGs | Good | Poor-Intermediate | |
| Good response | 87% (13) | 14% (1) | |
| Poor-Intermediate response | 13% (2) | 86% (6) | |
| Total | 15 | 7 | OR = 39 |

TABLE 6E

Prediction of good response to aripiprazole (Abilify ®) without taking clozapine

| As predicted | Observed response to treatment | | |
|---|---|---|---|
| by the ERGs | Good | Poor-Intermediate | |
| Good response | 80% (4) | 60% (3) | |
| Poor-Intermediate response | 20% (1) | 40% (2) | |
| Total | 5 | 5 | OR = 6 |

Example 4: ERG Profiling in Patients with Schizophrenia or Bipolar Disorder

Study Subjects for the Schizophrenia/Bipolar Disorders Studies.

The characteristics of the affected SZ, BP and control subjects are depicted in Table 7.

TABLE 7

Characteristics of the sample: 150
SZ, 151 BP and 150 controls (CT)

|  | SZ cases (N = 150) | BP cases (N = 151) | Controls (N = 150) |
|---|---|---|---|
|  | Mean (SD) or N (%) | | |
| Age | 39.4 (9.9) | 40.8 (10.1) | 40.6 (9.5) |
| % Male*** | 80% | 40% | 62% |
| Age of onset*** | 25.0 (6.4) | 28.7 (9.0) | — |
| Duration of illness* | 13.8 (9.2) | 11.6 (7.7) | — |
| GAS (T3)$^a$ | — | 67.2 (7.4) | |
| GAS (T1)$^a$ | — | 38.1 (12.2) | |
| GAS-S (T3)$^a$ | 52.5 (8.8) | — | — |
| GAS-S (T1)$^a$ | 29.4 (10.1) | — | — |
| Olanzapine | 28 (19%) | 17 (11%) | 0 |
| Quetiapine | 32 (21%) | 45 (30%) | 0 |
| Clozapine | 45 (30%) | 4 (3%) | 0 |
| Risperidone | 34 (23%) | 21 (14%) | 0 |
| Abilify | 12 (8%) | 23 (15%) | 0 |
| Lithium | 7 (5%) | 66 (44%) | 0 |
| Synthroid | 1 (.7%) | 26 (17%) | 0 |

P-value of the comparison between groups:
*<0.05,
**<0.01
***<0.0001
$^a$GAS for lifetime Global assessment scale, GAS-S for lifetime Global Assessment Scale - Severity, at two different periods: - the time of first admission or first episode of illness (T1), - the last 6 to 24 months before the ERG recording (T3).

The univariate comparisons of BP patients versus controls and SZ patients, on each of the ERG parameters are depicted in Table 8. As can be seen in the section "Effect size (p-value)" of Table 8, the BP subjects differ significantly (p<0.001) from controls on at least six ERG parameters (cone a-wave implicit time, cone b-wave implicit time, rod a-wave amplitude, rod a-wave implicit time, rod b-wave amplitude and rod log K) with effect sizes ranging from 0.46 to 1.23 (in absolute value). Moreover, the BP subjects differ significantly (p<0.002) from SZ subjects on at least five ERG parameters (cone a-wave amplitude, cone a-wave implicit time, cone b-wave amplitude, rod a-wave implicit time and rod log K) with effect sizes ranging from 0.37 to 0.68 (in absolute value). These univariate results show that prediction modeling based on multiple logistic regression may detect a judicious subset of ERG parameters that best predict the group membership, as detailed below.

For the prediction modeling of BP vs. control subjects (CT), the multiple logistic regression identified a model based on six ERG parameters that best predicted if a subject has BP with an overall accuracy of 0.93, a sensitivity of 86%, a specificity of 87% (see Table 9A) and a corresponding OR of 43 (see Table 9B). The final model (see model 1 in Table 9A) fitted the following equation:

$$\text{Log}[P(BP)/(1-P(BP))] = -14.15 + 0.57(\text{gender}) - 0.002(\text{age}) + 1.46(\text{phBlat}) - 1.24(\text{scAlat}) - 0.03(\text{scBamp}) + 0.17(\text{scBlat}) + 0.04(\text{phBamp}) - 0.55(\text{phAlat})$$

in which:
gender=1 if the subject is a female and 0 if the subject is a male;
phBlat=cone b-Wave implicit time, average of three intensities (3-int);
scAlat=rod a-Wave implicit time, flash intensity of 1 cd×s/m² (int2);
scBamp=rod b-Wave amplitude, flash intensity of 1 cd×s/m² (int2);
scBlat=rod a-Wave implicit time, flash intensity of 1 cd×s/m² (int2);
phBamp=cone b-Wave amplitude, peak maximal response (Vmax);
phAlat=cone a-Wave implicit time, average of three intensities (3-int).

The prediction modeling of SZ versus BP subjects identified four ERG parameters (cone a-Wave amplitude, rod a-Wave implicit time (int2), rod b-Wave amplitude and rod a-Wave implicit time (Vmax)). The model had an accuracy of 0.83, a sensitivity of 78%, a specificity of 76% (see model 7 in Table 9A) and a corresponding OR of 11 (see Table 9C). The final model (model 7 in Table 9A) fitted the following equation:

$$\text{Log}[P(SZ)/(1-P(SZ))] = -4.26 - 0.91(\text{gender}) - 0.04(\text{age}) - 0.18(\text{phAamp}) + 0.08(\text{scAlat}) + 0.01(\text{scBamp}) + 0.22(\text{scAlat})$$

in which:
phAamp=cone a-Wave amplitude, average of three intensities (3-int)
scAlat=rod a-Wave implicit time, peak maximal response (Vmax)

TABLE 8

Intergroup comparison between (i) BP and CT, and (ii) SZ and BP
for the 8 ERG parameters (gender- and age-adjusted)

| ERG parameters | Flash intensity$^a$ | Mean (SD) | | | Effect size (p-value) | |
|---|---|---|---|---|---|---|
| | | BP (N = 151) | CTL (N = 150) | SZ (N = 150) | BP/CT | BP/SZ |
| Cones | | | | | | |
| a-Wave amplitude | 3-int | 23.74 (5.2) | 24.24 (5.1) | 20.79 (5.6) | 0.08 0.5018 | 0.68 <0.001 |
| a-Wave implicit time | 3-int | 14.22 (1) | 14.8 (0.9) | 14.59 (1) | 0.62 <0.001 | -0.37 0.0016 |
| b-Wave amplitude | int1 | 71.99 (17.5) | 71.17 (18) | 65.85 (19.7) | -0.07 0.5318 | 0.38 0.0010 |
| b-Wave implicit time | 3-int | 32.67 (1.1) | 31.22 (1.3) | 32.93 (1.4) | -1.23 <0.001 | -0.12 0.2965 |
| Rods | | | | | | |
| a-Wave amplitude | int2 | 58.92 (24) | 70.76 (24.3) | 58.85 (26.6) | 0.46 0.0001 | 0.13 0.2541 |
| a-Wave implicit time | int2 | 23.89 (1.3) | 24.82 (1.6) | 24.66 (1.7) | 0.74 <0.001 | -0.46 0.0001 |
| b-Wave amplitude | int2 | 173.09 (41.6) | 203.10 (43) | 175.26 (47.1) | 0.70 <0.001 | 0.02 0.8677 |
| b-Wave implicit time | int2 | 48.34 (4.4) | 47.63 (4.2) | 48.74 (4.6) | -0.12 0.2807 | -0.13 0.2676 |
| logK | — | 2.23 (0.2) | 2.11 (0.2) | 2.13 (0.2) | -0.80 <0.001 | 0.50 <0.001 |

Note that all values are adjusted for age and gender.
$^a$In the photopic ERG, the peak maximal response correspond to the « Vmax », « int1 » correspond to a fixed intensity of 7.5 cd × s/m² and « 3-int » correspond to an average of three intensities. For the rod function (scotopic ERG), « Vmax » refer to the saturating amplitude observed at the first plateau, where rods only are involved in the response (flash intensity of 0.1 cd × s/m²) and « int2 » refer to a flash intensity of 1 cd × s/m².

scBamp=rod b-Wave amplitude, peak maximal response (Vmax)

scAlat=rod a-Wave implicit time, flash intensity of 1 cd×s/m² (int2)

Table 9A also shows that other models including fewer ERG parameters (strictly 1, or exactly 2 or 3 or 4) may also predict BP versus controls or SZ subjects, but generally with lesser accuracy.

TABLE 9A

Parameter estimates of the multiple logistic regression to predict the group

Figure 2B:
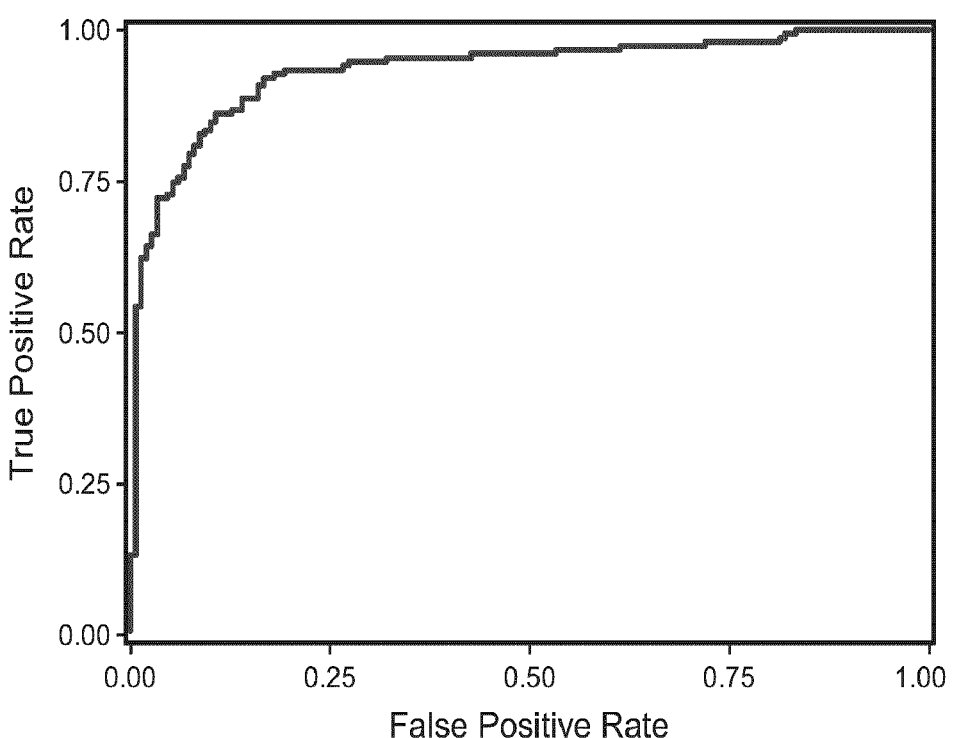
FIG. 2B is the ROC curve of the model predicting bipolar subjects (BP) based on 6 ERG parameters (see Table 9A), with an AUC of 93% corresponding to a sensitivity of 86% and a specificity of 87%.

| Parameter estimate Parameter(flash intensity[a]) | Value | 95% CI | $R^2$ | AUC | Sensitivity | Specificity |
|---|---|---|---|---|---|---|
| BP Vs CT | | | | | | |
| Best model of the multiple logistic regression (model 1) | | | 0.52 | 0.93 | 86% | 87% |
| intercept | −14.15 | [−26.2; −2.8] | | (FIG. 2B) | | |
| age | −0.002 | [−0.04; 0.04] | | | | |
| gender[b] | 0.57 | [0.19; 0.97] | | | | |
| cone b-Wave implicit time (3-int) | 1.46 | [1.08; 1.90] | | | | |
| rod a-Wave implicit time (int2) | −1.24 | [−1.69; −0.83] | | | | |
| rod b-Wave amplitude (int2) | −0.03 | [−0.04; −0.02] | | | | |
| rod b-Wave implicit time (int2) | 0.17 | [0.06; 0.28] | | | | |
| cone b-Wave amplitude (Vmax) | 0.04 | [0.01; 0.06] | | | | |
| cone a-Wave implicit time (3-int) | −0.55 | [−0.99; −0.14] | | | | |
| Models of the simple logistic regression | | | | | | |
| Model 2a | | | | | | |
| intercept | 1.01 | [−0.26; 2.31] | 0.08 | 0.66 | 64% | 62% |
| age | 0.01 | [−0.01; 0.04] | | | | |
| gender[b] | 0.48 | [0.25; 0.73] | | | | |
| cone a-Wave amplitude (Vmax) | −0.06 | [−0.11; −0.03] | | | | |
| Model 2b | | | | | | |
| intercept | 8.86 | [5.2; 12.73] | 0.13 | 0.71 | 66% | 67% |
| age | 0.02 | [0; 0.05] | | | | |
| gender[b] | 0.37 | [0.13; 0.62] | | | | |
| cone a-Wave implicit time (3-int) | −0.67 | [−0.95; −0.41] | | | | |
| Model 2c | | | | | | |
| intercept | 1.49 | [−0.17; 3.19] | 0.07 | 0.66 | 61% | 66% |
| age | 0.00 | [−0.02; 0.03] | | | | |
| gender[b] | 0.54 | [0.29; 0.79] | | | | |
| cone b-Wave amplitude (3-int) | −0.02 | [−0.03; 0] | | | | |
| Model 2d | | | | | | |
| intercept | −35.34 | [−44.7; −26.9] | 0.31 | 0.83 | 75% | 75% |
| age | −0.04 | [−0.07; −0.01] | | | | |
| gender[b] | 0.56 | [0.28; 0.84] | | | | |
| cone b-Wave implicit time (3-int) | 1.16 | [0.88; 1.47] | | | | |
| Model 2e | | | | | | |
| intercept | 1.50 | [0.15; 2.9] | 0.10 | 0.68 | 60% | 66% |
| age | 0.00 | [−0.03; 0.02] | | | | |
| gender[b] | 0.50 | [0.26; 0.75] | | | | |
| rod a-Wave amplitude (int2) | −0.02 | [−0.03; −0.01] | | | | |
| Model 2f | | | | | | |
| intercept | 13.62 | [8.89; 18.73] | 0.16 | 0.74 | 70% | 69% |
| age | 0.03 | [0.01; 0.06] | | | | |
| gender[b] | 0.32 | [0.07; 0.57] | | | | |
| rod a-Wave implicit time (int2) | −0.61 | [−0.83; −0.41] | | | | |
| Model 2g | | | | | | |
| intercept | 2.98 | [1.44; 4.61] | 0.15 | 0.74 | 70% | 68% |
| age | 0.01 | [−0.02; 0.04] | | | | |
| gender[b] | 0.66 | [0.4; 0.94] | | | | |
| rod b-Wave amplitude (int2) | −0.02 | [−0.02; −0.01] | | | | |
| Model 2h | | | | | | |
| intercept | −0.98 | [−2.56; 0.57] | 0.05 | 0.63 | 60% | 61% |
| age | 0.00 | [−0.02; 0.03] | | | | |
| gender[b] | 0.46 | [0.23; 0.7] | | | | |
| rod b-Wave implicit time (Vmax) | 0.01 | [−0.01; 0.03] | | | | |
| Model based on 2 ERG parameters (Model 3)[c] | | | | | | |
| intercept | −21.90 | [−32.21; −12.37] | 0.43 | 0.89 | 79% | 81% |
| age | −0.01 | [−0.05; 0.02] | | | | |
| gender[b] | 0.42 | [0.11; 0.73] | | | | |
| cone b-Wave implicit time (3-int) | 1.39 | [1.06; 1.75] | | | | |
| rod a-Wave implicit time (int2) | −0.90 | [−1.19; −0.63] | | | | |

TABLE 9A-continued

Parameter estimates of the multiple logistic regression to predict the group

Figure 2C:
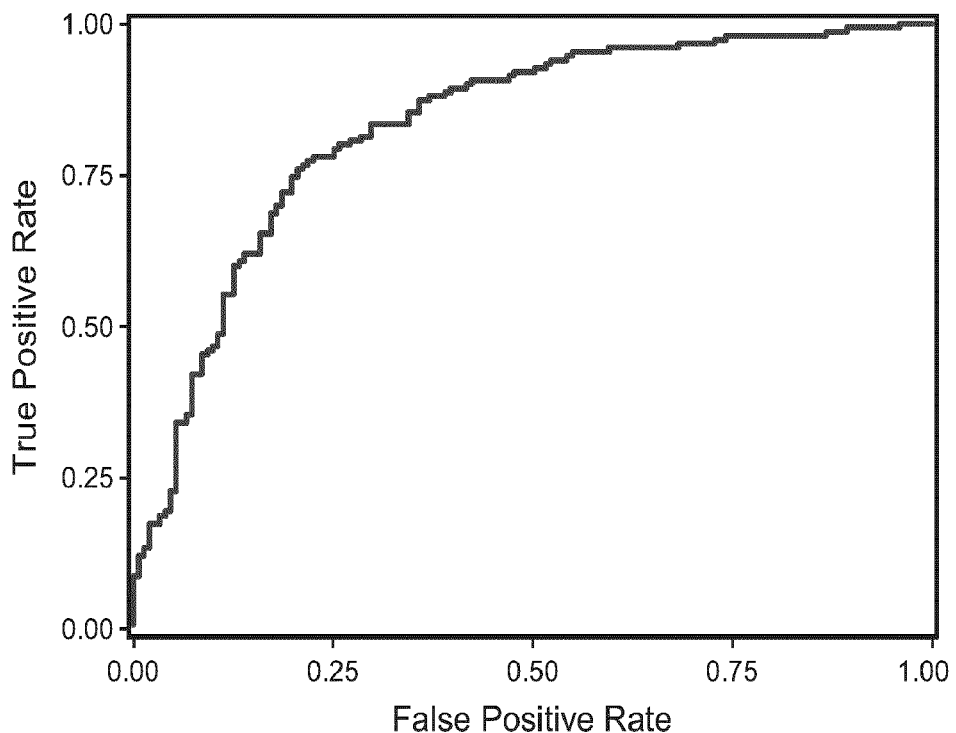
FIG. 2C is the ROC curve of the model predicting SZ subjects relative to BP subjects based on 4 ERG parameters (see Table 9A), with an AUC of 83% corresponding to a sensitivity of 78% and a specificity of 76%.

| Parameter estimate Parameter(flash intensity[a]) | Value | 95% CI | $R^2$ | AUC | Sensitivity | Specificity |
|---|---|---|---|---|---|---|
| Model based on 3 ERG parameters (Model 4)[c] | | | | | | |
| intercept | −7.30 | [−19.22; 4.37] | 0.48 | 0.92 | 82% | 87% |
| age | −0.02 | [−0.06; 0.02] | | | | |
| gender[b] | 0.48 | [0.15; 0.83] | | | | |
| cone b-Wave implicit time (3-int) | 1.34 | [1.01; 1.73] | | | | |
| rod a-Wave implicit time (int2) | −1.30 | [−1.69; −0.96] | | | | |
| rod a-Wave amplitude (int2) | −0.05 | [−0.07; −0.03] | | | | |
| Model based on 4 ERG parameters (Model 5)[c] | | | | | | |
| intercept | −14.07 | [−25.57; −3.1] | 0.50 | 0.92 | 84% | 87% |
| age | 0.00 | [−0.04; 0.04] | | | | |
| gender[b] | 0.65 | [0.29; 1.02] | | | | |
| rod a-Wave implicit time (int2) | −0.89 | [−1.25; −0.56] | | | | |
| rod b-Wave amplitude (int2) | −0.02 | [−0.03; −0.01] | | | | |
| cone b-Wave implicit time (3-int) | 1.49 | [1.13; 1.92] | | | | |
| cone a-Wave implicit time (3-int) | −0.55 | [−0.96; −0.15] | | | | |
| Model based on 5 ERG parameters (Model 6)[c] | | | | | | |
| intercept | −16.42 | [−28.44; −5.1] | 0.51 | 0.93 | 85% | 88% |
| age | 0.01 | [−0.03; 0.05] | | | | |
| gender[b] | 0.54 | [0.17; 0.93] | | | | |
| cone b-Wave amplitude (Vmax) | 0.03 | [0.01; 0.06] | | | | |
| rod a-Wave implicit time (int2) | −0.92 | [−1.28; −0.59] | | | | |
| rod b-Wave amplitude (int2) | −0.03 | [−0.04; −0.02] | | | | |
| cone a-Wave implicit time (3-int) | −0.54 | [−0.96; −0.14] | | | | |
| cone b-Wave implicit time (3-int) | 1.53 | [1.16; 1.96] | | | | |
| SZ Vs BP | | | | | | |
| Best model of the multiple logistic regression (Model 7) | | | 0.31 | 0.83 | 78% | 76% |
| intercept | −4.26 | [−9.08; 0.42] | | (FIG. 2C) | | |
| age | −0.04 | [−0.07; −0.01] | | | | |
| gender[b] | −0.91 | [−1.21; −0.61] | | | | |
| cone a-Wave amplitude (3-int) | −0.18 | [−0.24; −0.11] | | | | |
| rod a-Wave implicit time (Vmax) | 0.08 | [0.01; 0.16] | | | | |
| rod b-Wave amplitude (Vmax) | 0.01 | [0.003; 0.02] | | | | |
| rod a-Wave implicit time (int2) | 0.22 | [0.01; 0.44] | | | | |
| Models of the simple logistic regression | | | | | | |
| Model 8a | | | | | | |
| intercept | 3.81 | [2.16; 5.56] | 0.25 | 0.80 | 75% | 70% |
| age | −0.02 | [−0.05; 0.01] | | | | |
| gender[b] | −0.92 | [−1.2; −0.65] | | | | |
| cone a-Wave amplitude (3-int) | −0.15 | [−0.21; −0.1] | | | | |
| Model 8b | | | | | | |
| intercept | −4.89 | [−8.44; −1.49] | 0.19 | 0.75 | 78% | 66% |
| age | −0.03 | [−0.05; 0] | | | | |
| gender[b] | −0.87 | [−1.14; −0.61] | | | | |
| cone a-Wave implicit time (3-int) | 0.40 | [0.15; 0.66] | | | | |
| Model 8c | | | | | | |
| intercept | 2.57 | [0.85; 4.34] | 0.19 | 0.77 | 75% | 62% |
| age | −0.03 | [−0.06; 0] | | | | |
| gender[b] | −0.80 | [−1.08; −0.54] | | | | |
| cone b-Wave amplitude (int1) | −0.02 | [−0.04; −0.01] | | | | |
| Model 8d | | | | | | |
| intercept | −9.38 | [−15.1; −3.95] | 0.20 | 0.76 | 79% | 65% |
| age | −0.03 | [−0.06; −0.01] | | | | |
| gender[b] | −0.82 | [−1.09; −0.55] | | | | |
| cone b-Wave implicit time (int1) | 0.36 | [0.16; 0.57] | | | | |
| Model 8e | | | | | | |
| intercept | 0.20 | [−1.09; 1.49] | 0.16 | 0.73 | 81% | 60% |
| age | −0.01 | [−0.04; 0.01] | | | | |
| gender[b] | −0.91 | [−1.17; −0.65] | | | | |
| rod a-Wave amplitude (Vmax) | 0.00 | [−0.02; 0.03] | | | | |

TABLE 9A-continued

Parameter estimates of the multiple logistic regression to predict the group

| Parameter estimate Parameter(flash intensity[a]) | Value | 95% CI | $R^2$ | AUC | Sensitivity | Specificity |
|---|---|---|---|---|---|---|
| Model 8f | | | | | | |
| intercept | −7.62 | [−12.05; −3.5] | 0.21 | 0.77 | 78% | 64% |
| age | −0.03 | [−0.06; −0.01] | | | | |
| gender[b] | −0.81 | [−1.09; −0.55] | | | | |
| rod a-Wave implicit time (int2) | 0.36 | [0.18; 0.56] | | | | |
| Model 8g | | | | | | |
| intercept | 0.42 | [−1.13; 1.97] | 0.16 | 0.73 | 81% | 60% |
| age | −0.01 | [−0.04; 0.01] | | | | |
| gender[b] | −0.90 | [−1.17; −0.64] | | | | |
| rod b-Wave amplitude (int2) | 0.00 | [−0.01; 0.01] | | | | |
| Model 8h | | | | | | |
| intercept | −1.05 | [−3.68; 1.59] | 0.17 | 0.74 | 81% | 60% |
| age | −0.02 | [−0.04; 0.01] | | | | |
| gender[b] | −0.89 | [−1.16; −0.63] | | | | |
| rod b-Wave implicit time (int2) | 0.03 | [−0.02; 0.09] | | | | |
| Model based on 2 ERG parameters (Model 9) G | | | | | | |
| intercept | 0.64 | [−1.75; 3.04] | 0.29 | 0.82 | 77% | 72% |
| age | −0.03 | [−0.06; 0] | | | | |
| gender[b] | −0.86 | [−1.15; −0.58] | | | | |
| rod a-Wave implicit time(Vmax) | 0.13 | [0.06; 0.2] | | | | |
| cone a-Wave amplitude (3-int) | −0.15 | [−0.21; −0.1] | | | | |
| Model based on 3 ERG parameters (Model 10)[c] | | | | | | |
| intercept | −6.01 | [−11.13; −1.1] | 0.30 | 0.83 | 77% | 75% |
| age | −0.04 | [−0.07; −0.01] | | | | |
| gender[b] | −0.95 | [−1.26; −0.65] | | | | |
| rod a-Wave implicit time (int2) | 0.38 | [0.18; 0.58] | | | | |
| cone a-wave amplitude (3-int) | −0.18 | [−0.25; −0.12] | | | | |
| rod b-Wave amplitude (int2) | 0.01 | [0; 0.02] | | | | |

Note that age and gender are included in models as covariate

[a] In the photopic ERG, the peak maximal response correspond to the « Vmax », « int1 » correspond to a fixed intensity of 7.5 cd × s/m2 and « 3-int » correspond to an average of three intensities. For the rod function (scotopic ERG), « Vmax » refer to the saturating amplitude observed at the first plateau, where rods only are involved in the response (flash intensity of 0.1 cd × s/m2) and « int2 » refer to a flash intensity of 1 cd × s/m2.
[b] Female = 1 and male = 0
[c] When more than one model based on the same number of ERG parameters was possible, only the model that provided the higher accuracy according to the AUC is presented.

TABLE 9B

Prediction of BP cases vs. controls

| As predicted by the ERGs | Group sample | | |
|---|---|---|---|
| | BP | CT | |
| BP | 130 (86%) | 19 (13%) | |
| CT | 21 (14%) | 131 (87%) | |
| Total | 151 | 150 | OR = 43 |

TABLE 9C

Prediction of SZ vs. BP cases

| As predicted by the ERGs | Group sample | | |
|---|---|---|---|
| | SZ | BP | |
| SZ | 117 (78%) | 36 (24%) | |
| BP | 33 (22%) | 115 (76%) | |
| Total | 150 | 151 | OR = 11 |

Example 5: ERG Profiling in Patients with Major Depression (MDD)

Results based on a group of 21 MDD subjects are presented in Table 10. The univariate comparison of MDD patients to controls, on each of the ERG parameters shows that two ERG parameters significantly distinguished these two groups with p values below 0.01 (rod a-wave amplitude, ES=0.72, p=0.002; and rod b-wave amplitude, ES=0.64, p=0.007), and two other ERG parameters, cone a-Wave amplitude and rod b-Wave implicit time, showing a p value below 0.05. When the MDD were compared to the BP subjects, again two ERG parameters showed differences with p-values below 0.01 (cone b-wave implicit time, ES=−0.71, p=0.003; rod a-wave implicit time, ES=0.63, p=0.008). When comparing MDD with SZ subjects, one ERG parameter reached a significant level (cone b-wave implicit time, ES=−0.58, p=0.013), and three important effect sizes above 0.4 were observed, which suggests that other significant differences would be seen in a larger sample. Prediction modeling based on multiple regression was not possible due to the small sample of MDD subjects (N=21).

TABLE 10

Intergroup comparison between (i) MDD and CT, (ii) MDD and BP, and (iii) MDD and SZ for the 8 ERG parameters (gender- and age-adjusted)

| ERG parameters | Flash intensity[a] | Mean (SD) | | Effect size (p-value) | | |
|---|---|---|---|---|---|---|
| | | MDD (N = 21) | CTL (N = 187) | MDD/CT | MDD/BP | MDD/SZ |
| Cones | | | | | | |
| a-Wave amplitude | 3-int | 19.15 (5.1) | 24.15 (5.3) | 0.48 (0.042) | −0.12 (0.604) | 0.45 (0.056) |
| a-Wave implicit time | int1 | 16.04 (1.6) | 15.69 (1.3) | −0.01 (0.955) | 0.13 (0.579) | 0.18 (0.431) |
| b-Wave amplitude | Vmax | 82.43 (18.4) | 91.38 (17.0) | 0.11 (0.624) | 0.27 (0.240) | 0.45 (0.055) |
| b-Wave implicit time | 3-int | 32.3 (1.5) | 31.28 (1.1) | −0.36 (0.128) | −0.71 (0.003) | −0.58 (0.013) |
| Rods | | | | | | |
| a-Wave amplitude | Int1 | 47.31 (23.6) | 70.08 (25.6) | 0.72 (0.002) | −0.16 (0.501) | −0.41 (0.079) |
| a-Wave implicit time | int2 | 25.02 (1.8) | 24.60 (1.4) | 0.02 (0.947) | 0.63 (0.008) | 0.08 (0.723) |
| b-Wave amplitude | Int1 | 174.5 (42.6) | 199.50 (40.8) | 0.64 (0.007) | 0.18 (0.436) | 0.13 (0.569) |
| b-Wave implicit time | int2 | 48.84 (6.5) | 47.55 (5.6) | 0.26 (0.025) | −0.23 (0.323) | −0.26 (0.275) |

Note that all values are adjusted for age and gender.
[a]In the photopic ERG, the peak maximal response correspond to the « Vmax », « int1 » correspond to a fixed intensity of 7.5 cd × s/m$^2$ and « 3-int » correspond to an average of three intensities. For the rod function (scotopic ERG), « Vmax » refer to the saturating amplitude observed at the first plateau, where rods only are involved in the response (flash intensity of 0.1 cd × s/m$^2$) and « int2 » refer to a flash intensity of 1 cd × s/m$^2$.

Example 6: ERG Profiling in Offspring (Mental Disorders)

Nonaffected young high-risk offspring (HR) of parents affected by SZ or BP were targeted in well characterized multigenerational families of Eastern Quebec (Maziade, 2005). Fifty-two HR subjects were enrolled. A sample of 57 unrelated healthy control subjects balanced for age and gender were selected form the same population. We compared the HR offspring to control subjects on each of the eight ERG parameters by means of ANCOVA (univariate analysis; see Table 11). To address the possible effect of lack of independence among observations due to some of the offspring who were sibs, multilevel modeling was carried out using the group assessment (HR vs. CT) as a first level and the sibship nested in the group as a second random level. In this multilevel modeling (Goldstein, 1998), age and gender were also adjusted. This univariate analysis revealed that four ERG parameters (rod a-wave amplitude, ES=−0.59, p=0.003; rod a-wave implicit time, ES=0.55, p=0.005; rod b-wave amplitude, ES=−0.7, p=0.0006; rod b-wave implicit time, ES=0.68, p=0.0006) significantly distinguished these two groups.

TABLE 11

Comparison of 52 HR of SZ or BP patients to 57 controls on ERG parameters

| ERG parameters[a] | Flash intensity[b] | Mean (SD) | | Effect size | P-value |
|---|---|---|---|---|---|
| | | 52 HR | 57 CT | | |
| Cones | | | | | |
| a-Wave amplitude | int1 | 14.84 (4) | 16.65 (5.4) | −0.31 | 0.1086 |
| a-Wave implicit time | Vmax | 14.27 (1.2) | 14.42 (1.2) | −0.11 | 0.5759 |
| b-Wave amplitude | int1 | 81.30 (16.6) | 83.58 (21.6) | −0.13 | 0.5007 |
| b-Wave implicit time | int1 | 27.79 (1) | 27.31 (0.8) | 0.46 | 0.0200 |
| Rods | | | | | |
| a-Wave amplitude | int2 | 61.36 (26) | 77.32 (21) | −0.59 | 0.0032 |
| a-Wave implicit time | int2 | 23.88 (2) | 22.90 (1.1) | 0.55 | 0.0054 |
| b-Wave amplitude | int2 | 165.77 (35.8) | 192.77 (33.6) | −0.70 | 0.0006 |
| b-Wave implicit time | Vmax | 70.07 (10.5) | 63.32 (7.7) | 0.68 | 0.0006 |

[a]Note that age and gender are included in all models as covariate
[b]In the photopic ERG, the peak maximal response correspond to the « Vmax », « int1 » correspond to a fixed intensity of 7.5 cd × s/m$^2$ and « 3-int » correspond to an average of three intensities. For the rod function (scotopic ERG), « Vmax » refer to the saturating amplitude observed at the first plateau, where rods only are involved in the response (flash intensity of 0.1 cd × s/m$^2$) and « int2 » refer to a flash intensity of 1 cd × s/m$^2$.

The prediction modeling (using multiple logistic regression) identified a model based on three ERG parameters that best predict if a subject is HR with an overall accuracy of 0.86, a sensitivity of 71%, a specificity of 74% (see model 1 in Table 12A) and a corresponding OR of 7 (see Table 12B). Table 12A also shows that other models including fewer ERG parameters (strictly 1, or exactly 2) can possibly predict HR versus control subjects, but with lesser accuracy.

TABLE 12A

Parameter estimates of the multiple logistic regression to predict HR offspring to control subjects

Figure 3E:
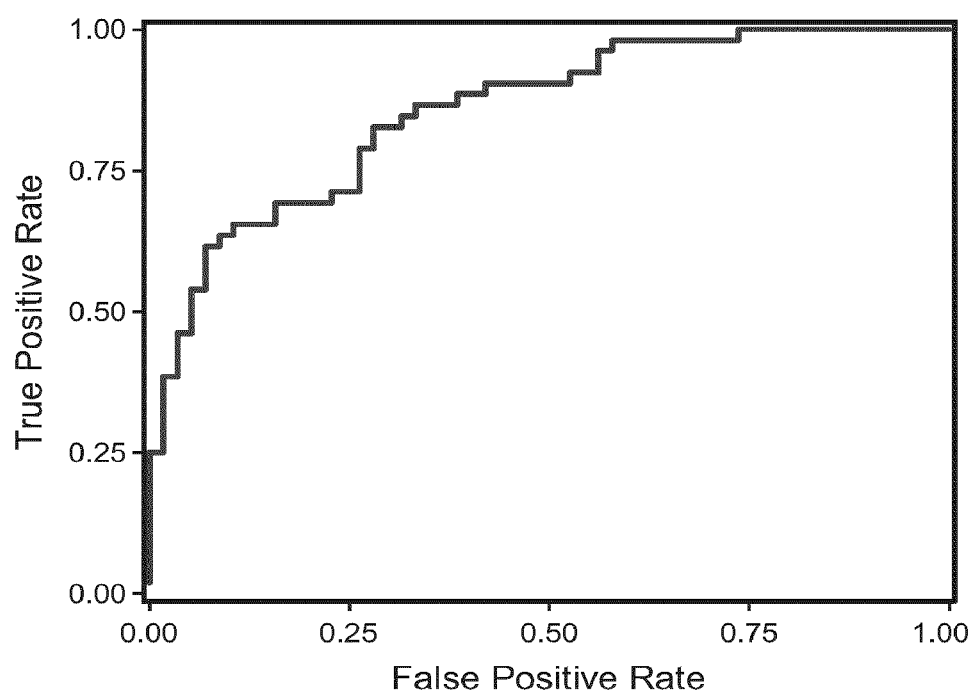
FIG. 3E is the receiving operating characteristic [ROC] curve of the model predicting HR offspring relative to control subjects, based on three ERG parameters (see Table 12A), with an AUC of 86% corresponding to a sensitivity of 71% and a specificity of 74%.

| Parameter(Flash intensity[a]) | Parameter estimate Value | 95% CI | $R^2$ | AUC | Sensitivity | Specificity |
|---|---|---|---|---|---|---|
| Best model of the multiple logistic regression (model 1) | | | 0.36 | 0.86 (FIG. 3E) | 71% | 74% |
| intercept | −16.35 | [−27.5; −6.60] | | | | |
| age | 0.20 | [0.10; 0.31] | | | | |
| gender[b] | 0.36 | [−0.18; 0.94] | | | | |
| rod b-Wave amplitude (int2) | −0.05 | [−0.07; −0.03] | | | | |
| cone b-Wave implicit time (Vmax) | 0.50 | [0.19; 0.85] | | | | |
| cone b-Wave amplitude (Vmax) | 0.07 | [0.02; 0.12] | | | | |
| Models of the simple logistic regression | | | | | | |
| Model 2a | | | | | | |
| intercept | −1.45 | [−3.49; 0.49] | 0.17 | 0.73 | 67% | 72% |
| age | 0.14 | [0.07; 0.22] | | | | |
| gender[b] | 0.22 | [−0.22; 0.67] | | | | |
| cone a-Wave amplitude (int1) | −0.09 | [−0.19; 0.01] | | | | |
| Model 2b | | | | | | |
| intercept | −3.74 | [−8.04; −0.45] | 0.14 | 0.72 | 63% | 67% |
| age | 0.13 | [0.06; 0.21] | | | | |
| gender[b] | 0.07 | [−0.34; 0.48] | | | | |
| cone a-Wave implicit time (int1) | 0.07 | [−0.15; 0.34] | | | | |
| Model 2c | | | | | | |
| intercept | −1.86 | [−4.9; 1.06] | 0.14 | 0.72 | 63% | 68% |
| age | 0.13 | [0.06; 0.21] | | | | |
| gender[b] | 0.16 | [−0.31; 0.64] | | | | |
| cone b-Wave amplitude (int1) | −0.01 | [−0.04; 0.02] | | | | |
| Model 2d | | | | | | |
| intercept | −20.38 | [−35.1; −7.17] | 0.19 | 0.76 | 69% | 68% |
| age | 0.13 | [0.06; 0.21] | | | | |
| gender[b] | 0.20 | [−0.23; 0.65] | | | | |
| cone b-Wave implicit time (int1) | 0.64 | [0.16; 1.17] | | | | |
| Model 2e | | | | | | |
| intercept | −0.75 | [−2.67; 1.16] | 0.22 | 0.77 | 63% | 70% |
| age | 0.15 | [0.07; 0.23] | | | | |
| gender[b] | 0.29 | [−0.16; 0.75] | | | | |
| rod a-Wave amplitude (int2) | −0.03 | [−0.05; −0.01] | | | | |
| Model 2f | | | | | | |
| intercept | −11.56 | [−19.9; −4.93] | 0.20 | 0.76 | 65% | 74% |
| age | 0.14 | [0.06; 0.22] | | | | |
| gender[b] | 0.09 | [−0.33; 0.52] | | | | |
| rod a-Wave implicit time (int2) | 0.38 | [0.10; 0.73] | | | | |
| Model 2g | | | | | | |
| intercept | 0.86 | [−1.63; 3.49] | 0.24 | 0.79 | 75% | 77% |
| age | 0.15 | [0.07; 0.23] | | | | |
| gender[b] | 0.29 | [−0.16; 0.75] | | | | |
| rod b-Wave amplitude (Vmax) | −0.03 | [−0.04; −0.01] | | | | |
| Model 2h | | | | | | |
| intercept | −8.47 | [−12.9; −4.77] | 0.23 | 0.79 | 71% | 75% |
| age | 0.13 | [0.06; 0.21] | | | | |
| gender[b] | 0.13 | [−0.30; 0.57] | | | | |
| rod b-Wave implicit time (Vmax) | 0.09 | [0.04; 0.15] | | | | |
| Model based on 2 ERG parameters (model 3)[c] | | | | | | |
| intercept | −5.72 | [−10.2; −1.35] | 0.33 | .85 | 77% | 82% |
| age | 0.14 | [0.06; 0.23] | | | | |
| gender[b] | 0.35 | [−0.13; 0.85] | | | | |
| rod b-Wave amplitude (Vmax) | −0.03 | [−0.04; −0.01] | | | | |
| rod b-Wave implicit time (Vmax) | 0.10 | [0.05; 0.16] | | | | |

[a]In the photopic ERG, the peak maximal response correspond to the « Vmax », « int1 » correspond to a fixed intensity of 7.5 cd × s/m² and « 3-int » correspond to an average of three intensities. For the rod function (scotopic ERG), « Vmax » refer to the saturating amplitude observed at the first plateau, where rods only are involved in the response (flash intensity of 0.1 cd × s/m²) and « int2 » refer to a flash intensity of 1 cd × s/m².
[b]Female = 1 and male = 0
[c]When more than one model based on the same number of ERG parameters was possible, only the model that provided the higher accuracy according to the AUC is presented.

TABLE 12B

Prediction of HR offspring vs. control subjects

| As predicted by the ERGs | Group sample | | |
|---|---|---|---|
| | HR | CT | |
| HR | 37 (71%) | 15 (26%) | |
| CT | 15 (29%) | 42 (74%) | |
| Total | 52 | 57 | OR = 7 |

Example 7: ERG Profiling in SZ and BP Patients with 5 Years or Less of Disease Duration An important issue in modern psychiatric practice remains for the clinician to get a reliable diagnosis for his patient: during the first years after disease incidence, the presentation of illness renders the diagnosis difficult to establish. Since treatment decisions rely on the diagnosis, such difficulties have impacts on the patient's prognosis and treatment orientation.

The same approach was thus applied to younger patients, having shorter durations of illness (≤5 years), i.e. narrowing down on the period of illness when the mental health practitioner needs the most aid to determine the suitable treatment of the patient. Table 13 shows a comparison of the eight ERG parameters by means of ANCOVA (univariate analysis) in 37 SZ patients with 5 years or less of disease duration and 37 controls matched for age.

TABLE 13

Comparison of ERG parameters in 37 SZ patients with 5 years or less of disease duration and 37 controls matched for age

| ERG parameters | Flash intensity[a] | Mean (SD) | | Effect size | P-value |
|---|---|---|---|---|---|
| | | 37 SZ | 37 CT | | |
| Cones | | | | | |
| a-Wave amplitude* | int1 | 11.62 (5.3) | 16.52 (4.6) | 1.07 | <0.0001 |
| a-Wave implicit time | int1 | 14.58 (1.8) | 15.68 (1.5) | 0.70 | 0.0035 |
| b-Wave amplitude | 3-int | 84.35 (22.8) | 91.27 (19.5) | 0.35 | 0.1347 |
| b-Wave implicit time | 3-int | 32.47 (1.5) | 30.81 (1.2) | −1.32 | <0.0001 |
| Rods | | | | | |
| a-Wave amplitude | int2 | 62.66 (30.2) | 75.37 (25.7) | 0.49 | 0.0391 |
| a-Wave implicit time | Vmax | 28.36 (4.1) | 30.58 (3.5) | 0.62 | 0.0090 |
| b-Wave amplitude | Vmax | 142.18 (45.3) | 161.73 (38.5) | 0.50 | 0.0343 |
| b-Wave implicit time | int2 | 47.37 (5.1) | 45.82 (4.4) | −0.35 | 0.1345 |

Note that only gender is included as covariate in models, since the controls are matched to SZ for age.
[a]In the photopic ERG, the peak maximal response correspond to the « Vmax », « int1 » correspond to a fixed intensity of 7.5 cd × s/m$^2$ and « 3-int » correspond to an average of three intensities. For the rod function (scotopic ERG), « Vmax » refer to the saturating amplitude observed at the first plateau, where rods only are involved in the response (flash intensity of 0.1 cd × s/m$^2$) and « int2 »refer to a flash intensity of 1 cd × s/m$^2$.
*This ERG parameter showed significant differences between SZ and CT, and SZ and BP in Balogh et al. (2008)

The prediction modeling (using multiple logistic regression) identified a model based on five ERG parameters that best predict if a subject is SZ with an overall accuracy of 0.99, a sensitivity of 95%, a specificity of 92% (see model 1 in Table 14A) and a corresponding OR of 198 (see Table 14B). Table 14A also shows that other models including fewer ERG parameters can possibly predict SZ versus control subjects, but with lesser accuracy.

TABLE 14A

Parameter estimates of the multiple logistic regression to predict SZ patients with 5 years or less of disease duration

Figure 10:
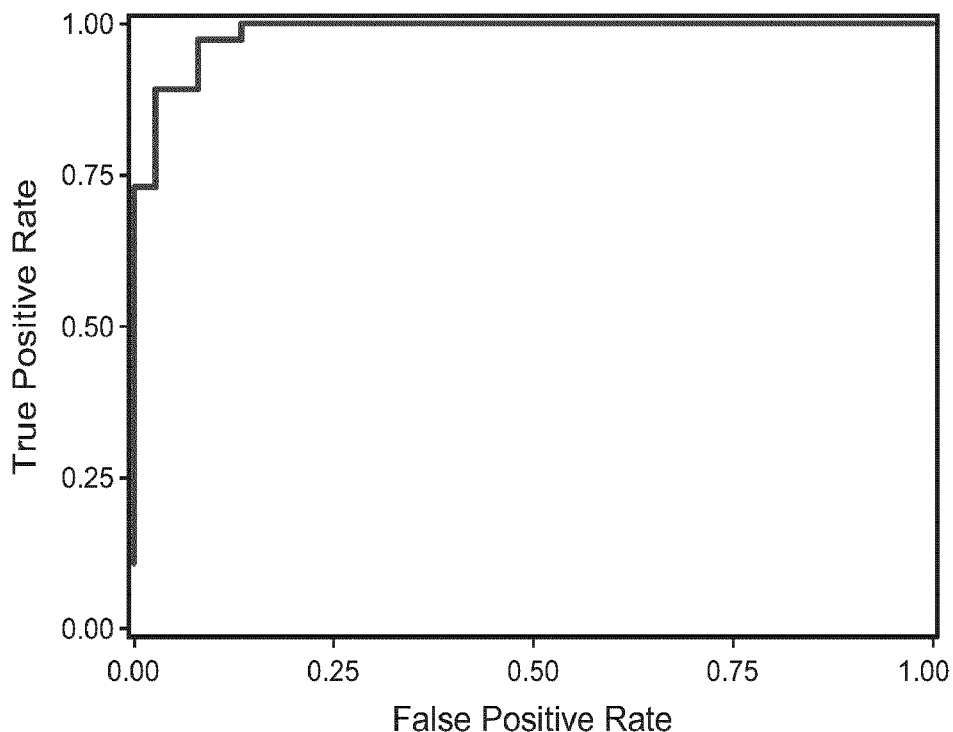
FIG. 10 is the ROC curve of the model predicting SZ subjects with 5 years or less of disease duration vs. matched CT subjects based on five ERG parameters (see Table 14A), with an AUC of 99% corresponding to a sensitivity of 95% and a specificity of 92%.

| Parameter(flash intensity[a]) | Parameter estimate | | $R^2$ | AUC | Sensitivity | Specificity |
|---|---|---|---|---|---|---|
| | Value | 95% CI | | | | |
| SZ with 5 years or less of disease duration vs. matched CT | | | | | | |
| Best model of the multiple logistic regression (model 1) | | | 0.65 | 0.99 (FIG. 10) | 95% | 92% |
| intercept | −51.58 | [−108; −18.1] | | | | |
| gender[b] | −0.17 | [−2.0; 1.54] | | | | |
| cone b-Wave implicit time (3-int) | 8.54 | [4.51; 15.3] | | | | |
| rod a-Wave implicit time (int2) | −4.03 | [−7.6; −1.96] | | | | |
| rod b-Wave amplitude (Vmax) | −0.11 | [−0.21; −0.05] | | | | |
| cone b-Wave implicit time (int1) | −3.96 | [−7.22; −1.74] | | | | |
| cone b-Wave amplitude (3-int) | 0.09 | [0.02; 0.21] | | | | |
| Models of the simple logistic regression | | | | | | |

TABLE 14A-continued

Parameter estimates of the multiple logistic regression to predict
SZ patients with 5 years or less of disease duration

| Parameter(flash intensity[a]) | Parameter estimate Value | 95% CI | $R^2$ | AUC | Sensitivity | Specificity |
|---|---|---|---|---|---|---|
| Model 2a | | | | | | |
| intercept | 3.29 | [1.34; 5.64] | 0.29 | 0.82 | 76% | 78% |
| gender[b] | −0.60 | [−1.36; 0.09] | | | | |
| cone a-Wave amplitude (int1)* | −0.27 | [−0.43; −0.13] | | | | |
| Model 2b | | | | | | |
| intercept | 7.42 | [2.16; 13.62] | 0.19 | 0.73 | 89% | 51% |
| gender[b] | −0.97 | [−1.8; −0.31] | | | | |
| cone a-Wave implicit time (int1) | −0.52 | [−0.93; −0.17] | | | | |
| Model 2c | | | | | | |
| intercept | 1.35 | [−1.01; 3.79] | 0.11 | 0.71 | 73% | 57% |
| gender[b] | −0.54 | [−1.26; 0.11] | | | | |
| cone b-Wave amplitude (3-int) | −0.02 | [−0.05; 0.01] | | | | |
| Model 2d | | | | | | |
| intercept | −37.17 | [−57.83; −21.06] | 0.36 | 0.85 | 76% | 78% |
| gender[b] | −0.29 | [−1.09; 0.44] | | | | |
| cone b-Wave implicit time (3-int) | 1.16 | [0.65; 1.82] | | | | |
| Model 2e | | | | | | |
| intercept | 0.76 | [−0.61; 2.19] | 0.13 | 0.72 | 70% | 51% |
| gender[b] | −0.55 | [−1.26; 0.08] | | | | |
| rod a-Wave amplitude(Vmax) | −0.05 | [−0.11; 0] | | | | |
| Model 2f | | | | | | |
| intercept | 6.07 | [1.19; 12.13] | 0.17 | 0.73 | 70% | 51% |
| gender[b] | −0.78 | [−1.48; −0.17] | | | | |
| rod a-Wave implicit time (Vmax) | −0.22 | [−0.42; −0.06] | | | | |
| Model 2g | | | | | | |
| intercept | 1.82 | [−0.31; 4.15] | 0.14 | 0.72 | 70% | 57% |
| gender[b] | −0.63 | [−1.32; −0.02] | | | | |
| rod b-Wave amplitude (Vmax) | −0.01 | [−0.03; 0] | | | | |
| Model 2h | | | | | | |
| intercept | −4.71 | [−11.06; 0.77] | 0.11 | 0.68 | 73% | 46% |
| gender[b] | −0.61 | [−1.31; 0.01] | | | | |
| rod b-Wave implicit time (int2) | 0.09 | [−0.02; 0.23] | | | | |
| Model based on 2 ERG parameters (Model 3)[c] | | | | | | |
| intercept | −34.88 | [−58.3; −16.64] | 0.45 | 0.89 | 81% | 86% |
| gender[b] | −0.37 | [−1.27; 0.43] | | | | |
| rod a-Wave implicit time (Vmax) | −0.40 | [−0.75; −0.14] | | | | |
| cone b-Wave implicit time (3-int) | 1.47 | [0.83; 2.33] | | | | |
| Model based on 3 ERG parameters (Model 4)[c] | | | | | | |
| intercept | −24.84 | [−51.38; −3.88] | 0.54 | 0.94 | 84% | 89% |
| gender[b] | −0.03 | [−1.03; 0.94] | | | | |
| rod a-Wave implicit time (int2) | −1.67 | [−2.83; −0.84] | | | | |
| rod b-Wave amplitude (int2) | −0.03 | [−0.06; −0.01] | | | | |
| cone b-Wave implicit time (3-int) | 2.24 | [1.3; 3.66] | | | | |
| Model based on 4 ERG parameters (Model 5)[c] | | | | | | |
| intercept | −25.53 | [−53.57; −3.68] | 0.58 | 0.97 | 86% | 95% |
| gender[b] | −0.67 | [−2.23; 0.58] | | | | |
| cone a-wave implicit time (int1) | −0.67 | [−1.32; −0.16] | | | | |
| rod a-Wave implicit time (int2) | −1.52 | [−2.72; −0.66] | | | | |
| rod b-Wave amplitude (Vmax) | −0.04 | [−0.07; −0.01] | | | | |
| cone b-Wave implicit time (3-int) | 2.46 | [1.37; 4.11] | | | | |

Note that only gender is included as covariate in models, since the controls are matched for age to SZ with five years or less of disease.

[a]In the photopic ERG, the peak maximal response correspond to the « Vmax », « int1 » correspond to a fixed intensity of 7.5 cd × s/m$^2$ and « 3-int » correspond to an average of three intensities. For the rod function (scotopic ERG), « Vmax » refer to the saturating amplitude observed at the first plateau, where rods only are involved in the response (flash intensity of 0.1 cd × s/m$^2$) and « int2 » refer to a flash intensity of 1 cd × s/m$^2$.
[b]Female = 1 and male = 0
[c]When more than one model based on the same number of ERG parameters was possible, only the model that provided the higher accuracy according to the AUC is presented.
*This ERG parameter showed significant differences between SZ and CT, and SZ and BP in Balogh et al. (2008)

TABLE 14B

Prediction of SZ with 5 years or less of disease duration vs. matched controls

| As predicted | Group sample | | |
|---|---|---|---|
| by the ERGs | SZ | CT | |
| SZ | 35 (95%) | 3 (8%) | |
| CT | 2 (5%) | 34 (92%) | |
| Total | 37 | 37 | OR = 198 |

Incidentally, focusing on this subsample of patients with shorter durations of illness improved the model for the prediction of SZ with an AUC of 0.99, a sensitivity of 95%, a specificity of 92% and an OR of 198.

The univariate comparisons of the 37 SZ and 35 BP patients with a disease evolution of 5 or less years, on each of the eight ERG parameters are depicted in Table 15. The cone a-wave amplitude and the rod a-wave amplitude significantly distinguish SZ patients with five years or less of disease evolution from CT with p-value below 0.0063 and 0.01 respectively (ES=0.95, p=0.0002 and ES=0.65, p=0.0071 respectively).

TABLE 15

Comparison of ERG parameters in the 37 SZ and 35 BP patients with 5 years or less of disease duration.

| ERG parameters | Flash intensity[a] | Mean (SD) 37 SZ | Mean (SD) 35 BP | Effect size | P-value |
|---|---|---|---|---|---|
| Cones | | | | | |
| a-Wave amplitude* | int1 | 11.58 (5.4) | 16.78 (4.6) | 0.95 | 0.0002 |
| a-Wave implicit time | int1 | 14.5 (1.8) | 15.42 (1.5) | 0.52 | 0.0315 |
| b-Wave amplitude | 3-int | 71.38 (23.6) | 82.66 (19.9) | 0.47 | 0.0494 |
| b-Wave implicit time | 3-int | 28.81 (1.5) | 28.28 (1.3) | −0.35 | 0.1464 |
| Rods | | | | | |
| a-Wave amplitude | int2 | 53.21 (31.8) | 74.31 (26.9) | 0.65 | 0.0071 |
| a-Wave implicit time | Vmax | 23.94 (2) | 23.62 (1.7) | −0.16 | 0.4964 |
| b-Wave amplitude | Vmax | 133.41 (45.3) | 153.6 (38.3) | 0.44 | 0.0666 |
| b-Wave implicit time | int2 | 75.16 (14.9) | 67.09 (12.6) | −0.54 | 0.0263 |

Note that age and gender are included in all models as covariate

[a]In the photopic ERG, the peak maximal response correspond to the « Vmax », « int1 » correspond to a fixed intensity of 7.5 cd × s/m$^2$ and « 3-int » correspond to an average of three intensities. For the rod function (scotopic ERG), « Vmax » refer to the saturating amplitude observed at the first plateau, where rods only are involved in the response (flash intensity of 0.1 cd × s/m$^2$) and « int2 » refer to a flash intensity of 1 cd × s/m$^2$.
*This ERG parameter showed significant differences between SZ and CT, and SZ and BP in Balogh et al. (2008)

The prediction modeling (using multiple logistic regression) identified a model based on two ERG parameters that best predict if a subject is SZ vs. BP with an overall accuracy of 0.94, a sensitivity of 95%, a specificity of 80% (see model 1 in Table 16A) and a corresponding OR of 70 (see Table 16B). Table 16A also shows that other models including fewer ERG parameters can possibly predict SZ vs. BP subjects, but with lesser accuracy.

TABLE 16A

Parameter estimates of the multiple logistic regression to predict SZ vs. BP with 5 or less years of disease duration.

| Parameter(flash intensity[a]) | Parameter estimate Value | 95% CI | $R^2$ | AUC | Sensitivity | Specificity |
|---|---|---|---|---|---|---|
| SZ vs. BP with 5 years or less of disease duration | | | | | | |
| Best model of the multiple logistic regression (model 1) | | | | | | |
| intercept | 5.31 | [0.67; 10.51] | 0.52 | 0.94 (FIG. 11) | 95% | 80% |
| age | −0.20 | [−0.36; −0.09] | | | | |
| gender[b] | −1.37 | [−2.35; −0.56] | | | | |
| cone a-Wave amplitude (int1) | −0.36 | [−0.62; −0.16] | | | | |
| rod b-Wave implicit time (Vmax) | 0.08 | [0.01; 0.15] | | | | |
| Models of the simple logistic regression | | | | | | |
| Model 2a | | | | | | |
| intercept | 7.61 | [3.88; 12.27] | 0.48 | 0.91 | 89% | 89% |
| age | −0.13 | [−0.22; −0.05] | | | | |
| gender[b] | −1.39 | [−2.26; −0.65] | | | | |
| cone a-Wave amplitude (int1)* | −0.30 | [−0.5; −0.13] | | | | |

TABLE 16A-continued

Parameter estimates of the multiple logistic regression to predict SZ vs. BP with 5 or less years of disease duration.

| Parameter(flash intensity[a]) | Parameter estimate Value | 95% CI | $R^2$ | AUC | Sensitivity | Specificity |
|---|---|---|---|---|---|---|
| Model 2b | | | | | | |
| intercept | 9.91 | [3.03; 18.32] | 0.41 | 0.86 | 89% | 80% |
| age | −0.08 | [−0.16; −0.01] | | | | |
| gender[b] | −1.82 | [−2.74; −1.1] | | | | |
| cone a-Wave implicit time (int1) | −0.52 | [−1.06; −0.06] | | | | |
| Model 2c | | | | | | |
| intercept | 6.73 | [2.26; 12.14] | 0.41 | 0.88 | 89% | 80% |
| age | −0.14 | [−0.24; −0.06] | | | | |
| gender[b] | −1.32 | [−2.11; −0.64] | | | | |
| cone b-Wave amplitude (int1) | −0.04 | [−0.08; 0] | | | | |
| Model 2d | | | | | | |
| intercept | −8.59 | [−23.33; 5.32] | 0.39 | 0.86 | 84% | 83% |
| age | −0.12 | [−0.21; −0.05] | | | | |
| gender[b] | −1.42 | [−2.19; −0.76] | | | | |
| cone b-Wave implicit time (int1) | 0.42 | [−0.09; 0.97] | | | | |
| Model 2e | | | | | | |
| intercept | 7.20 | [3.09; 12.51] | 0.44 | 0.89 | 86% | 80% |
| age | −0.16 | [−0.28; −0.07] | | | | |
| gender[b] | −1.61 | [−2.46; −0.91] | | | | |
| rod a-Wave amplitude (int2) | −0.04 | [−0.08; −0.01] | | | | |
| Model 2f | | | | | | |
| intercept | −0.51 | [−9.38; 8.16] | 0.37 | 0.85 | 84% | 80% |
| age | −0.10 | [−0.19; −0.03] | | | | |
| gender[b] | −1.50 | [−2.27; −0.85] | | | | |
| rod a-Wave implicit time (int2) | 0.14 | [−0.23; 0.54] | | | | |
| Model 2g | | | | | | |
| intercept | 6.20 | [2.22; 10.88] | 0.41 | 0.88 | 89% | 83% |
| age | −0.13 | [−0.22; −0.05] | | | | |
| gender[b] | −1.64 | [−2.5; −0.95] | | | | |
| rod b-Wave amplitude (Vmax) | −0.02 | [−0.04; 0] | | | | |
| Model 2h | | | | | | |
| intercept | −0.30 | [−3.9; 3.24] | 0.41 | 0.87 | 84% | 80% |
| age | −0.13 | [−0.23; −0.05] | | | | |
| gender[b] | −1.54 | [−2.33; −0.88] | | | | |
| rod b-Wave implicit time (Vmax) | 0.06 | [0.01; 0.12] | | | | |

Note that age and gender are included as covariates in models.
[a]In the photopic ERG, the peak maximal response correspond to the « Vmax », « int1 » correspond to a fixed intensity of 7.5 cd × s/m² and « 3-int » correspond to an average of three intensities. For the rod function (scotopic ERG), « Vmax » refer to the saturating amplitude observed at the first plateau, where rods only are involved in the response (flash intensity of 0.1 cd × s/m²) and « int2 » refer to a flash intensity of 1 cd × s/m².
[b]Female = 1 and male = 0
*This ERG parameter showed significant differences between SZ and CT, and SZ and BP in Balogh et al. (2008)

Figure 11:
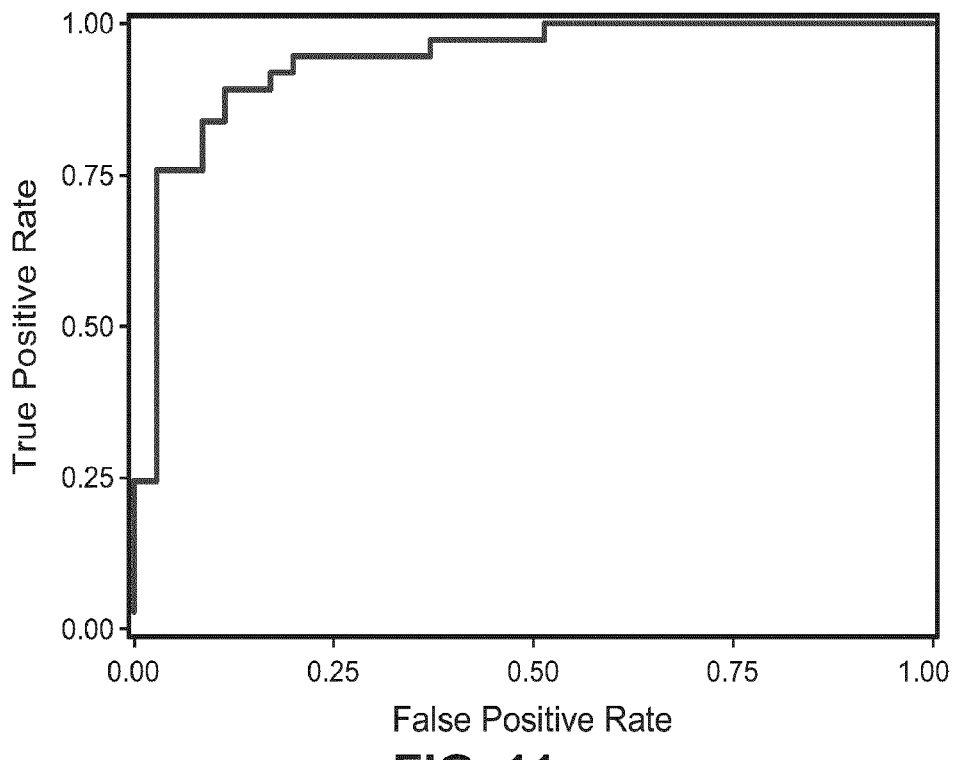
FIG. 11 is the ROC curve of the model predicting SZ vs. BP subjects with 5 years or less of disease duration based on 2 ERG parameters (see Table 16A), with an AUC of 94% corresponding to a sensitivity of 95% and a specificity of 80%.

The model for differential diagnosis was greatly improved by this approach with an AUC of 0.94, a sensitivity of 95%, a specificity of 80%, corresponding to an OR of 70 (see Table 16B and ROC curve in FIG. 11).

TABLE 16B

Prediction of SZ vs. BP with 5 years or less of disease duration

| As predicted by the ERGs | Group sample | |
|---|---|---|
| | SZ | BP |
| SZ | 35 (95%) | 7 (20%) |
| BP | 2 (5%) | 28 (80%) |
| Total | 37 | 35 | OR = 70 |

The above results shows that the diagnosis of SZ and BP may be improved by focusing the analysis on subjects having shorter durations of illness (≤5 years), which is the period of illness when the mental health practitioner needs the most aid to determine the suitable treatment of the patient.

Example 8: ERG Profile and Response to Lithium in BP Patients

Table 17 shows a univariate analysis on each ERG parameter comparing good vs. poor responders to lithium medication. For BP subjects taking lithium, the stronger difference between the good and the poor responders in univariate analysis was observed for the rod a-wave implicit time (ES=−0.78, p-value=0.08; see Table 17). These univariate results show that prediction modeling based on multiple logistic regression may detect a subset of ERG parameters that best predict the group membership, as detailed below.

TABLE 17

Comparison of ERG parameters in good vs. poor BP responders to lithium

| ERG parameters | Flash intensity[a] | Mean (SD) Good responders (N = 38) | Mean (SD) Poor responders (N = 6) | Effect size | P-value |
|---|---|---|---|---|---|
| Cones | | | | | |
| a-Wave amplitude | 3-int | 23.39 (5.3) | 20.53 (5.2) | −0.54 | 0.2255 |
| a-Wave implicit time | int1 | 16.08 (1.1) | 15.46 (1.1) | −0.58 | 0.1936 |
| b-Wave amplitude | 3-int | 82.24 (17.2) | 82.4 (16.8) | 0.01 | 0.9826 |
| b-Wave implicit time | Vmax | 32.62 (2.4) | 33.6 (2.4) | 0.40 | 0.3648 |
| Rods | | | | | |
| a-Wave amplitude | int2 | 51.33 (25.4) | 56.65 (24.9) | 0.21 | 0.6357 |
| a-Wave implicit time | int2 | 24.29 (1.8) | 22.91 (1.7) | −0.78 | 0.0845 |
| b-Wave amplitude | Vmax | 146.59 (31.7) | 133.15 (31) | −0.43 | 0.3381 |
| b-Wave implicit time | int2 | 49.04 (4.5) | 47.73 (4.4) | −0.29 | 0.5102 |

Note that age and gender are included in all models as covariate

[a] In the photopic ERG, the peak maximal response correspond to the « Vmax », « int1 » correspond to a fixed intensity of 7.5 cd × s/m² and « 3-int » correspond to an average of three intensities. For the rod function (scotopic ERG), « Vmax » refer to the saturating amplitude observed at the first plateau, where rods only are involved in the response (flash intensity of 0.1 cd × s/m²) and « int2 » refer to a flash intensity of 1 cd × s/m².

The prediction modeling (using multiple logistic regression) identified a model based on five ERG parameters that best predict if a subject is a good or poor responder to lithium with an overall accuracy of 0.97, a sensitivity of 97%, a specificity of 50% (see model 10 in Table 18A) and a corresponding OR of 37 (see Table 18B). Table 18A also shows that other models including fewer ERG parameters can possibly predict good versus poor lithium responders, but with lesser accuracy.

TABLE 18A

Parameter estimates of the multiple logistic regression to predict good vs. poor response to lithium in BP patients

Figure 3F:
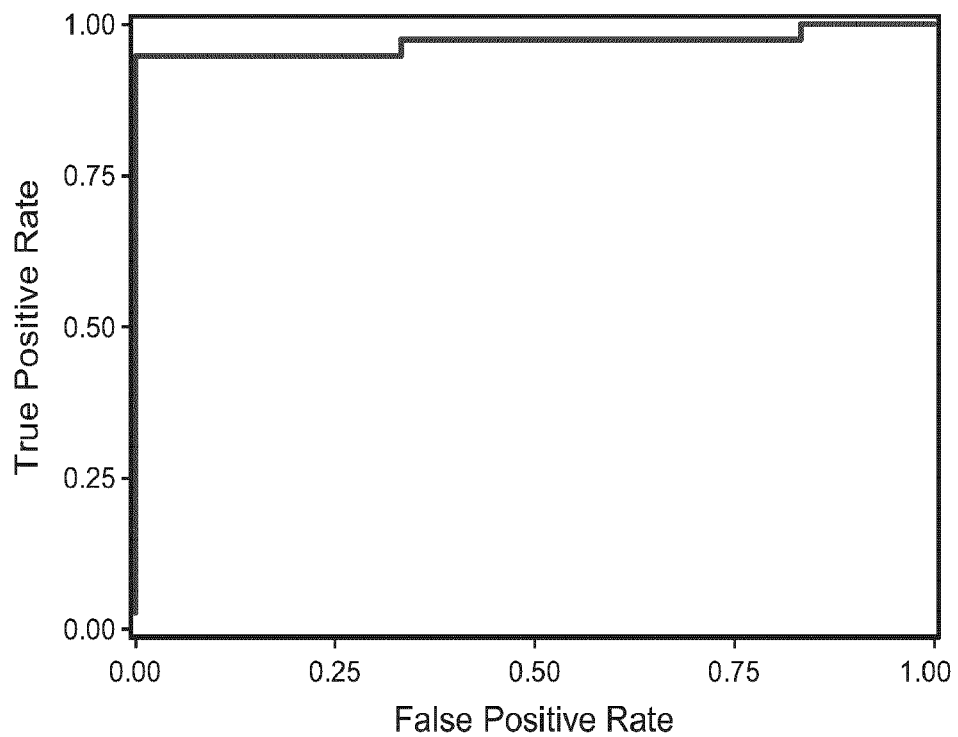
FIG. 3F is the ROC curve of the model predicting good relative to poor responders BP subjects taking lithium (without clozapine) based on five ERG parameters (see Table 18A), with an AUC of 97% corresponding to a sensitivity of 97% and a specificity of 50%.

| Good Vs Poor response Parameter (flash intensity[a]) | Parameter estimate Value | Parameter estimate 95% CI | $R^2$ | AUC | Sensitivity | Specificity |
|---|---|---|---|---|---|---|
| BP taking lithium without clozapine | | | | | | |
| Best model of the multiple logistic regression (model 10) | | | 0.34 | 0.97 (FIG. 3F) | 97% | 50% |
| intercept | −61.12 | [−277; 1787] | | | | |
| age | 0.10 | [−18.6; 3.00] | | | | |
| gender[b] | 3.12 | [−101.2; 16.3] | | | | |
| cone a-Wave amplitude (Vmax) | 0.16 | [−87.2; 13.85] | | | | |
| cone a-Wave implicit time (int1) | 1.05 | [−4.28; 25.15] | | | | |
| cone b-Wave implicit time (Vmax) | −2.49 | [−87.2; 13.85] | | | | |
| cone b-Wave implicit time (3-int) | 0.77 | [−87.2; 13.85] | | | | |
| rod a-Wave implicit time (int2) | 3.17 | [−4.07; 23.10] | | | | |
| Models of the simple logistic regression | | | | | | |
| Model 11a | | | | | | |
| intercept | −4.04 | [−11.74; 3.08] | 0.10 | 0.80 | 100% | 0% |
| age | 0.08 | [−0.04; 0.22] | | | | |
| gender[b] | 0.88 | [−0.11; 2.14] | | | | |
| cone a-Wave amplitude (3-int) | 0.11 | [−0.06; 0.31] | | | | |
| Model 11b | | | | | | |
| intercept | −6.97 | [−20.25; 4.87] | 0.09 | 0.73 | 17% | 100% |
| age | 0.04 | [−0.08; 0.17] | | | | |
| gender[b] | 0.91 | [−0.07; 2.12] | | | | |
| cone a-Wave implicit time (int1) | 0.45 | [−0.32; 1.35] | | | | |
| Model 11c | | | | | | |
| intercept | −0.52 | [−8.08; 7.11] | 0.07 | 0.70 | 100% | 0% |
| age | 0.06 | [−0.05; 0.18] | | | | |
| gender[b] | 0.82 | [−0.24; 2.09] | | | | |
| cone b-Wave amplitude (3-int) | 0.00 | [−0.06; 0.06] | | | | |

TABLE 18A-continued

Parameter estimates of the multiple logistic regression to predict good vs. poor response to lithium in BP patients

| Good Vs Poor response | Parameter estimate | | | | | |
|---|---|---|---|---|---|---|
| Parameter (flash intensity[a]) | Value | 95% CI | $R^2$ | AUC | Sensitivity | Specificity |
| Model 11d | | | | | | |
| intercept | 6.09 | [−7.43; 19.45] | 0.09 | 0.77 | 100% | 0% |
| age | 0.08 | [−0.04; 0.22] | | | | |
| gender[b] | 0.71 | [−0.3; 1.94] | | | | |
| cone b-Wave implicit time (Vmax) | −0.23 | [−0.69; 0.2] | | | | |
| Model 11e | | | | | | |
| intercept | −2.42 | [−9.63; 4.12] | 0.08 | 0.72 | 100% | 0% |
| age | 0.08 | [−0.04; 0.24] | | | | |
| gender[b] | 0.90 | [−0.11; 2.23] | | | | |
| rod a-Wave amplitude (Vmax) | 0.04 | [−0.06; 0.17] | | | | |
| Model 11f | | | | | | |
| intercept | −8.09 | [−18.95; 1.79] | 0.12 | 0.80 | 17% | 100% |
| age | −0.01 | [−0.16; 0.14] | | | | |
| gender[b] | 1.04 | [0; 2.45] | | | | |
| rod a-Wave implicit time (int2) | 0.44 | [−0.07; 1.04] | | | | |
| Model 11g | | | | | | |
| intercept | −2.64 | [−9.17; 3.65] | 0.09 | 0.75 | 0% | 97% |
| age | 0.06 | [−0.05; 0.18] | | | | |
| gender[b] | 0.68 | [−0.33; 1.92] | | | | |
| rod b-Wave amplitude (Vmax) | 0.02 | [−0.01; 0.05] | | | | |
| Model 11h | | | | | | |
| intercept | −1.22 | [−7.21; 4.5] | 0.07 | 0.75 | 100% | 0% |
| age | 0.05 | [−0.07; 0.18] | | | | |
| gender[b] | 0.81 | [−0.15; 2] | | | | |
| rod b-Wave implicit time (Vmax) | 0.01 | [−0.06; 0.1] | | | | |
| Model based on 2 ERG parameters[c](Model 12) | | | | | | |
| intercept | −2.83 | [−10.05; 3.41] | 0.21 | 0.86 | 97% | 50% |
| age | 0.02 | [−0.1; 0.15] | | | | |
| gender | 0.34 | [−0.79; 1.61] | | | | |
| rod b-Wave amplitude (Vmax) | 0.13 | [0.03; 0.27] | | | | |
| rod b-Wave amplitude (int2) | −0.08 | [−0.19; −0.02] | | | | |
| Model based on 3 ERG parameters[c](Model 13) | | | | | | |
| intercept | −4.93 | [−14.18; 2.24] | 0.24 | 0.89 | 97% | 50% |
| age | −0.01 | [−0.16; 0.13] | | | | |
| gender | 0.55 | [−0.64; 1.97] | | | | |
| rod b-Wave amplitude (Vmax) | 0.14 | [0.04; 0.28] | | | | |
| rod b-Wave amplitude (int2) | −0.09 | [−0.2; −0.02] | | | | |
| rod b-Wave implicit time (Vmax) | 0.15 | [−0.11; 0.43] | | | | |
| Model based on 4 ERG parameters[c](Model 14) | | | | | | |
| intercept | −38.28 | [−105.3; −2.7] | 0.29 | 0.93 | 97% | 33% |
| age | 0.06 | [−0.13; 0.33] | | | | |
| gender | 2.24 | [0.35; 6.16] | | | | |
| cone a-wave amplitude (Vmax) | 0.16 | [−0.01; 0.43] | | | | |
| cone b-Wave implicit time (Vmax) | −1.58 | [−4.29; −0.32] | | | | |
| rod a-Wave implicit time (int2) | 0.70 | [0.11; 1.56] | | | | |
| cone b-Wave implicit time (3-int) | 2.14 | [0.26; 5.96] | | | | |

Note that age and gender are included in models as covariate

[a]In the photopic ERG, the peak maximal response correspond to the «Vmax», «int1» correspond to a fixed intensity of 7.5 cd × s/m$^2$ and «3-int» correspond to an average of three intensities. For the rod function (scotopic ERG), «Vmax» refer to the saturating amplitude observed at the first plateau, where rods only are involved in the response (flash intensity of 0.1 cd × s/m$^2$) and «int2» refer to a flash intensity of 1 cd × s/m$^2$.

[b]Female = 1 and male = 0

[c]When more than one model based on the same number of ERG parameters was possible, only the model that provided the higher accuracy according to the AUC is presented.

TABLE 18B

Prediction of good response to lithium
in BP subjects not taking clozapine

| As predicted by the ERGs | Observed response to treatment | | |
|---|---|---|---|
| | Good | Poor | |
| Good response | 97% (37) | 50% (3) | |
| Poor response | 3% (1) | 50% (3) | |
| Total | 38 | 6 | OR = 37 |

Example 9: ERG Profile and Response to Quetiapine in SZ and BP Patients

Table 19 shows a univariate analysis on each ERG parameter comparing good vs. poor responders to quetiapine (without clozapine) in SZ and BP patients. For SZ and BP subjects taking quetiapine, two ERG parameters showed differences (p-values below 0.05) between the good and the poor responders (cone b-wave implicit time, ES=−0.73, p-value=0.04; rod a-wave implicit time, ES=−0.76, p-value=0.03; see Table 19). These univariate results show that prediction modeling based on multiple logistic regression may detect a subset of ERG parameters that best predict the group membership, as detailed below.

TABLE 19

Comparison of ERG parameters in good vs. poor SZ and
BP responders to quetiapine (without clozapine)

| | | Mean (SD) | | | |
|---|---|---|---|---|---|
| ERG parameters | Flash intensity[a] | Good responders (N = 30) | Poor responders (N = 12) | Effect size | P-value |
| Cones | | | | | |
| a-Wave amplitude | 3-int | 20.49 (5.9) | 24.12 (5.8) | 0.62 | 0.0782 |
| a-Wave implicit time | 3-int | 14.58 (1.1) | 14.02 (1) | −0.53 | 0.1309 |
| b-Wave amplitude | int1 | 66.12 (19.3) | 73.21 (18.9) | 0.37 | 0.2874 |
| b-Wave implicit time | int1 | 29.4 (1.1) | 28.61 (1.1) | −0.73 | 0.0389 |
| Rods | | | | | |
| a-Wave amplitude | int2 | 54.21 (18.5) | 60.94 (18.1) | 0.36 | 0.2923 |
| a-Wave implicit time | int2 | 24.05 (1.2) | 23.17 (1.1) | −0.76 | 0.0316 |
| b-Wave amplitude | int2 | 170.85 (29.2) | 161.45 (28.6) | −0.32 | 0.3506 |
| b-Wave implicit time | int2 | 47.92 (5.1) | 49.19 (5) | 0.25 | 0.4663 |

Note that age and gender are included in all models as covariate

[a]In the photopic ERG, the peak maximal response correspond to the « Vmax », « int1 » correspond to a fixed intensity of 7.5 cd × s/m$^2$ and « 3-int » correspond to an average of three intensities. For the rod function (scotopic ERG), « Vmax » refer to the saturating amplitude observed at the first plateau, where rods only are involved in the response (flash intensity of 0.1 cd × s/m$^2$) and « int2 » refer to a flash intensity of 1 cd × s/m$^2$.

The prediction modeling (using multiple logistic regression) identified a model based on five ERG parameters that best predict if a BP or SZ subject is a good or poor responder to quetiapine with an overall accuracy of 0.97, a sensitivity of 97%, a specificity of 92% (see model 15 in Table 20A) and a corresponding OR of 319 (see Table 20B). Table 20A also shows that other models including fewer ERG parameters can possibly predict good versus poor SZ and/or BP quetiapine responders, but with lesser accuracy.

TABLE 20A

Parameter estimates of the multiple logistic regression to
predict good vs. poor response to quetiapine in SZ and BP patients

Figure 3G:
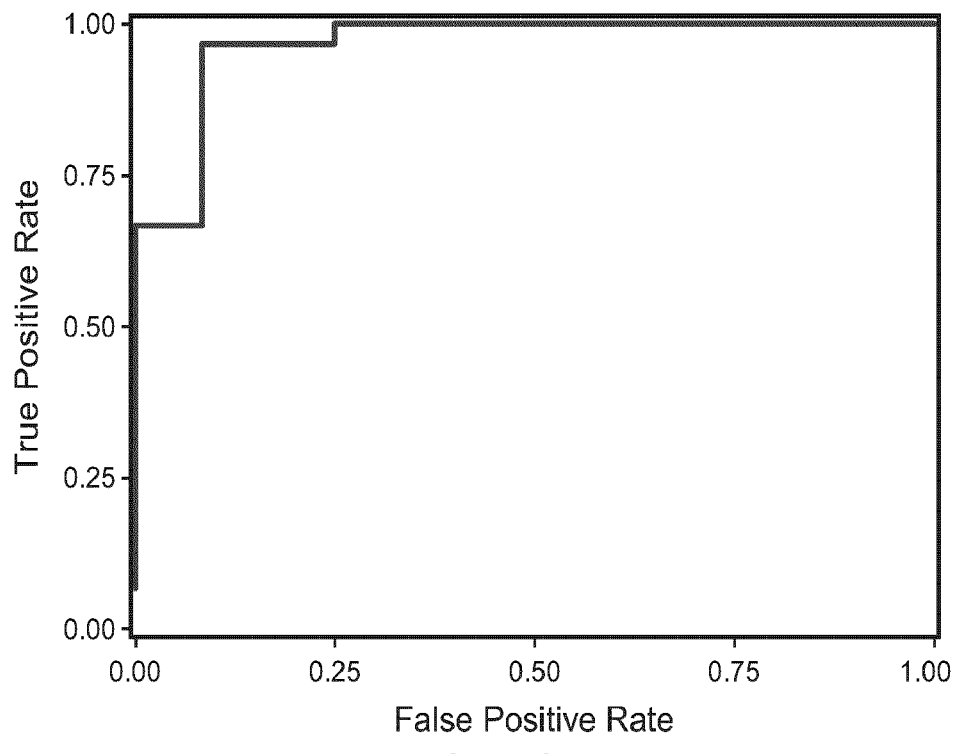
FIG. 3G is the ROC curve of the model predicting good relative to poor responders SZ and BP subjects taking quetiapine (without clozapine) based on five ERG parameters (see Table 20A), with an AUC of 97% corresponding to a sensitivity of 97% and a specificity of 92%.
Figure 4:
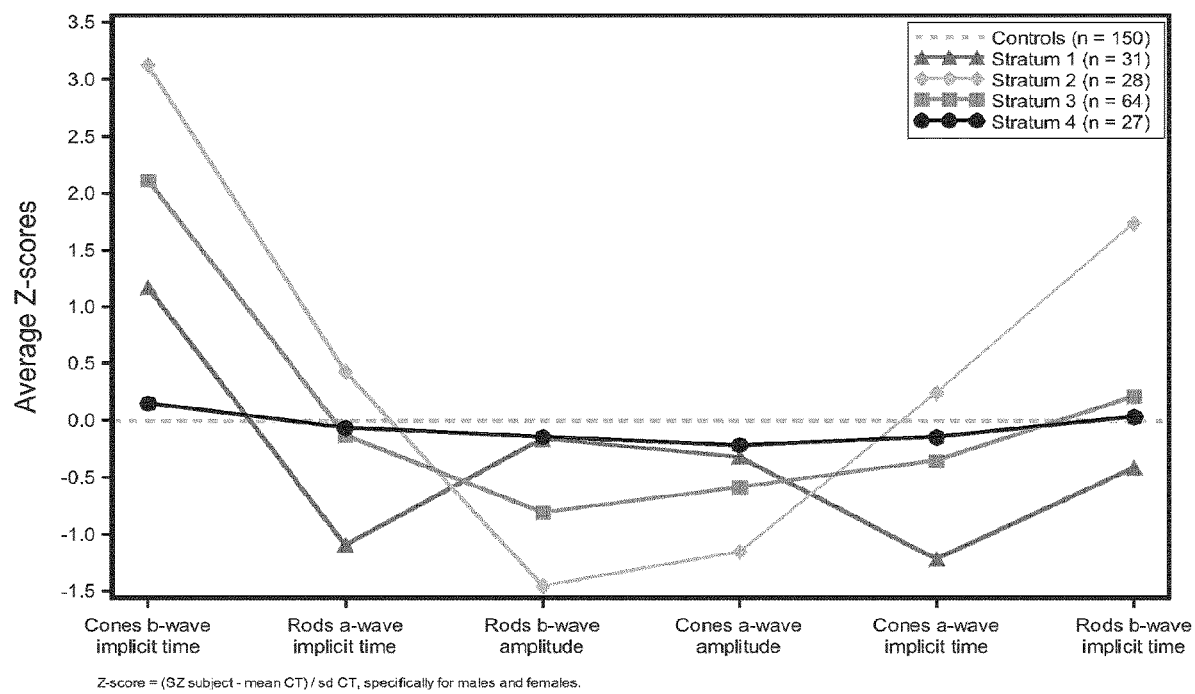
FIG. 4 shows that cluster analysis revealed four ERG strata for SZ subjects. Stratum 4 identifies the SZ subjects whose ERG profile most closely resembled those of control subjects; Stratum 1 identifies SZ subjects showing diminished implicit times on 2 ERG parameters (rod a-wave implicit time and cone a-wave implicit time); Stratum 2 shows anomalies on 4 ERG parameters (cone b-wave implicit time, rod b-wave amplitude, cone a-wave amplitude and rod b-wave implicit time), while stratum 3 is found in an in-between position.
Figure 5A:
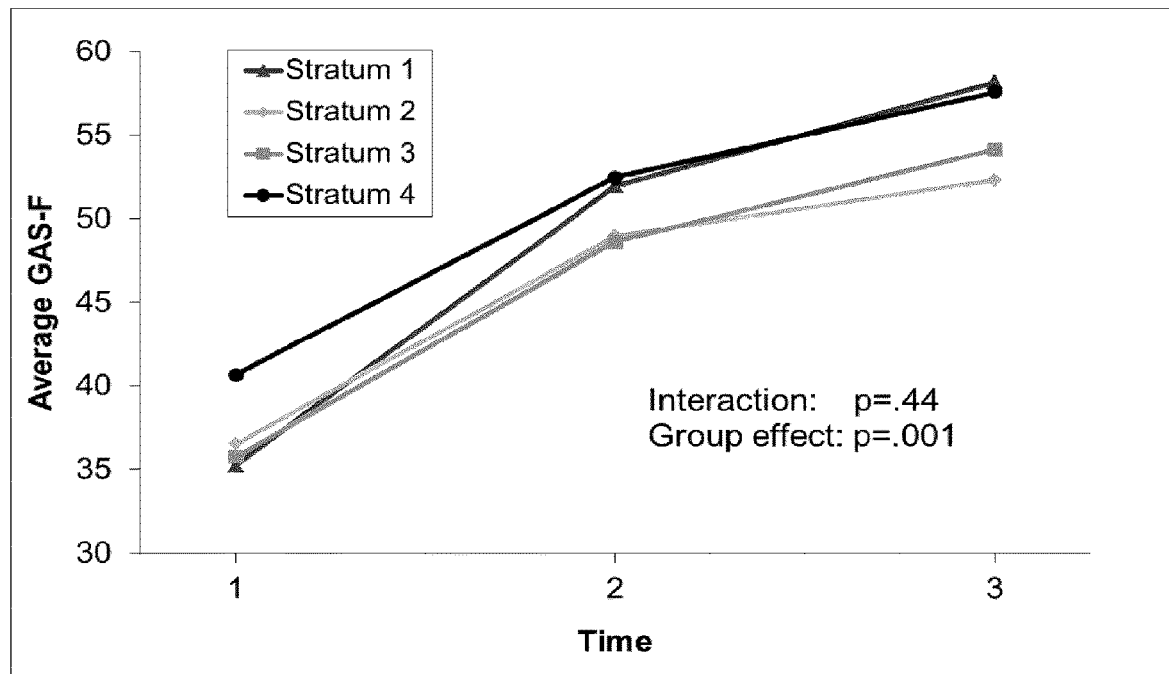
FIG. 5A shows the relationship between the patients' ERG strata and lifetime Global Assessment Scale-Functionality (GAS-F) trajectories for SZ subjects. Over time the best responders are observed in stratum 1, whereas the poorer responders are typically in strata 2 and 3. Note that SZ subjects in stratum 4 also responded well over time but they were those with higher GAS-F at time 1. Repeated measure analyses were performed with three different periods: —the time of first admission or first episode of illness (T1), —6 to 24 months after the last hospitalization or acute episode (T2)—the last 6 to 24 months with the same medication before the ERG recording (T3)
Figure 5B:
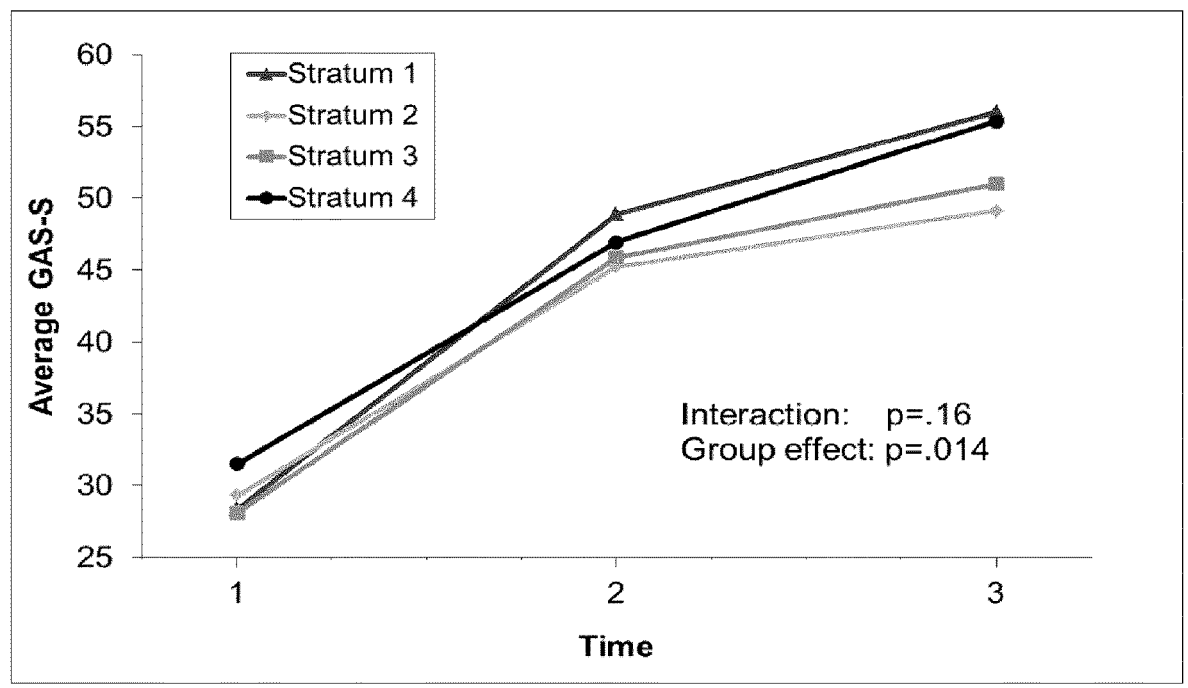
FIG. 5B shows the relationship between the SZ subjects' ERG strata and lifetime Global Assessment Scale-Severity (GAS-S) trajectories.
Figure 6:
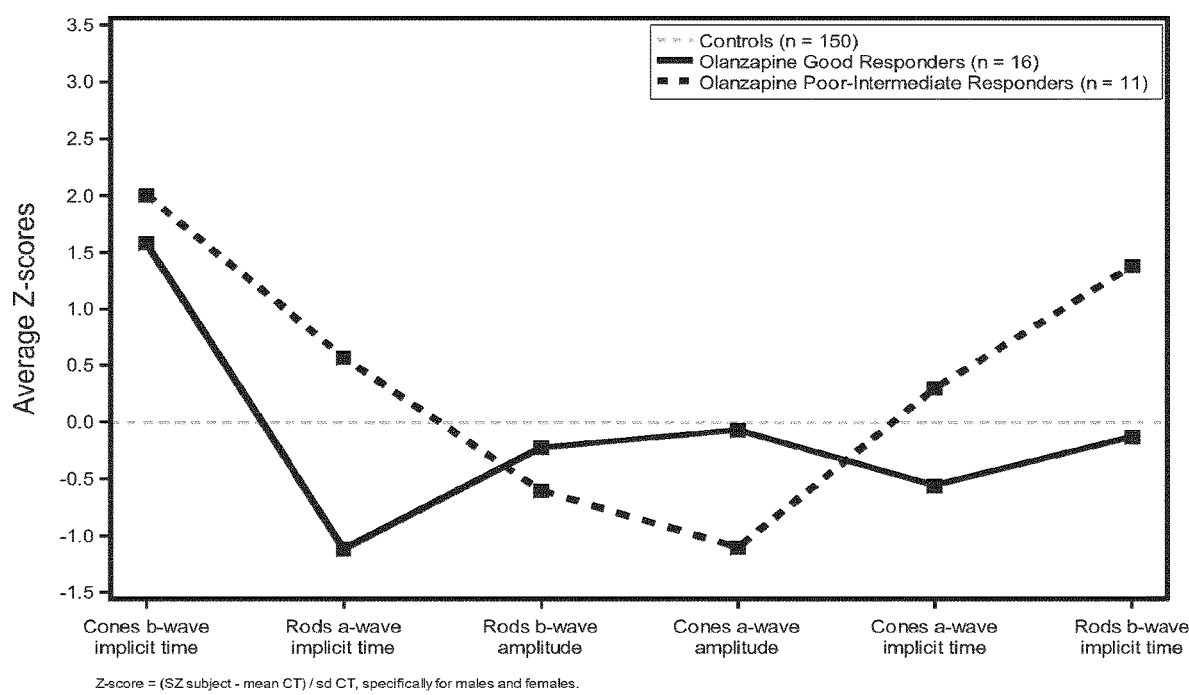
FIG. 6 shows, for SZ subjects, the differences in the ERG profiles between the poor-intermediate and the good responders to a specific medication, such as olanzapine. The good responders to olanzapine are represented by a solid black line, and the poor-intermediate responders are represented by a dashed black line.
Figure 7:
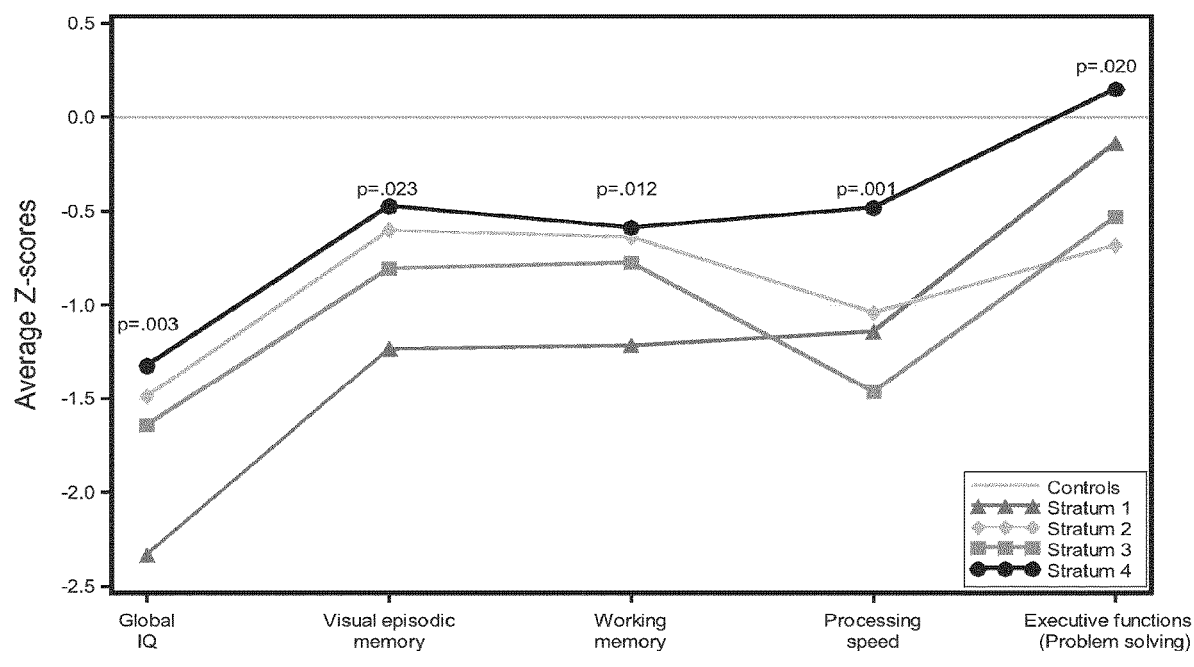
FIG. 7 shows the relationship between the 4 strata of SZ subjects and cognitive functioning. Analysis of covariance (ANCOVA) adjusted for age and gender were performed to compare the four strata of patients.
Figure 8A:
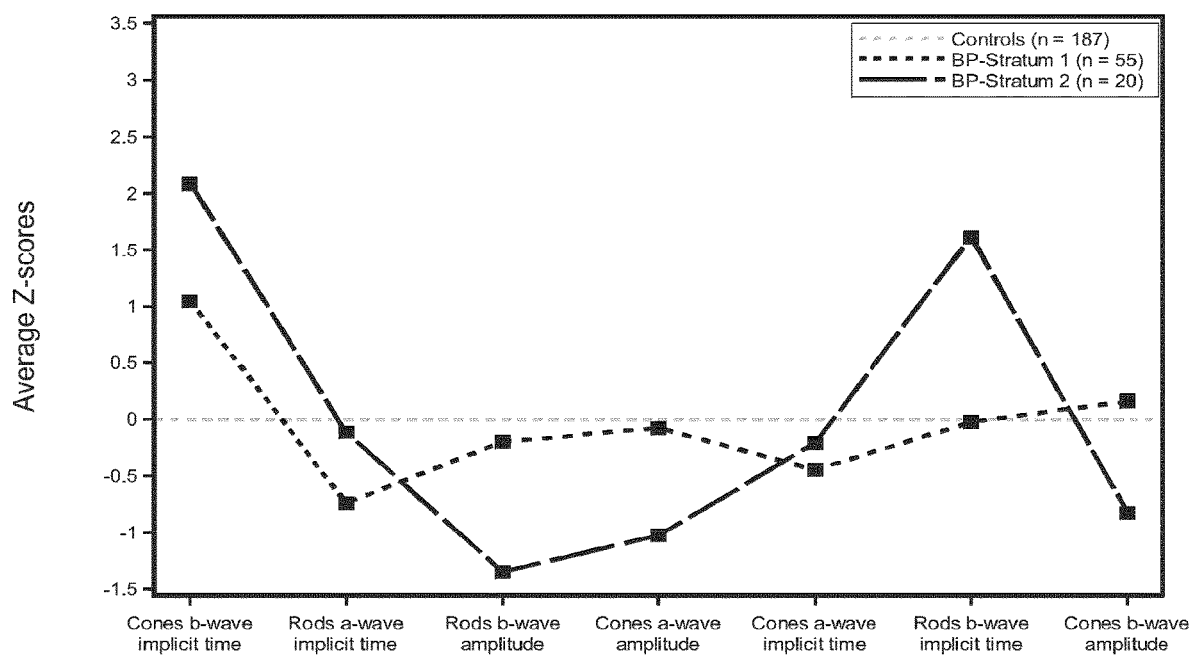
FIG. 8A shows that cluster analysis of the 75 bipolar disorder (BP) patients revealed 2 ERG BP strata.
Figure 8B:
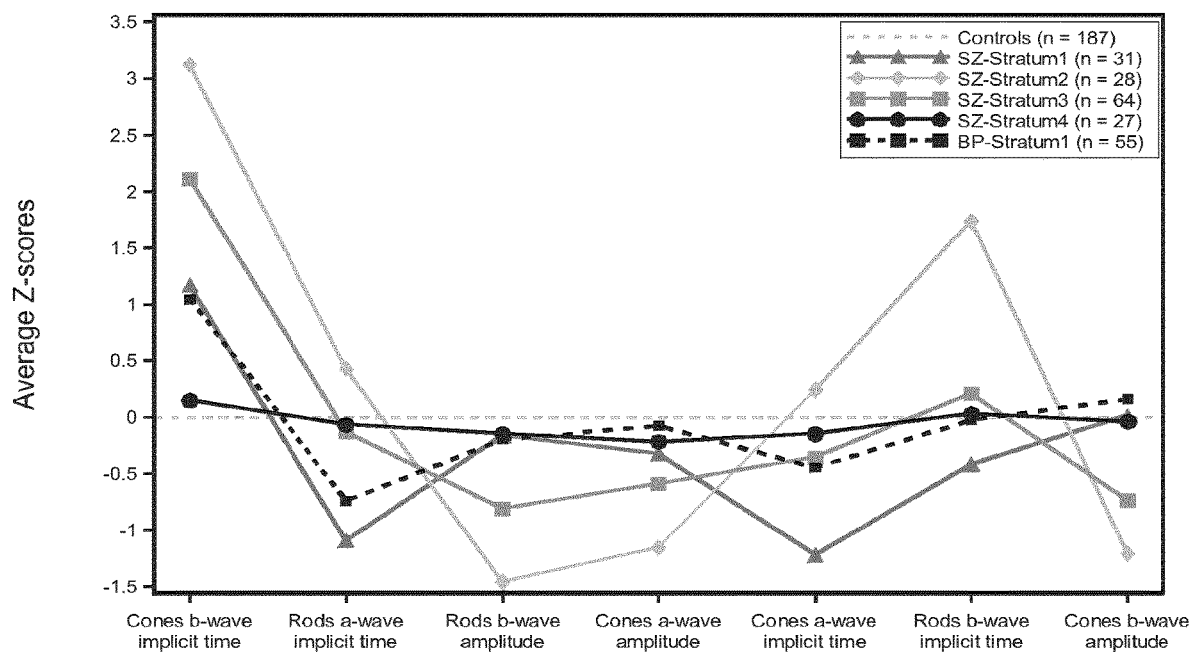
FIG. 8B shows a comparison of BP stratum 1 with the four SZ strata.
Figure 8C:
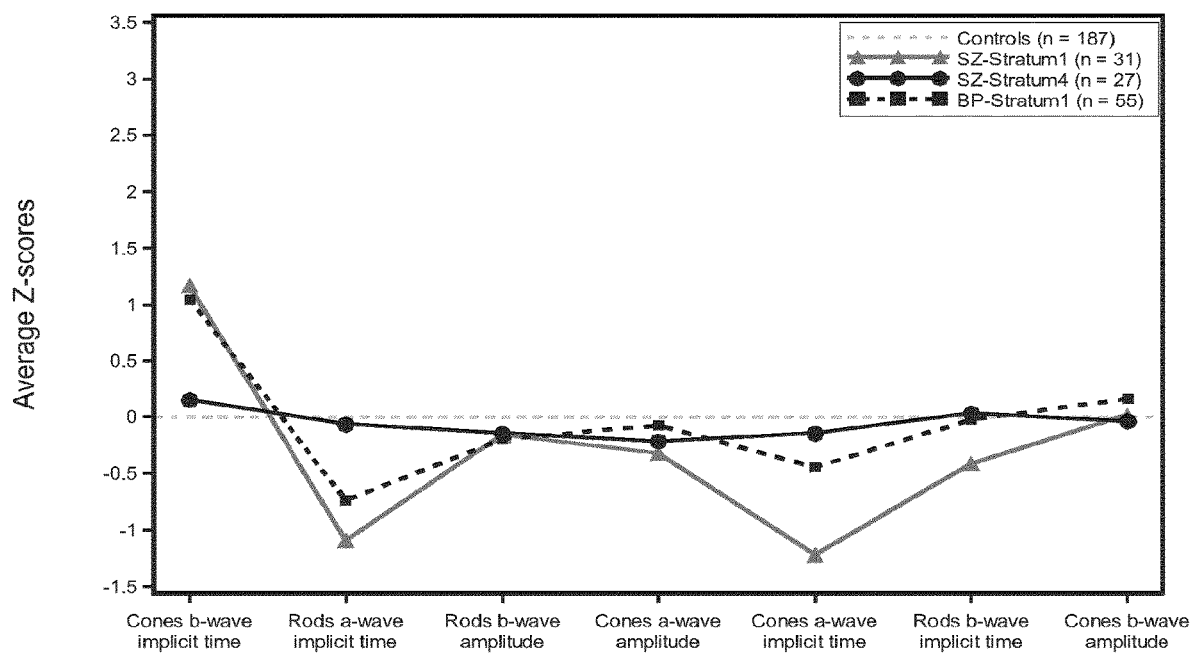
FIG. 8C shows a comparison of BP stratum 1 with the SZ strata 1 and 4.
Figure 8D:
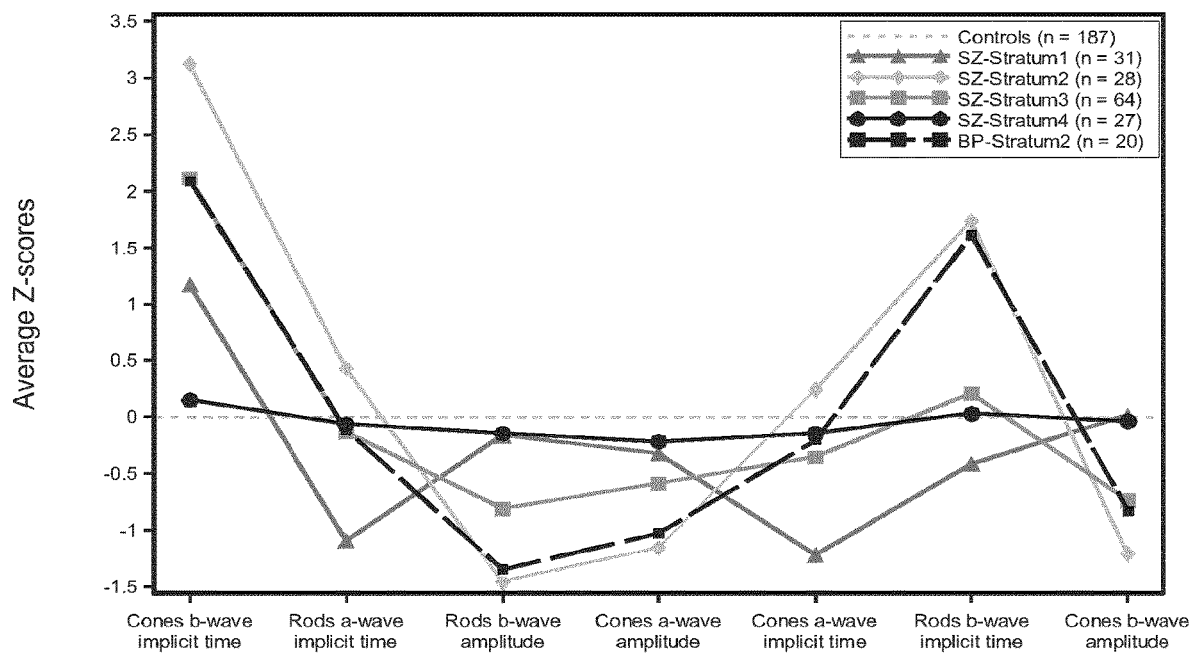
FIG. 8D shows a comparison of BP stratum 2 with the four SZ strata.
Figure 8E:
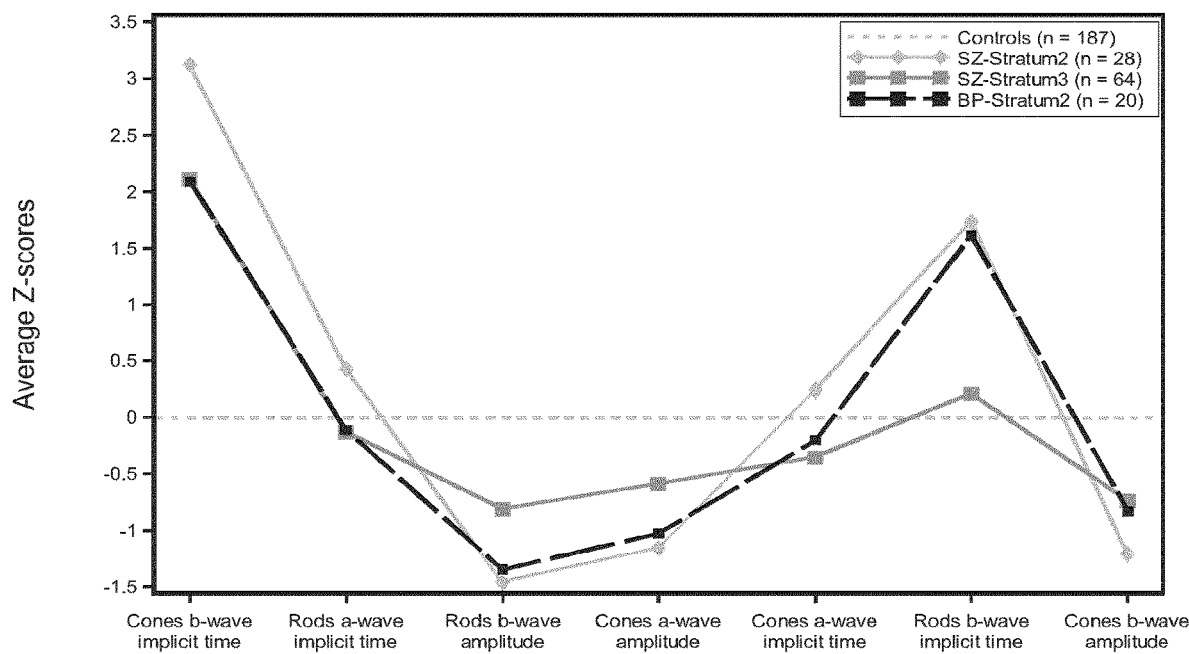
FIG. 8E shows a comparison of BP stratum 2 with the SZ strata 2 and 3.
Figure 9:
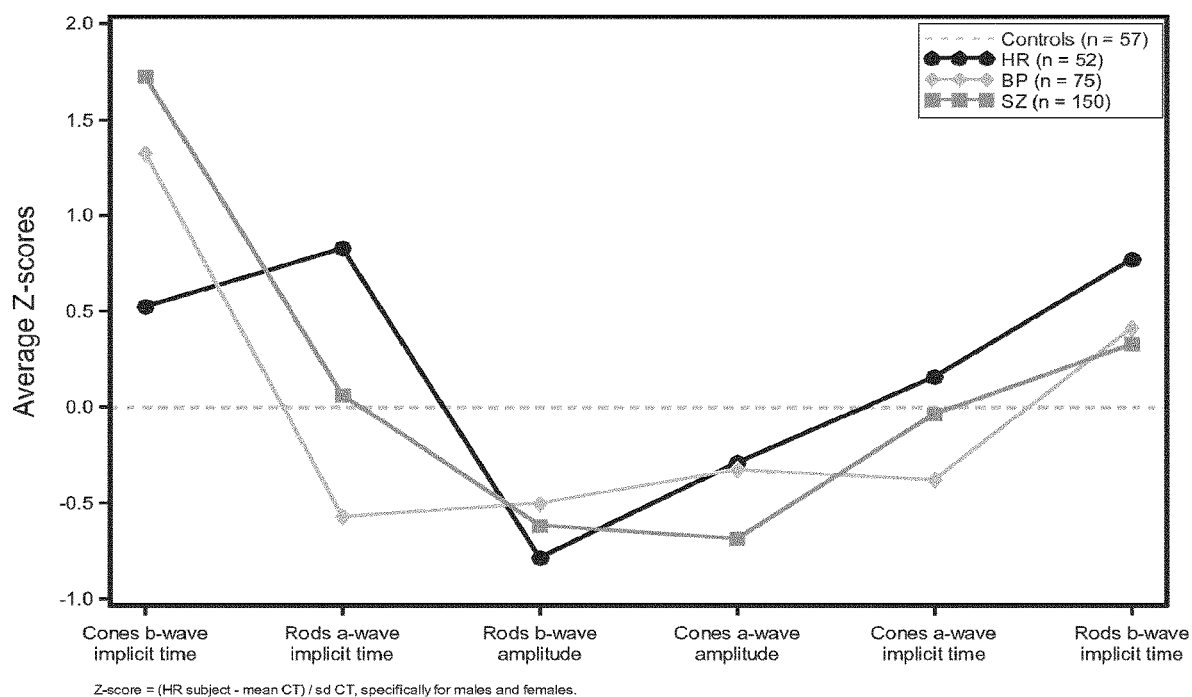
FIG. 9 shows a comparison of HRs of SZ/BP vs. control, SZ and BP subjects (see Table 11).

| Good Vs Poor response | Parameter estimate | | | | | |
|---|---|---|---|---|---|---|
| Parameter(flash intensity[a]) | Value | 95% CI | R$^2$ | AUC | Sensitivity | Specificity |
| SZ and BP taking quetiapine without clozapine | | | | | | |
| Best model of the multiple logistic regression (model 15) | | | 0.54 | 0.97 (FIG. 3G) | 97% | 92% |
| intercept | −69.38 | [−160.4; −16.3] | | | | |
| age | −0.44 | [−1.08; −0.15] | | | | |
| gender[b] | −2.73 | [−5.72; −0.84] | | | | |
| cone a-wave amplitude (Vmax) | 0.69 | [0.15; 1.79] | | | | |
| cone b-Wave amplitude (int1) | −0.31 | [−0.72; −0.11] | | | | |
| rod a-Wave implicit time (int2) | 4.61 | [1.71; 9.94] | | | | |
| rod b-Wave amplitude (Vmax) | 0.15 | [0.04; 0.38] | | | | |
| rod b-Wave implicit time (int2) | −0.66 | [−1.51; −0.24] | | | | |
| Models of the simple logistic regression | | | | | | |

TABLE 20A-continued

Parameter estimates of the multiple logistic regression to predict good vs. poor response to quetiapine in SZ and BP patients

| Good Vs Poor response | Parameter estimate | | | | | |
|---|---|---|---|---|---|---|
| Parameter(flash intensity[a]) | Value | 95% CI | $R^2$ | AUC | Sensitivity | Specificity |
| Model 16a | | | | | | |
| intercept | 4.48 | [0.28; 9.45] | 0.12 | 0.71 | 97% | 25% |
| age | −0.03 | [−0.11; 0.05] | | | | |
| gender[b] | −0.53 | [−1.3; 0.18] | | | | |
| cone a-Wave amplitude (3-int) | −0.11 | [−0.26; 0.01] | | | | |
| Model 16b | | | | | | |
| intercept | −5.39 | [−16.23; 4.46] | 0.10 | 0.70 | 90% | 17% |
| age | −0.04 | [−0.13; 0.04] | | | | |
| gender[b] | −0.40 | [−1.14; 0.31] | | | | |
| cone a-Wave implicit time (3-int) | 0.57 | [−0.13; 1.36] | | | | |
| Model 16c | | | | | | |
| intercept | 4.15 | [−0.77; 9.74] | 0.08 | 0.67 | 100% | 25% |
| age | −0.04 | [−0.13; 0.04] | | | | |
| gender[b] | −0.39 | [−1.12; 0.31] | | | | |
| cone b-Wave amplitude (int1) | −0.02 | [−0.06; 0.02] | | | | |
| Model 16d | | | | | | |
| intercept | −13.22 | [−32.72; 3.24] | 0.12 | 0.77 | 90% | 42% |
| age | −0.07 | [−0.17; 0.02] | | | | |
| gender[b] | −0.54 | [−1.32; 0.17] | | | | |
| cone b-Wave implicit time (Vmax) | 0.53 | [−0.03; 1.21] | | | | |
| Model 16e | | | | | | |
| intercept | 3.86 | [−0.75; 9.27] | 0.07 | 0.65 | 97% | 17% |
| age | −0.04 | [−0.13; 0.04] | | | | |
| gender[b] | −0.46 | [−1.19; 0.23] | | | | |
| rod a-Wave amplitude (int2) | −0.02 | [−0.06; 0.02] | | | | |
| Model 16f | | | | | | |
| intercept | −21.14 | [−46.24; −2.24] | 0.19 | 0.76 | 93% | 33% |
| age | −0.08 | [−0.2; 0.01] | | | | |
| gender[b] | −0.57 | [−1.4; 0.17] | | | | |
| rod a-Wave implicit time (int2) | 1.08 | [0.21; 2.27] | | | | |
| Model 16g | | | | | | |
| intercept | −1.74 | [−7.49; 3.7] | 0.12 | 0.71 | 97% | 17% |
| age | −0.02 | [−0.11; 0.06] | | | | |
| gender[b] | −0.69 | [−1.54; 0.06] | | | | |
| rod b-Wave amplitude (Vmax) | 0.03 | [0; 0.06] | | | | |
| Model 16h | | | | | | |
| intercept | 3.34 | [−1.64; 8.98] | 0.06 | 0.70 | 93% | 0% |
| age | −0.02 | [−0.11; 0.06] | | | | |
| gender[b] | −0.45 | [−1.17; 0.24] | | | | |
| rod b-Wave implicit time (Vmax) | −0.02 | [−0.09; 0.04] | | | | |
| Model based on 2 ERG parameters[c](Model 17) | | | | | | |
| intercept | −23.79 | [−49.07; −4.24] | 0.26 | 0.88 | 97% | 67% |
| age | −0.09 | [−0.2; 0.01] | | | | |
| gender | −0.86 | [−1.91; 0] | | | | |
| cone b-Wave implicit time (Vmax) | 1.39 | [0.46; 2.68] | | | | |
| rod b-Wave implicit time (int2) | −0.33 | [−0.66; −0.08] | | | | |
| Model based on 3 ERG parameters[c](Model 18) | | | | | | |
| intercept | 17.47 | [5.63; 32.04] | 0.35 | 0.90 | 90% | 50% |
| age | −0.02 | [−0.14; 0.09] | | | | |
| gender | −1.03 | [−2.26; −0.1] | | | | |
| cone a-Wave amplitude (Vmax) | 0.46 | [0.15; 0.91] | | | | |
| rod b-Wave implicit time (int2) | −0.31 | [−0.61; −0.08] | | | | |
| cone a-Wave amplitude (3-int) | −0.44 | [−0.81; −0.19] | | | | |
| Model based on 4 ERG parameters[c](Model 19) | | | | | | |
| intercept | −18.10 | [−54.43; 10.8] | 0.47 | 0.95 | 93% | 75% |
| age | −0.10 | [−0.27; 0.05] | | | | |
| gender | −1.54 | [−3.35; −0.34] | | | | |
| cone a-Wave amplitude (Vmax) | 0.57 | [0.18; 1.19] | | | | |

TABLE 20A-continued

Parameter estimates of the multiple logistic regression to predict good vs. poor response to quetiapine in SZ and BP patients

| Good Vs Poor response | Parameter estimate | | | | | |
|---|---|---|---|---|---|---|
| Parameter(flash intensity[a]) | Value | 95% CI | $R^2$ | AUC | Sensitivity | Specificity |
| rod a-Wave implicit time (int2) | 1.87 | [0.49; 3.94] | | | | |
| rod b-Wave implicit time (int2) | −0.46 | [−0.88; −0.18] | | | | |
| cone a-Wave amplitude (3-int) | −0.47 | [−0.86; −0.19] | | | | |

Note that age and gender are included in models as covariate
[a]In the photopic ERG, the peak maximal response correspond to the «Vmax», «int1» correspond to a fixed intensity of 7.5 cd × s/m$^2$ and «3-int» correspond to an average of three intensities. For the rod function (scotopic ERG), «Vmax» refer to the saturating amplitude observed at the first plateau, where rods only are involved in the response (flash intensity of 0.1 cd × s/m$^2$) and «int2» refer to a flash intensity of 1 cd × s/m$^2$.
[b]Female = 1 and male = 0
[c]When more than one model based on the same number of ERG parameters was possible, only the model that provided the higher accuracy according to the AUC is presented.

TABLE 20B

Prediction of good response to quetiapine in SZ and BP subjects not taking clozapine

| As predicted by the ERGs | Observed response to treatment | | |
|---|---|---|---|
| | Good | Poor | |
| Good response | 97% (29) | 8% (1) | |
| Poor response | 3% (1) | 92% (11) | |
| Total | 30 | 12 | OR = 319 |

Although the present invention has been described hereinabove by way of specific embodiments thereof, it can be modified, without departing from the spirit and nature of the subject invention as defined in the appended claims. The scope of the claims should not be limited by the preferred embodiments set forth in the examples, but should be given the broadest interpretation consistent with the description as a whole. In the claims, the word "comprising" is used as an open-ended term, substantially equivalent to the phrase "including, but not limited to". The singular forms "a", "an" and "the" include corresponding plural references unless the context clearly dictates otherwise.

What is claimed is:

1. A method for treating a subject, the method comprising:
   (a) measuring a plurality of electroretinography (ERG) parameters from a subject suspected of suffering from a major depressive disorder (MDD), schizophrenia (SZ) and/or bipolar disorder (BP);
   (b) calculating MDD, SZ and/or BP probability scores by adjusting the value of said plurality of ERG parameters by one or more transformation analyses;
   (c) determining that the subject suffers from MDD, SZ and/or BP, based on said MDD, SZ and/or BP probability scores;
   and (d) administering to the subject identified in step (c) as suffering from MDD, SZ, and/or BP a psychotropic medication to treat the MDD, SZ, and/or BP.

2. A method for treating a subject according to claim 1, the method comprising:
   (a) measuring a plurality of ERG parameters from a subject suspected of suffering from a major depressive disorder (MDD);
   (b) calculating an MDD probability score by adjusting the value of said plurality of ERG parameters by one or more transformation analyses;
   (c) determining that the subject suffers from MDD based on said MDD probability score; and
   (d) administering to the subject identified in step (c) as suffering from MDD a psychotropic medication to treat the MDD.

3. The method of claim 1, wherein the psychotropic medication is an antidepressant, a stimulant, an antipsychotic, a mood stabilizer, or an anxiolytic.

4. The method of claim 3, wherein the psychotropic medication is selected from the group consisting of quetiapine, aripiprazole, olanzapine, lithium, risperidone, synthroid and clozapine.

5. The method of claim 1, wherein the one or more transformation analyses comprise:
   (i) adjusting the value of the plurality of ERG parameters by weighting coefficients to produce a weighted score for each ERG parameter, and
   (ii) combining the weighted score for each ERG parameter to generate the MDD, SZ and/or BP probability scores.

6. The method of claim 2, wherein the one or more transformation analyses comprise:
   (i) adjusting the value of the plurality of ERG parameters by weighting coefficients to produce a weighted score for each ERG parameter, and
   (ii) combining the weighted score for each ERG parameter to generate the MDD probability score.

7. The method of claim 2, wherein the one or more transformation analyses comprise applying the value of the plurality of ERG parameters to a logistic regression model.

8. The method of claim 7, wherein the logistic regression model was determined using ERG parameter values measured in a first population of MDD subjects and a second population of control subjects.

9. The method of claim 8, wherein the logistic regression model includes age, gender, or both age and gender, as covariate(s).

10. The method of claim 9 wherein the logistic regression model includes both age and gender as covariates.

11. The method of claim 7, wherein said plurality of ERG parameters comprises at least two of the following parameters: the cone a-Wave amplitude (phAamp), the cone a-Wave implicit time (phAlat), the cone b-Wave amplitude (phBamp), the cone b-Wave implicit time (phBlat), the rod a-Wave amplitude (scAamp), the rod a-Wave implicit time (scAlat), the rod b-Wave amplitude (scBamp), the rod b-Wave implicit time (scBlat), the LogK and the Vmax.

12. The method of claim 7, wherein said plurality of ERG parameters comprises at least four of the following parameters: the cone a-Wave amplitude (phAamp), the cone a-Wave implicit time (phAlat), the cone b-Wave amplitude (phBamp), the cone b-Wave implicit time (phBlat), the rod a-Wave amplitude (scAamp), the rod a-Wave implicit time (scAlat), the rod b-Wave amplitude (scBamp), the rod b-Wave implicit time (scBlat), the LogK and the Vmax.

13. The method of claim 12, wherein said plurality of ERG parameters comprises all the following parameters: the cone a-Wave amplitude (phAamp), the cone a-Wave implicit time (phAlat), the cone b-Wave amplitude (phBamp), the cone b-Wave implicit time (phBlat), the rod a-Wave amplitude (scAamp), the rod a-Wave implicit time (scAlat), the rod b-Wave amplitude (scBamp) and the rod b-Wave implicit time (scBlat).

14. A method comprising:
   I. measuring at least (i) the rod a-wave amplitude and/or (ii) the rod b-wave amplitude, in a subject suspected of suffering from a major depressive disorder (MDD),
   II. detecting one or both of the following:
      (a) a rod a-wave amplitude, and/or a rod b-wave amplitude that is lower, relative to the corresponding parameter(s) measured in a control subject not suffering from MDD, or
      (b) a rod a-wave amplitude, and/or a rod b-wave amplitude that is substantially similar or lower, relative to the corresponding parameter(s) measured in a subject suffering from MDD,
   diagnosing that the subject suffers from MDD from detecting (a) and/or (b); and
   IV. upon diagnosing that the subject suffers from MDD, administering a psychotropic medication to the subject to treat MDD.

15. A method comprising:
   I. measuring the cone b-wave implicit time in a subject suspected of suffering from a major depressive disorder (MDD) or schizophrenia (SZ);
   II. determining that the subject suffers from MDD or SZ from the measurement of (I) when:
   (a)
      (i) a cone b-wave implicit time that is similar or higher relative to the corresponding value(s) measured in subjects known to suffer from SZ, or to be predisposed thereto,
      or (ii) a cone b-wave implicit time that is higher relative to the corresponding value measured in subjects known to suffer from MDD or to be predisposed thereto,
   is indicative that said subject suffers from SZ;
   or (b) when:
      (i) a cone b-wave implicit time that is similar or lower relative to the corresponding value(s) measured in subjects known to suffer from MDD or to be predisposed thereto
      or (ii) a cone b-wave implicit time that is lower relative to the corresponding value(s) measured in subjects known to suffer from SZ or to be predisposed thereto,
   is indicative that said subject suffers from MDD;
   and III. administering a psychotropic medication to the subject determined from (II) to suffer from MDD or SZ, to treat the MDD or SZ.

16. A method comprising:
   I. measuring (i) the cone b-wave implicit time and/or (ii) the rod a-wave implicit time in a subject suspected of suffering from a major depressive disorder (MDD) or bipolar disorder (BP);
   II. determining that the subject suffers from MDD or BP when:
   (a)
      (i) a cone b-wave implicit time that is similar or higher and/or a rod a-wave implicit time that is similar or lower relative to the corresponding value(s) measured in subjects known to suffer from BP, or to be predisposed thereto,
      or (ii) a cone b-wave implicit time that is higher and/or a rod a-wave implicit time that is lower relative to the corresponding value(s) measured in subjects known to suffer from MDD or to be predisposed thereto,
   is indicative that said subject suffers from BP;
   and (b) when:
      (i) a cone b-wave implicit time that is similar or lower and/or a rod a-wave implicit time that is similar or higher relative to the corresponding value(s) measured in subjects known to suffer from MDD or to be predisposed thereto,
      or (ii) a cone b-wave implicit time that is lower and/or a rod a-wave implicit time that is higher, relative to the corresponding value(s) measured in subjects known to suffer from BP or to be predisposed thereto,
   is indicative that said subject suffers from MDD
   III. administering a psychotropic medication to the subject determined from (II) to suffer from MDD or BP, to treat the MDD or BP.

17. The method of claim 14, wherein the psychotropic medication is an antidepressant, a stimulant, an antipsychotic, a mood stabilizer, or an anxiolytic.

18. The method of claim 17, wherein the psychotropic medication is selected from the group consisting of quetiapine, aripiprazole, olanzapine, lithium, risperidone, synthroid and clozapine.

19. The method of claim 15, wherein the psychotropic medication is an antidepressant, a stimulant, an antipsychotic, a mood stabilizer, or an anxiolytic.

20. The method of claim 16, wherein the psychotropic medication is an antidepressant, a stimulant, an antipsychotic, a mood stabilizer, or an anxiolytic.

* * * * *